United States Patent
Zhao et al.

(10) Patent No.: US 12,162,938 B2
(45) Date of Patent: Dec. 10, 2024

(54) PURIFICATION PROCESS FOR REMOVAL OF TYROSINE SULFATION ANTIBODY VARIANTS; PURIFIED COMPOSITIONS

(71) Applicant: Merck Sharp & Dohme LLC, Rahway, NJ (US)

(72) Inventors: Jia Zhao, Berkeley Heights, NJ (US); Sandra Rios, Berkeley Heights, NJ (US); Svetlana Dukleska Schussler, Elmwood Park, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 16/343,206

(22) PCT Filed: Oct. 26, 2017

(86) PCT No.: PCT/US2017/058386
§ 371 (c)(1),
(2) Date: Apr. 18, 2019

(87) PCT Pub. No.: WO2018/081329
PCT Pub. Date: May 3, 2018

(65) Prior Publication Data
US 2020/0123251 A1    Apr. 23, 2020

Related U.S. Application Data

(60) Provisional application No. 62/414,209, filed on Oct. 28, 2016.

(51) Int. Cl.
*B01J 47/028* (2017.01)
*C07K 16/06* (2006.01)
*C07K 16/28* (2006.01)

(52) U.S. Cl.
CPC ......... *C07K 16/2803* (2013.01); *B01J 47/028* (2013.01); *C07K 16/06* (2013.01); *C07K 2317/14* (2013.01); *C07K 2317/24* (2013.01); *C07K 2317/40* (2013.01); *C07K 2317/565* (2013.01); *C07K 2317/76* (2013.01)

(58) Field of Classification Search
CPC . B01J 47/028; C07K 2317/14; C07K 2317/40
USPC ...................................................... 424/133.1
See application file for complete search history.

(56) References Cited

U.S. PATENT DOCUMENTS

| | | | |
|---|---|---|---|
| 4,816,567 A | 3/1989 | Cabilly et al. | |
| RE38,313 E | 11/2003 | Faure et al. | |
| 7,795,002 B2 | 9/2010 | Davidson et al. | |
| 10,188,730 B2 * | 1/2019 | Liang | A61P 43/00 |
| 10,898,571 B2 | 1/2021 | Liang et al. | |
| 2004/0192609 A1 | 9/2004 | Farzan et al. | |
| 2007/0027772 A1 | 7/2007 | Widom et al. | |
| 2019/0083614 A1 | 3/2019 | Liang et al. | |
| 2019/0083615 A1 | 3/2019 | Liang et al. | |
| 2019/0091332 A1 | 3/2019 | Liang et al. | |
| 2022/0251194 A1 * | 8/2022 | Fayadat-Dilman | A61P 35/00 |

FOREIGN PATENT DOCUMENTS

| | | |
|---|---|---|
| EP | 1268514 B1 | 6/2006 |
| WO | 2001072769 A2 | 10/2001 |
| WO | 2010019570 A2 | 2/2010 |
| WO | 2013066765 A1 | 5/2013 |
| WO | 2013192215 A1 | 12/2013 |
| WO | 2014067898 A1 | 5/2014 |
| WO | 2014207763 A1 | 12/2014 |
| WO | 2016028672 A1 | 2/2016 |
| WO | 2016118707 A1 | 7/2016 |

OTHER PUBLICATIONS

Tyshchuk et al. (MABS 2019, vol. 11, No. 7, 1219-1232).*
Liu et al. (Biotechnol. J., e2100142. https://doi.org/10.1002/biot.202100142 pp. 1-11; 2021).*
Eastman (product data sheet for dimethylaminopropyl (pp. 1-2; May 6, 2022)).*
Steuerle, Ulrich; Feuerhake, Robert (2006). "Aziridines". Ullmann's Encyclopedia of Industrial Chemistry. Weinheim: Wiley-VCH. doi:10.1002/14356007.a03_239.pub2. (pp. 1-8).*
Li etal (BioProcess International 17(11-12):1-7 (Nov.-Dec. 2019)).*
Anonymous: "Antibody Purification Handbook 18-1037-46 Edition AA", Amersham Pharmacia Biotech, Jan. 1, 2000 (Jan. 1, 2000), XP055315931, Retrieved from the Internet: URL:http://labs.mcb.harvard.edu/Gaudet/Resources Files/GEHealthcare chromatography/Don't move/18103746AA.pdf -[retrieved on Nov. 2, 2016], 108 pages.
Choe, Hyeryun et al., Tyrosine Sulfation of Human Antibodies Contributes to Recognition of the CCR5 Binding Region of HIV-1 gp120, Cell, 2003, 161-170, 114.
Hamilton, Stephen R. et al., Glycosylation engineering in yeast: the advent of fully humanized yeast, Current Opinion in Biotechnology, 2007, 387-392, 18.
Hamilton, Stephen R. et al., Humanization of Yeast to Produce Complex Terminally Sialylated Glycoproteins, Science, 2006, 1441-1443, 313.
Hortin et al., Characterization of Sites of Tyrosine Sulfation in Proteins and Criteria for Predicting Their Occurrence, Biochemical and Biophysical Research Communications, 1986, No. 1, pp. 326-333, 141.

(Continued)

*Primary Examiner* — Lynn A Bristol

(74) *Attorney, Agent, or Firm* — Li Su; Anna L. Cocuzzo

(57) ABSTRACT

The present invention relates to purified antibody and antigen-binding fragment compositions that lack sulfated tyrosine on one or more tyrosine residues in the immunoglobulin chains. Purification methods for removing sulfated tyrosine variants from antibody and antigen-binding fragment compositions are also provided.

24 Claims, 13 Drawing Sheets

Specification includes a Sequence Listing.

(56) References Cited

OTHER PUBLICATIONS

Jia Zhao, et al., Characterization of a novel modification of a CHO-produced mAb: Evidence for the presence of tyrosine sulfation, Characterization of a novel modification of a CHO-produced mAb: Evidence for the presence of tyrosine sulfation, 2017, 985-995, 9, MABS.

Kanan, Yogita et al., Tyrosine O Sulfation: An Overview, JSM Biotechnology & Biomedical Engineering, 2013, 1-5, 1(1).

Kohler et al., Continuous Cultures of Fused Cells Secreting Antibody of Predefined Specificity, Nature, 1975, pp. 495-497, vol. 256.

Liu, Chang C. et al., Efficient expression of tyrosine-sulfated proteins in E coli using an expanded genetic code, Mature Protocols, 2009, 1784-1789, 4(12).

Liu, Hongcheng et al., In vitro and in vivo modifications of recombinant and human IgG antibodies, mAbs, 2014, 1145-1154, 6(5).

Mikesh, Leann M. et al., The Utility of ETD Mass Spectrometry in Proteomic Analysis: Biochimica et Biophysica Acta Proteins and Proteomics Posttranslational Modifications in Proteomics Special Issue, Biochim Biodhys Acta., 2006, 1811-1822, 1764(12).

Monigatti et al., Protein Sulfation Analysis A Primer, Biochem. Biophys Acta, 2006, pp. 1904-1913, 1764.

Nemeth-Cawley, Jennifer F. et al., Analysis of sulfated peptides using positive electrospray ionization tandem mass spectrometry, J. Mass Spectrom., 2001, 1301-1311, 36.

Nett, Juergen H. et al., A combinatorial genetic library approach to target heterologous glycosylation enzymes to the endoplasmic reticulum or the Golgi apparatus of Pichia pastoris, Yeast, 2011, 237-252,28.

Pacis, Efren et al., Effects of cell culture conditions on antibody N-linked glycosylation-what affects high mannose 5 glycoform. Biotechnology and Bioengineering, 2011, 2348-2358, 108(10).

Resta, Leonard G. et al., Selection, design, and engineering of therapeutic antibodies, J. Allergy Clin. Immunol., 2005, 731-736, 116(4).

Rosenquist et al., Analysis of Sequence Requirements for Protein tyrosine Sulfation, Protein Sci., 1993, pp. 215-222, 2.

Roush et al, Synthesis of Computational and Experimental Developability for Manufacturability, Recovery of Biological Products XVII Conference, Jun. 23, 2016, slides 1-2.

Schuurman et al., The inter-heavy chain disulfide bonds of IgG4 are in equilibrium with intra-chain disulfide bonds, Molecular Immunology, 2001, pp. 1-8, vol. 38.

Susanne Andreae et al., Maturation and Activation of Dendritic Cells Induced by Lymphocyte Activation Gene-3 (CD223), The Journal of Immunology, 2002, 3874-3880, 168.

Teramoto et al., Crystal Structure of Human Tyrosylprotein Sulfotransferase 2 Reveals teh Mechanism of Protein Tyrosine Sulfation Reaction, Nat. Commun., 2013, p. 1572, 4.

Xu, Chen et al., Human Anti-CXCR4 Antibodies Undergo VH Replacement, Exhibit Functional V-Region Sulfation, and Define CXCR4 Antigenic Heterogeneity, The Journal of Immunology, 2007, 2408-2418, 179.

Yu, Yonghao et al., Determination of the sites of tyrosine O-sulfation in peptides and proteins, Nature Methods, 2007, 583-588, 4(7).

Zha, D., Glycoengineered Pichia -Based Expression of Monoclonal Antibodies, Methods Mol. Biol., 2013, pp. 31-43, 988.

Kuriakose, Anshu et al., Immunogenicity of Biotherapeutics: Causes and Association with Posttranslational Modifications, Journal of Immunology Research, 2016, 1-18, Article ID 1298473.

Liu, Hongcheng et al., Heterogeneity of Monoclonal Antibodies, J. Pharm. Sci., 2008, 2426-2447, 97(7).

Moore, Kevin L., The Biology and Enzymology of Protein Tyrosine O-Sulfation, The Journal of Biological Chemistry, 2003, 24243-24246, 278:27.

Amano, Yukari et al., Ion-selective enrichment of tyrosine-sulfated peptides from complex protein digests, Analytical Biochemistry, 346, 124-131, 2005.

Coffman, Jonathan L. et al., High-Throughput Screening of Chromatographic Separations: I. Method Development and Column Modeling, Biotechnology and Bioengineering, 100(4), 605-618, 2008.

Kanan, Yogita et al., Complement Factor H, Vitronectin, and Opticin Are Tyrosine-Sulfated Proteins of the Retinal Pigment Epithelium, PLoS One, 9(8): e105409, 1-10, 2014.

Schwessinger, Benjamin et al., A second-generation expression system for tyrosine sulfated proteins and its application in crop protection, Integr Biol (Camb), 8(4), 542-545, 2016.

Chen, X. et al., Human anti-CXCR4 antibodies undergo VH replacement, exhibit functional V region sulfation, and define CXCR4 antigenic heterogenity, Journal of Immunology, 179(4), 2408-2418, 2007.

Hyeryun, C., et al., Tyrosine Sulfation of Human Antibodies Contributes to Recognition of the CCR5 Binding Region of HIV-1 gp120., Cell, 114(2), 161-170, 2003.

* cited by examiner

PURIFICATION PROCESS FOR REMOVAL OF TYROSINE SULFATION ANTIBODY VARIANTS; PURIFIED COMPOSITIONS

FIELD OF THE INVENTION

The present invention relate to compositions comprising antibodies and antigen-binding fragments thereof that lack tyrosine sulfation as well as methods of purification for preparing compositions.

BACKGROUND OF THE INVENTION

Tyrosine sulfation is a post-translational modification (PTM) where a sulfate trioxide ($SO_3$) group is covalently bound to the hydroxyl group on the side chain of the amino acid tyrosine group. This PTM occurs in the trans-Golgi network and is catalyzed by two enzymes, tyrosylprotein sulfotransferases (TPSTs). The molecular mechanism involves the transfer of an activated sulfate from 3'-phosphoadenosine-5'-phosphosulfate to tyrosine, and has been found on a variety of proteins and peptides. Recent findings indicate that tyrosylprotein sulfotransferase 2 recognizes tyrosines flanked by acid residues for sulfation. This PTM is responsible for strengthening interactions between proteins and occurs on secreted and trans-membrane spanning proteins. Some chemokine receptors have been shown to be tyrosine sulfated such as at the N-terminal extracellular domain of CCR5, the principle HIV-1 and several glycoprotein hormone receptors. For example, the native form of the leech-derived thrombin inhibiting peptide hirudin, is tyrosine sulfated. Interestingly, the two recombinant forms of hirudin (Revasc and Refludan) used for treating various blood clotting disorders are not sulfated. Sulfation increases the mass of a biomolecule by 80 Da, which is the same mass difference as a phosphate moiety ($PO_3$). Unlike $PO_3$, which forms a fairly stable P—O bond, the $SO_3$ is very labile and readily decomposes under high temperature and low pH conditions.

The presence of different PTM variants in a therapeutic antibody preparation leads to heterogeneity which, depending on the location of the modification, can lead to variations in antibody potency, bioavailability or immunogenicity. Such issues also create issues before regulatory agencies. Though tyrosine sulfation has been described in chemokine receptors and other proteins, there is a need to identify if such modifications occur in antibody preparations and, if identified, to remove them.

SUMMARY OF THE INVENTION

The present invention provides a composition comprising an anti-LAG3 antibody or antigen-binding fragment thereof (e.g., Ab1, Ab2, Ab3, Ab4, Ab5, Ab6, Ab7, Ab8 or Ab9) that, for example, comprises: a light chain variable domain comprising:
CDR-L1 that comprises the amino acid sequence: KASQSLDYEGDSDMN (SEQ ID NO: 38);
CDR-L2 that comprises the amino acid sequence: GASNLES (SEQ ID NO: 39); and
CDR-L3 that comprises the amino acid sequence: QQSTEDPRT (SEQ ID NO: 40); and/or a heavy chain variable domain comprising:
CDR-H1 that comprises the amino acid sequence: DYNVD (SEQ ID NO: 33);
CDR-H2 that comprises the amino acid sequence:

DINPNNGGTIYAQKFQE; (SEQ ID NO: 59)

DINPNSGGTIYAQKFQE; (SEQ ID NO: 60)

DINPNDGGTIYAQKFQE; (SEQ ID NO: 61)

DINPNQGGTIYAQKFQE; (SEQ ID NO: 62)

DINPNGGGTIYAQKFQE; (SEQ ID NO: 63)
or

DINPNX$_1$GGTIYX$_2$QKFX$_3$X$_4$ (SEQ ID NO: 64)

wherein, $X_1$=D, N, S or Q, $X_2$=A or S, $X_3$=Q or K, and $X_4$=E or G; and CDR-H3: NYRWFGAMDH (SEQ ID NO: 35); which lacks detectable levels of sulfated tyrosine on CDR-L1. For example, in an embodiment of the invention, the antibodies or fragments in the composition further lack detectable levels of sulfated tyrosine in one or more members selected from the group consisting of FR-L1, FR-L2, CDR-L2, FR-L3, CDR-L3, FR-L4, FR—H1, CDR-H1, FR—H2, CDR-H2, FR—H3, CDR-H3, FR—H4 and a constant domain. In an embodiment of the invention, the antibody or fragment comprises engineered yeast or CHO N-linked glycans. In an embodiment of the invention, an anti-LAG3 antibody (e.g., Ab1, Ab2, Ab3, Ab4, Ab5, Ab6, Ab7, Ab8 or Ab9) containing composition comprises one or more species of the antibody lacking tyrosine sulfation and having molecular weights of about 148590 Da, 148752 Da and/or 148914 Da (e.g., having G0F and/or G1F glycan species, e.g., as set forth in Table 1, N-terminal heavy chain glutamine converted to pyroglutamate and/or C-terminal heavy chain lysine removed).

The present invention also provides a method for removing tyrosine sulfated antibodies or antigen-binding fragments thereof (e.g., Ab1, Ab2, Ab3, Ab4, Ab5, Ab6, Ab7, Ab8 or Ab9) from an aqueous mixture comprising antibodies or antigen-binding fragments that comprise one or more sulfated tyrosines (e.g., on CDR-L1) and antibodies or antigen-binding fragments lacking sulfated tyrosine comprising adjusting the pH of the mixture to about 6.5 to about 7.0 or about 6.5 to about 7.5, contacting the mixture with an anion exchange resin, and removing and retaining a non-resin bound aqueous fraction of the mixture from the resin. In an embodiment of the invention, the method comprises washing the column with an aqueous composition, e.g., under isocratic conditions, and removing and retaining the wash composition from the resin. In an embodiment of the invention, the resin is in a column and the method comprises adding said mixture to the column and collecting the flow-through fraction from the column. In an embodiment of the invention, the method comprises equilibrating a chromatography resin, comprising a dimethylaminopropyl anion exchange ligand, in a chromatography column with 25 mM sodium phosphate pH 6.5, adjusting the pH of the mixture to about 6.5, applying the mixture to the column, collecting flow-through fraction form the column, washing the resin in the column with 25 mM sodium phosphate pH 6.5 and collecting the flow-through fraction from the wash. In an embodiment of the invention, the method comprises equilibrating a chromatography resin, comprising a quaternized polyethyleneimine anion exchange ligand, in a chromatography column with 5 mM sodium phosphate pH 7.0; optionally, 5 mM NaCl, adjusting the pH of the mixture to about 7.0, applying the mixture to the column, collecting flow-through fraction form the column, washing the resin in the column with 25 mM sodium phosphate pH 7.0; optionally, 5 mM NaCl and collecting the flow-through fraction from the wash. In an embodiment of the invention, the $A_{280}$ absorbance of the anion exchange chromatography flow-through is monitored and collected and retained when the $A_{280}$ first reaches at least about 2.5 absorbance units/cm; and not collected or retained when the $A_{280}$ falls below about 1.0 absorbance units/cm. In an embodiment of the invention, the methods of the present invention further comprise purifying the antibody or antigen-binding fragment by cation exchange chromatography, further anion exchange chromatography in bind-elute mode, hydrophobic interaction chromatography, protein-A chromatography, protein-L chromatography, protein-G chromatography, hydroxyapatite chromatography, size exclusion chromatography, fractional precipitation, filtration, centrifugation or viral inactivation. In an embodiment of the invention, the immunoglobulin light chains and/or heavy chains of the antibody or antigen-binding fragment are expressed in a Chinese hamster ovary cell. In an embodiment of the invention, the antibody or antigen-binding fragment comprises:

a light chain variable domain comprising:
CDR-L1 that comprises the amino acid sequence: KASQSLDYEGDSDMN (SEQ ID NO: 38);
CDR-L2 that comprises the amino acid sequence: GASNLES (SEQ ID NO: 39); and
CDR-L3 that comprises the amino acid sequence: QQSTEDPRT (SEQ ID NO: 40); and/or a heavy chain variable domain comprising:
CDR-H1 that comprises the amino acid sequence: DYNVD (SEQ ID NO: 33);
CDR-H2 that comprises the amino acid sequence:

DINPNNGGTIYAQKFQE; (SEQ ID NO: 59)

DINPNSGGTIYAQKFQE; (SEQ ID NO: 60)

DINPNDGGTIYAQKFQE; (SEQ ID NO: 61)

DINPNQGGTIYAQKFQE; (SEQ ID NO: 62)

DINPNGGGTIYAQKFQE; (SEQ ID NO: 63)
or

DINPNX₁GGTIYX₂QKFX₃X₄ (SEQ ID NO: 64)

wherein, $X_1$=D, N, S or Q, $X_2$=A or S, $X_3$=Q or K, and $X_4$=E or G; and CDR-H3: NYRWFGAMDH (SEQ ID NO: 35). Compositions that are the product of such a method are also part of the present invention. In an embodiment of the invention, an anti-LAG3 antibody (e.g., Ab1, Ab2, Ab3, Ab4, Ab5, Ab6, Ab7, Ab8 or Ab9) is purified by AEX chromatography wherein the antibodies lacking sulfated tyrosine, having molecular weights of about 148590 Da, 148752 Da and/or 148914 Da (e.g., having G0F and/or G1F glycan species, e.g., as set forth in Table 1, N-terminal heavy chain glutamine converted to pyroglutamate and/or C-terminal heavy chain lysine removed).

DETAILED DESCRIPTION OF THE INVENTION

Figure 1:
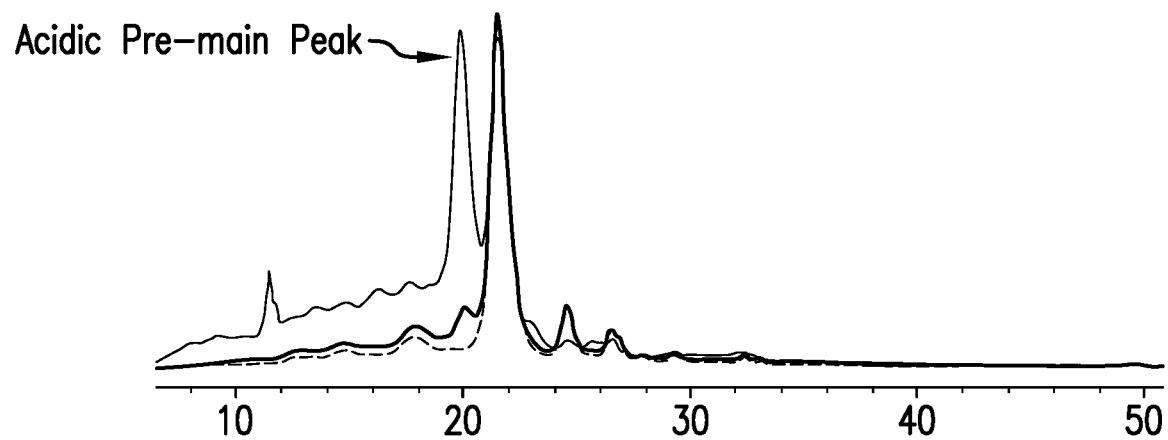
FIG. 1. Overlay of IEX-HPLC UV profile of AEX feed (bold trace), strip (light trace) and pool fraction (dashed trace).

Certain antibodies and other proteins expressed in Chinese hamster ovary (CHO) cells are contaminated with a sulfated tyrosine variants. Mass spectrographic analysis of such variants is characterized by an adduct of about +80 Da which corresponds to the mass of an added sulfate group. Such adducts are also alkaline phosphatase resistant and reactive with anti-sulfated tyrosine antibodies. The present invention provides a method for purifying a composition including such contaminant tyrosine sulfated variants as well as antibody compositions essentially free of the variants.

In accordance with the present invention there may be employed conventional molecular biology, microbiology, and recombinant DNA techniques within the skill of the art.

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., James M. Cregg (Editor), *Pichia* Protocols (Methods in Molecular Biology), Humana Press (2010), Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane, Antibodies: A Laboratory Manual, Cold Spring Harbor Laboratory Press, Cold Spring Harbor, N.Y. (1990); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol I, CRC Press (1976); Handbook of Biochemistry: Section A Proteins, Vol II, CRC Press (1976); Essentials of Glycobiology, Cold Spring Harbor Laboratory Press (1999), Animal Cell Culture (R. I. Freshney, ed. (1986)); Immobilized Cells And Enzymes (IRL Press, (1986)); B. Perbal, A Practical Guide To Molecular Cloning (1984).

A sulfated tyrosine includes a tyrosine having an added sulfate group, e.g., having the structure:

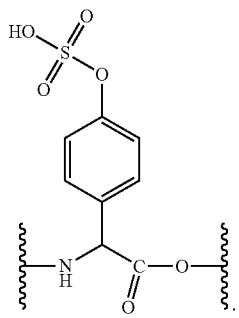 [SMILES: *NC(C(=O)O*)c1ccc(OS(=O)(=O)O)cc1]

Chromatography

The present invention provides a method for removing contaminant variant antibodies or antigen-binding fragments (e.g., Ab1-Ab9) thereof that comprise sulfated tyrosine from a composition, e.g., a composition that comprises a mixture of antibodies or fragments, some of which having sulfated tyrosine and some of which lacking the sulfated tyrosine to generate a composition comprising undetectable levels of tyrosine sulfated variants (e.g., tyrosine sulfated CDR-L1, e.g., of Ab1 or Ab6). In an embodiment of the invention, the composition is treated by anion exchange (AEX) chromatography in flow-through mode to remove tyrosine sulfated variants. In an embodiment of the invention, the AEX resin has a dimethylaminopropyl ligand (i.e., a ligand that includes a dimethylaminopropyl moiety). For example, in an embodiment of the invention, the composition that is subjected to the AEX chromatography is the product of prior protein-A chromatographic purification. In an embodiment of the invention, the composition is pH adjusted to a pH of about 6.5, e.g., with Tris (tris(hydroxymethyl)aminomethane) (e.g., 0.5M, 0.725M or 1M) prior to AEX treatment (e.g., having a dimethylaminopropyl ligand). In an embodiment of the invention, the AEX column (e.g., having a dimethylaminopropyl ligand) is equilibrated, e.g., with sodium phosphate, e.g., 25 mM, e.g., sodium phosphate pH 5, 6.2 or 6.5. The column (e.g., having a dimethylaminopropyl ligand) can, in an embodiment of the invention, be washed with buffer (e.g., with sodium phosphate, e.g., 25 mM, e.g., sodium phosphate pH 6.5) to recover antibody or fragment within the column, but not tightly bound to the AEX resin. Flow-through, not tightly bound to the AEX resin, is collected (e.g., in fractions) and, for example, pooled. In an embodiment of the invention, after use, the column is stripped, e.g., with 1M NaCl.

Mass spectrometric analysis of the AEX flow-through material revealed several glycosylated species of Ab6 lacking tyrosine sulfation on CDR-L1. These species are summarized below in Table 1. These theoretical masses refer to the calculated mass of the Ab6 molecule with an N-terminal glutamine on the heavy chain converted to N-terminal pyroglutamic acid (pE1) and a C-terminal lysine on the heavy chain removed (—K).

TABLE 1

| Intact Mass Summary | | | |
|---|---|---|---|
| | G0F, pE1, -K,/ G0F, pE1, -K | G1F, pE1, -K/ G0F, pE1, -K | G1F, pE1, -K/ G1F, pE1, -K |
| Theoretical Mass (Da) | 148590 | 148752 | 148914 |
| Observed Mass in Pool Fraction (Da) | 148590 | 148749 | 148915 |

Figure 11:
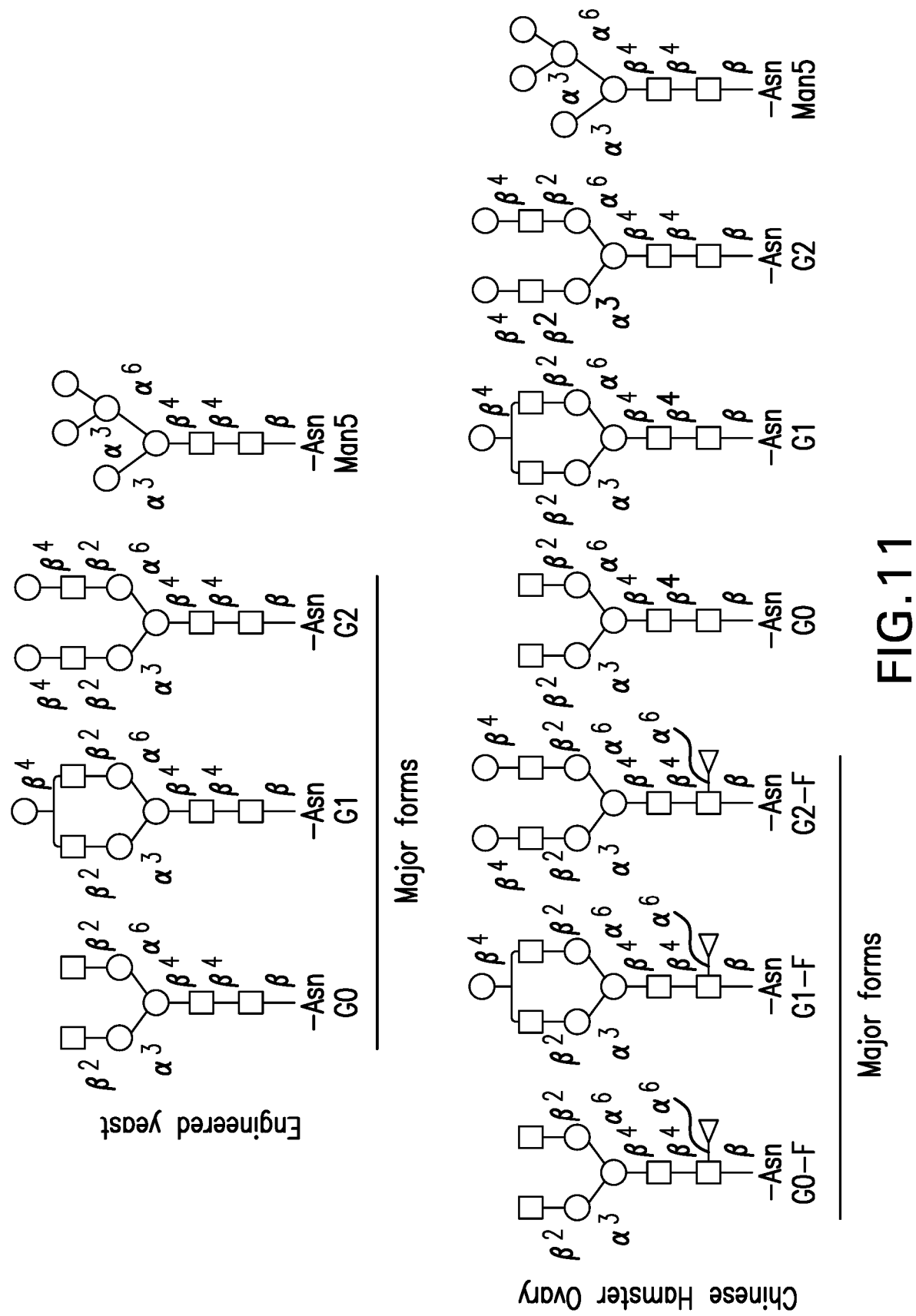
FIG. 11. Predominant N-linked glycans for monoclonal antibodies produced in Chinese hamster ovary cells (CHO N-linked glycans) and in engineered yeast cells (engineered yeast N-linked glycans): squares: N-acetylglucosamine (GlcNac); circles: mannose (Man); diamonds: galactose (Gal); triangles: fucose (Fuc).

*Refer to FIG. 11 for the identity of the glycan species G0F and G1F

The present invention includes a composition comprising anti-LAG3 antibodies (e.g., Ab1, Ab2, Ab3, Ab4, Ab5, Ab6, Ab7, Ab8 or Ab9; preferably Ab6) lacking detectable levels of tyrosine sulfation, e.g., on CDR-L1, comprising species having one or more molecular weights of about 148590, 148749, and/or 148915; and/or comprising the glycan species G0F and/or G1F.

Flow-through mode refers to purification of a polypeptide, using a chromatography resin, by a method that does not include an elution step for the recovery of the polypeptide. In such a method, the polypeptide of interest does not bind tightly to the resin, but contaminant substances to be removed from the polypeptides of interest do bind tightly to the resin. For example, an AEX resin is used in flow-through mode in a method comprising loading a composition that comprises contaminant variant antibodies having tyrosine sulfation and antibodies lacking tyrosine sulfation onto a column containing the AEX resin and collecting and retaining the antibody or fragment in the flow-through of the column. Unbound antibody lacking sulfation can be washed out of the column (and retained) under conditions that do not lead to elution, e.g., isocratic conditions. In such a method, the contaminant remains bound to the column and the antibody lacking the tyrosine sulfation would remain in the flow-through.

Bind/elute mode refers to purification of a polypeptide using a chromatography resin by a method that includes an elution step. In such a method, the polypeptide of interest binds tightly to the resin, but contaminant substances to be removed from the polypeptides of interest do bind tightly to the resin. With a chromatography column, the contaminants flow through the column and remain largely unbound to the resin. Bound antibodies, following an optional wash, are unbound and collected and retained when exposed to an elution buffer that causes unbinding from the resin.

A chromatography resin ligand is a substance that is fixed to a stationary phase particle (e.g., a Sepharose® particle), which reversibly binds a desired molecule (e.g., antibody or contaminant) present in the multi-component mobile phase.

In an embodiment of the invention, the AEX resin has the ligand quaternized polyethyleneimine (i.e., a ligand that includes a quaternized polyethyleneimine moiety). In an embodiment of the invention, the resin (e.g., having a quaternized polyethyleneimine ligand) is pre-equilibrated with 1M NaCl. In an embodiment of the invention, the resin (e.g., having a quaternized polyethyleneimine ligand) is equilibrated with sodium phosphate, e.g., 25 mM and NaCl, e.g., 5 mM; pH about 7.0. In an embodiment of the invention, the column (e.g., having a quaternized polyethyleneimine ligand) is loaded with the feed and washed with sodium phosphate, e.g., 25 mM and NaCl, e.g., 5 mM; pH about 7.0; and the flow-through is collected, e.g., in fractions, e.g., and pooled. In another embodiment of the invention, the method of the invention comprises equilibrating a chromatography resin, comprising an anion exchange ligand, in a chromatography column with about 10-50 mM sodium phosphate; pH about 6.5 to 7.5, adjusting the pH of the mixture to about 6.5 to 7.5, applying the mixture to the column, collecting flow-through fraction from the column, washing the resin in the column with about 10-50 mM sodium phosphate; pH about 6.5 to 7.5 and collecting flow-through fraction from the wash. In a further embodiment of the invention, the method of the invention comprises equilibrating a chromatography resin, comprising an anion exchange ligand, in a chromatography column with about 10-50 mM sodium phosphate; pH about 6.5 to 7.0, adjusting the pH of the mixture to about 6.5 to 7.0, applying the mixture to the column, collecting flow-through fraction from the column, washing the resin in the column with about 10-50 mM sodium phosphate; pH about 6.5 to 7.0 and collecting flow-through fraction from the wash.

Any suitable quantity of antibody or antigen-binding fragment can be loaded onto a chromatography resin, e.g., a chromatography column (e.g., AEX having a quaternized polyethyleneimine ligand or dimethylaminopropyl ligand). For example, in an embodiment of the invention, about 100, 110, 120, 130, 140, 150, 100-150, 160, 170, 180, 190, 200, 300, 150-200, 100-200, 250-350, or 280-320 grams of material, e.g., antibody or fragment, is loaded per liter of resin (e.g., AEX having a quaternized polyethyleneimine ligand or dimethylaminopropyl ligand).

If a chromatography column is used (e.g., containing an AEX resin having a quaternized polyethyleneimine ligand or dimethylaminopropyl ligand), any acceptable dimension can be used. For example, in an embodiment of the invention, the column diameter or height is about 7, 8, 9, 10, 11, 12, 13, 14, 15, 16, 17, 18, 19, 20, 21, 22, 23, 24, 25, 26, 27, 28, 29 or 30 cm.

Flow rate refers to the volume of mobile phase passing through the column (e.g., containing an AEX resin having a quaternized polyethyleneimine ligand or dimethylaminopropyl ligand) over a period of time. In an embodiment of the invention, the flow rate is about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215 liters per hour.

In an embodiment of the invention, the absorbance at 280 nm ($A_{280}$) of the flow-through of the column (e.g., containing an AEX resin having a quaternized polyethyleneimine ligand or dimethylaminopropyl ligand) is monitored. In an embodiment of the invention, the antibody or fragment product in the major $A_{280}$ peak of the flow-through is collected and retained. In an embodiment of the invention, flow-through is collected when the $A_2BD$ reaches about 1.0, 1.5, 2.0, 2.5 or 3.0 $A_{280}$ absorbance units per cm (path length) and collection ceases when the $A_{280}$ drops below about 1.0, 1.5, 2.0, 2.5 or 3.0 $A_{280}$ absorbance units per cm (path length).

In order to protect chromatography columns (e.g., containing an AEX resin having a quaternized polyethyleneimine ligand or dimethylaminopropyl ligand) from clogging due to particulate matter in the mobile phase, a pre-column filter can be used. In an embodiment of the invention, the filter is a polyethersulfone membrane. Also, a post-column filter can be used to filter out any particulates from the flow-through. In an embodiment of the invention, the filter has a 0.2 or 0.5 μm pore size.

The presence of the variant having sulfated tyrosine can be confirmed, e.g., by mass spectrographic analysis of flow-through fractions. Sulfated variants will have a higher mass than non-sulfated variants. For example, in an embodiment of the invention, the sulfated variant is about 80 Da heavier than variants lacking sulfation. In an embodiment of the invention, the sulfation is resistant to digestion by phosphatase and the sulfated peptide has different fragmentation pattern by electron transfer dissociation (ETD) compared to phosphorylated peptides.

In an embodiment of the invention, a composition comprising antibodies (e.g., Ab1, Ab2, Ab3, Ab4, Ab5, Ab6, Ab7, Ab8 or Ab9; preferably Ab6) lacking tyrosine sulfation refers to a composition lacking detectable tyrosine sulfation (e.g., at CDR-L1). A composition comprising undetectable levels of tyrosine sulfation (e.g., at CDR-L1) comprises a level that cannot be observed by mass spectrometric analysis of the composition. For example, in an embodiment of the invention, mass spectrometric analysis of the composition is performed by intact and reduced mass measurement and reduced peptide mapping of the immunoglobulin peptides of the composition. In an embodiment of the invention, the reduced peptide mapping includes denaturation and reduction of the antibody immunoglobulin disulfide bonds and alkylation of the free cysteines, followed by enzymatic digestion (e.g., using LysC, Trypsin or GluC). The enzymatic digested peptides were analyzed by mass spectrometry. In an embodiment of the invention, an "undetectable" level refers to less than about 0.5% (less than about 0.4, 0.3, 0.2, 0.1%) tyrosine sulfated species (e.g., on CDR-L1) compared to unmodified species in the composition.

Molecular weight of a polypeptide can be calculated, e.g., based on the known weights of the amino acids (modified or unmodified/sulfated or unsulfated) and known modifications (e.g. oxidation, deamidation, glycosylation, C and N terminal modification). Molecular weight can be measured by mass spectrometric analysis, e.g., when coupled with liquid chromatography. In an embodiment of the invention, the mass spectrometry is quadrupole time-of-flight (Q-TOF) mass spectrometry or Orbitrap mass spectrometry.

The term "chromatography" refers to the process by which a solute of interest, e.g., a substance in a composition is separated from other substances in the composition by contacting the substances to a resin which acts as an adsorbent. The adsorbent which adsorbs or retains a substance more or less strongly due, e.g., to properties of the solute, such as pI, hydrophobicity, size and structure, under particular buffering conditions of the process. Chromatography can be performed by traditional methods of percolation of a composition through a bed of chormatography resin, e.g., through a column containing the resin. Batch chromatography purification includes preparing a slurry of the resin and contacting the antibody or fragment containing composition with the slurry to adsorb the substance to be separated to the resin. The solution comprising the substance not bound to the resin is separated from the slurry, e.g., by allowing the slurry to settle and removing the supernatant and the non-bound substance can be retained or discarded. The slurry is optionally subjected to one or more wash steps. If desired, the slurry can be contacted with an appropriate elution buffer to desorb resin-bound substances from the resin. The desorbed substance can be retained or discarded. In an embodiment of the invention, sulfated tyrosine variants of an antibody in a composition are bound to an anion exchange resin while non-sulfated tyrosine variants do not bind significantly to the resin.

In an embodiment of the invention, an antibody or antigen-binding fragment thereof is purified by protein-A or protein-G chromatography. Protein-G and protein-A are bacterial proteins from Group G Streptococci and *Staphylococcus aureus*, respectively. The affinity of protein-G and protein-A for the Fc region of IgG-type antibodies forms the basis for purification of IgG, IgG fragments containing the Fc region, and IgG subclasses. Protein-A or protein-G can be coupled to solid phase such as Sepharose®, which can be used for protein-A or protein-G chromatography. The present invention includes methods for making a composition comprising an antibody or antigen-binding fragment thereof lacking detectable levels of sulfated tyrosine variant or for purifying an antibody or antigen-binding fragment thereof to remove the sulfated tyrosine variants by a method including AEX chromatography in flow-through mode and protein-A and/or protein-G.

In an embodiment of the invention, an antibody or antigen-binding fragment thereof is purified by multimodal chromatography (mixed-mode). Multimodal or mixed-mode protein chromatography is based on resins that have been functionalized with ligands capable of multiple modes of interaction, e.g., ion exchange, hydroxyapatite, affinity, size exclusion, and/or hydrophobic interactions. The present invention includes methods for making a composition comprising an antibody or antigen-binding fragment thereof lacking detectable levels of sulfated tyrosine variant or for purifying an antibody or antigen-binding fragment thereof to remove the sulfated tyrosine variants by a method including AEX chromatography in flow-through mode and mixed mode chromatography.

In an embodiment of the invention, an antibody or antigen-binding fragment thereof is purified by protein-L chromatography. Protein L is a *Peptostreptococcus magnus* protein that binds immunoglobulins through the immunoglobulin light chain. Protein L binds to representatives of all antibody classes, including IgG, IgM, IgA, IgE, and IgD. Recombinant protein L binds to the variable region of the kappa light chain of immunoglobulins and immunoglobulin fragments. Protein L binds to three of four kappa light chain subtypes in humans (1, 3, and 4) and kappa 1 in mice. The present invention includes methods for making a composition comprising an antibody or antigen-binding fragment thereof lacking detectable levels of sulfated tyrosine variant or for purifying an antibody or antigen-binding fragment thereof to remove the sulfated tyrosine variants by a method including AEX chromatography in flow-through mode and protein-L chromatography.

In an embodiment of the invention, an antibody or antigen-binding fragment thereof is purified by hydrophobic interaction chromatography (HIC). HIC separates proteins with differences in hydrophobicity. Separation is based on the reversible interaction between a protein and the hydrophobic surface of a chromatography medium. The present invention includes methods for making a composition comprising an antibody or antigen-binding fragment thereof lacking detectable levels of sulfated tyrosine variant or for purifying an antibody or antigen-binding fragment thereof to remove the sulfated tyrosine variants by a method including AEX chromatography in flow-through mode and HIC.

In an embodiment of the invention, an antibody or antigen-binding fragment thereof is purified by size exclusion chromatography (SEC). SEC separates proteins with differences in molecular size. The present invention includes methods for a composition comprising making an antibody or antigen-binding fragment thereof lacking detectable levels of sulfated tyrosine variant or for purifying an antibody or antigen-binding fragment thereof to remove the sulfated tyrosine variants by a method including AEX chromatography in flow-through mode and SEC chromatography.

In an embodiment of the invention, the antibody or antigen-binding fragment is subjected to viral inactivation. For example, in an embodiment of the invention, viral inactivation is done by pH treatment of compositions including an antibody or antigen-binding fragment thereof. Specifically, direct exposure of a composition to pH extremes can be used for viral clearance. For example, pH treatment is, in an embodiment of the invention, low pH treatment (e.g., pH 3.0-3.6). In an embodiment of the invention, the antibodies or antigen-binding fragments are subject to high pH treatment. In an embodiment of the invention, viral inactivation is performed with solvent or detergent of compositions including an antibody or antigen-binding fragment thereof. The present invention includes methods for making a composition comprising an antibody or antigen-binding fragment thereof lacking detectable levels of sulfated tyrosine variant or for purifying an antibody or antigen-binding fragment thereof to remove the sulfated tyrosine variants by a method including AEX chromatography in flow-through mode and viral inactivation.

"Ion exchange" separates molecules on the basis of differences in their net surface charge. Molecules vary considerably in their charge properties and will exhibit different degrees of interaction with charged chromatography resins according to differences in their overall charge, charge density, and surface charge distribution. In an embodiment of the invention, an antibody or antigen-binding fragment thereof is purified by ion exchange chromatography. "Ion-exchange chromatography" includes cation exchange, anion exchange, and mixed mode chromatographies.

The phrase "ion exchange" resin refers to a solid phase that is negatively charged (i.e., a cation exchange) or positively charged (i.e., an anion exchange).

In an embodiment of the invention, an antibody or antigen-binding fragment thereof is purified by cation exchange chromatography. A "cation exchange" resin refers to a solid phase which is negatively charged, and which has free cations for exchange with cations in an aqueous solution passed over or through the solid phase. Any negatively charged ligand attached to the solid phase suitable to form the cation exchange resin can be used. Cation exchange materials include, but are not limited to those having the ligand: sulfopropyl (SP) —$CH_2$—$CH_2$—$CH_2$—$SO_3^-$; methyl sulfonate (S) —$CH_2$—$SO_3$; or carboxymethyl (CM) —$CH_2$—$COO^-$. The present invention includes methods for making a composition comprising antibody or antigen-binding fragment thereof lacking detectable levels of sulfated tyrosine variant or for purifying an antibody or antigen-binding fragment thereof to remove the sulfated tyrosine variants by a method including AEX chromatography in flow-through mode and cation exchange chromatography.

In an embodiment of the invention, an antibody or antigen-binding fragment thereof is purified by anion exchange chromatography. An "anion exchange" resin refers to a solid phase which is positively charged, thus having one or more positively charged ligands attached thereto. Any positively charged ligand attached to the solid phase suitable to form the anionic exchange resin can be used. Anion exchange materials include, but are not limited to those having the ligand: quaternary ammonium (Q) —$CH_2$—$N+$—$(CH_3)_3$; diethylaminoethyl (DEAE) —$CH_2$—$CH_2$—$N+$—$(CH_2$—$CH_3)_2$; or diethylaminopropyl (ANX) —$CH_2$—$CHOH$—$CH_2$—$N+$—$(CH_2$—$CH_3)_2$. The GoPure D™ 50 μm column has a dimethylaminopropyl functional group. The present invention includes methods for making a composition comprising an antibody or antigen-binding fragment thereof lacking detectable levels of sulfated tyrosine variant or for purifying an antibody or antigen-binding fragment thereof to remove the sulfated tyrosine variants by a method including AEX chromatography in flow-through mode and AEX chromatography (in bind/elute mode) chromatography.

The term "solid phase" or "stationary phase" is used to mean any non-aqueous matrix to which one or more ligands (e.g., anion exchange ligands or cation exchange ligands) can adhere or alternatively, in the case of size exclusion chromatography, it can refer to the gel structure of a resin. The mobile phase is the liquid, e.g., aqueous substance that carries the antibody or antigen-binding fragment over the solid phase is a chromatographic purification. The mobile phase may include the loading buffer that is applied to the column. Examples of materials that can be used to form the solid phase include polysaccharides (such as agarose and cellulose) and other mechanically stable matrices such as silica (e.g., controlled pore glass), poly(styrenedivinyl)benzene, polyacrylamide, ceramic particles and derivatives of any of these.

An "equilibration" buffer or solution is used to adjust the pH and conductivity of the chromatography resin prior to loading with the mixture containing the antibody or antigen-binding fragment for purification. Suitable buffers or solutions that can be used for this purpose are well known in the art, e.g., such as buffers described above, and include any buffer at pH that is compatible with the selected resin used in the chromatography step for purifying the protein of interest.

A "loading" buffer or solution is used to load the mixture containing the antibody or antigen-binding fragment onto a purification resin (e.g., anion exchange resin or cation exchange resin). Any appropriate solution can be used as the loading buffer. In an embodiment of the invention, the loading buffer is prepared from a buffered mixture derived from a previous purification step such as the elution buffer.

The terms "wash" buffer or solution is a composition used to elute one or more impurities from the purification resin (e.g., anion exchange resin or cation exchange resin) prior to eluting the antibody or antigen-binding fragment. The term "washing" describes the passing of an appropriate composition through or over the chromatography resin. In an embodiment of the invention, the wash is isocratic. Under isocratic wash conditions, the mobile phase of the chromatography remains essentially the same.

Though tyrosine sulfated variant antibodies and antigen-binding fragments are contaminants, the present invention includes compositions comprising such variants e.g., bound to an AEX chromatography resin or unbound in the absence of un-tyrosine sulfated variants. The unbound variants can be obtained by eluting from the AEX column following removal from the un-tyrosine sulfated antibodies and fragments.

An "elution" buffer dissociates a molecule (e.g., an antibody or antigen-binding fragment thereof) bound to a chromatography resin.

Upstream Processing

Antibodies and antigen-binding fragments which are to be purified of contaminant tyrosine sulfated variants can be generated by host cell expression. For example, a method of the present invention includes, in an embodiment, prior to removal of the variants, the expression of the heavy and/or light immunoglobulin chains in a host cell in a culture medium under conditions favorable to such expression and isolation of the antibodies or antigen-binding fragments from the host cell and/or culture medium. The present invention includes methods for making a composition comprising an antibody or antigen-binding fragment thereof lacking detectable levels of sulfated tyrosine variants or for purifying an antibody or antigen-binding fragment thereof to remove the sulfated tyrosine variants by a method including host cell expression and AEX chromatography in flow-through mode.

The scope of the present invention includes methods for producing a composition comprising antibodies or antigen-binding fragments which are free of tyrosine sulfation (e.g., on CDR-L1 thereof) comprising (i) introducing a polynucleotide encoding immunoglobulin light and/or heavy chains of said antibodies or fragments into a host cell (e.g., a CHO cell) and (ii) culturing the host cell under conditions favorable to expression of the immunoglobulin chains in the cell, e.g., wherein the antibody or antigen-binding fragment having the immunoglobulin chain(s) is secreted from the host cell into the culture medium, and (iii) isolating the immunoglobulin chain polypeptide(s) from the host cell and/or culture medium by a method that includes anion exchange chromatography in flow-through mode as is discussed herein.

For example, the antibodies or fragments can be released from a host cell by lysis, e.g., methods such as grinding/abrasion (e.g., with glass beads), French press cell lysis, enzymatic digestion or sonication. Lysed cells, including the soluble and insoluble materials therefrom, form a cell lysate. The present invention includes methods for making an antibody or antigen-binding fragment thereof lacking sulfated tyrosine variant or for purifying an antibody or antigen-binding fragment thereof to remove the sulfated tyrosine variants by a method including cell lysis and AEX chromatography in flow-through mode.

In an embodiment of the invention, antibodies or antigen-binding fragments are purified by methods including centrifugation. Centrifugation of a cell lysate or other suspension removes most particulate matter, such as cell debris, from the aqueous fraction containing the antibody or fragment. For example, in an embodiment of the invention, centrifugation is performed (e.g., on a cell lysate including discarding the lysate solid fraction of the lysate) at about 40,000 to 50,000× g for 15-30 minutes. In an embodiment of the invention, cells are removed from a liquid cell culture medium by centrifugation. For example, centrifugation using a gravitational force within a range of about 8,000× g to about 15,000× g (e.g., about 8000, 9000, 10000, 11000, 12000, 13000, 14000 or 15000), e.g., characterized by a Q/SIGMA ratio ranging between about $0.9×10^{-6}$ and $2.8×10^9$. In an embodiment of the invention, the liquid concentrate is depth filtered (e.g., with a pore size of 0.1 to about 0.2 μm). The present invention includes methods for making an antibody or antigen-binding fragment thereof lacking sulfated tyrosine variant or for purifying an antibody or antigen-binding fragment thereof to remove the sulfated tyrosine variants by a method including centrifugation and AEX chromatography in flow-through mode.

In an embodiment of the invention, immunoglobulin heavy and light chains are expressed in the host cell fused to a secretion signal sequence and secreted from the host cells into the culture medium of the host cells.

In an embodiment of the invention, antibodies or antigen-binding fragments are purified by filtration (e.g., before or after AEX chromatographic purification). For example, in an embodiment of the invention, an aqueous composition comprising the antibody or antigen-binding fragment is filtered to remove solid particulate material, e.g., through a filter having a pore size of about 1 μm, 0.45 μm or 0.22 μm. In an embodiment of the invention, the filter is made of cellulose acetate or polyvinylidene fluoride (PVDF). The present invention includes methods for making an antibody or antigen-binding fragment thereof lacking sulfated tyrosine variant or for purifying an antibody or antigen-binding fragment thereof to remove the sulfated tyrosine variants by a method including AEX chromatography in flow-through mode and filtration.

In an embodiment of the invention, antibodies or antigen-binding fragments are purified by fractional precipitation. Increased salt concentration can enhance hydrophobic interaction between proteins and result in a selective precipitation. In an embodiment of the invention, an aqueous composition comprising the antibody or fragment is precipitated in the presence of ammonium sulfate, dextran sulfate, polyvinylpyrrolidine, polyethylene glycol (PEG; e.g., PEG4000), acetone, polyethyleneimine, protamine sulfate, streptomycin sulfate, or caprylic acid. The present invention includes methods for making an antibody or antigen-binding fragment thereof lacking sulfated tyrosine variant or for purifying an antibody or antigen-binding fragment thereof to remove the sulfated tyrosine variants by a method including AEX chromatography in flow-through mode and fractional precipitation.

In an embodiment of the invention, a host cell, in which an immunoglobulin chain is expressed, is a mammalian cell, such as a Chinese hamster ovary (CHO) cell, a mouse myeloma cell, a PER cell, a hybridoma cell or a fungal or yeast cell, e.g., *Pichia* such as *Pichia pastoris* or *Saccharomyces cerevisiae*. In an embodiment of the invention, the host cell, e.g., CHO cell, lacks glutamine synthase.

In an embodiment of the invention, the polynucleotide(s) encoding the immunoglobulin heavy and/or light chain is/are operably linked to one or more expression control sequences such as a promoter. For example, the immunoglobulin is in an expression vector. To achieve high levels of antibody or antigen-binding fragment expression, a strong promoter/enhancer such as the cytomegalovirus (CMV) promoter and/or elongation factor alpha (EF1α) promoter can be used to drive immunoglobulin heavy chain and/or light chain expression.

In an embodiment of the invention, an intron sequence in the 5' untranslated region is included after the promoter/enhancer to increase export of transcribed mRNA to the cytoplasm from the nucleus, and one or more 3' polyadenylation signal sequences are included to maximize mRNA levels. In an embodiment of the invention, a polyadenylation signal sequence is the SV40 late or early polyadenylation signal sequence or the bovine growth hormone polyadenylation sequence. In an embodiment of the invention, a consensus Kozak sequence is created by placing GCC GCC(A/G)CC (SEQ ID NO: 69) immediately in front of the first translation initiation codon to enhance translation initiation. In an embodiment of the invention, a signal peptide sequence is placed immediately in front of an immunoglobulin chain to direct antibody or fragment secretion.

The conditions of cell culture can be monitored and adjusted as needed. For example, conditions such as pH, cell count, cell viability and temperature can be monitored and adjusted. In an embodiment of the invention, the temperature of a cell culture is adjusted, e.g., from 37° C. to 30-35° C. at 48 hours post-inoculation. Dissolved oxygen is, in an embodiment of the invention, monitored and/or adjusted to a set point such as 20-50%. In an embodiment of the invention, dissolved $CO_2$ is monitored and/or adjusted, e.g., to no greater than about 120-150 mm Hg. In an embodiment of the invention, osmolality is monitored and/or adjusted, e.g., to about 270-330 mOsm/kg.

Antibodies

The present invention provides compositions comprising antibodies and antigen-binding fragments thereof that lack detectable levels of sulfated tyrosine as well as methods for isolating compositions comprising such antibodies and fragments. For example, in an embodiment of the invention, the antibody or fragment comprises a sulfated tyrosine and binds to an antigen selected from: PD1, CD27, LAG3, CTLA4, BTLA, TIM3, ICOS, B7-H3, B7-H4, CD137, GITR, PD-L1, PD-L2, ILT1, ILT2 CEACAM1, CEACAM5, TIM3, TIGIT, VISTA, ILT3, ILT4, ILT5, ILT6, ILT7, ILT8, CD40, OX40, CD137, KIR2DL1, KIR2DL2, KIR2DL3, KIR2DL4, KIR2DL5A, KIR2DL5B, KIR3DL1, KIR3DL2, KIR3DL3, NKG2A, NKG2C, NKG2E, IL-10, IL-17 or TSLP.

The term "LAG3", with respect to the polypeptide to which antibodies and antigen-binding fragments of the present invention bind, refers to human and cynomolgous monkey, e.g., *Macaca fascicularis* or *Macaca* mulatta LAG3 as well as fragments thereof such as the mature fragment thereof lacking the signal peptide.

Examples of the immunoglobulin chains of anti-LAG3 antibodies (e.g., Ab1, Ab2, Ab3, Ab4, Ab5, Ab6, Ab7, Ab8 or Ab9 disclosed in WO2016028672) lacking tyrosine sulfation include those summarized below. For example, wherein the antibody or fragment comprises one or more of the CDRs and/or immunoglobulin chains set forth below. In an embodiment of the invention, the contaminant antibody or antigen-binding fragment comprises a CDR-L1 having the amino acid sequence KASQSLDYEGDSDMN (SEQ ID NO: 38) wherein the Y (bold and underscored) is sulfated.

In an embodiment of the invention, the anti-LAG3 antibody or antigen-binding fragment comprises the 4A10 heavy chain immunoglobulins and/or light chain immunoglobulins; $V_H$ and/or $V_L$ chains or the light chain CDRs and/or heavy chain CDRs (e.g., 4A10 CDR-L1, CDR-L2, CDR-L3, CDR-H1, CDR-H2 and CDR-H3).

In an embodiment of the invention, for any of Ab1, Ab2, Ab3, Ab4, Ab5, Ab6, Ab7, Ab8 or Ab9, any N-terminal heavy chain glutamine is converted to pyroglutamate and/or any C-terminal heavy chain lysine is removed.

-continued
TATATAAACTGGGTGAAGCAGAAGCCTGGACAGGGACTTGAGTGGATTGGA
TGGATTTATCCTGGAAGCGGTAATTCTATCTACAATGAGAACTTCAAGGCC 4A10- V<sub>H</sub> sequence
ATGAAATGCAGCTGGGTCATCTTCTTCCTGATGGCAGTGGTTATAGGAATCAATTCAGAGGTTCAGCTGCTCCAGTC

TGGGGCAGAACTTGTGAGGTCAGGGGCCTCAGTCAAGTTGTCCTGCACAGCCTCTGGCTTCAACATTGAAGACTACT

ATATGCACTGGATGAAACAGAGGCCTGAACAGGGCCTGGAGTGGATTGGATGGATTGATCCTGTGAATGGTGATACT

GAATATGCCCCGAAGTTCCAGGGCAAGGCCACTATGACTGCAGACACATCCTCCAACACAGCCTACCTACACCTCAA

CAGCCTGACATCTGAGGACACTGCCGTCTATTACTGTAATTTCTATGATGGTTACCTCTTTGCTTTCTGGGGCCAAG

GGACCCTGGTCACTGTCTCTGCA (SEQ ID NO: 1; wherein the CDRs are underscored and wherein the signal sequence is in bold font)

MKCSWVIFFLMAVVIGINSEVQLLQSGAELVRSGASVKLSCTASGFNIEDYYMHWMKQRPEQGLEWIGWIDPVNGDT

EYAPKFQGKATMTADTSSNTAYLHLNSLTSEDTAVYYCNFYDGYLFAFWGQGTLVTVSA (SEQ ID NO: 2; wherein the CDRs are underscored and wherein the signal sequence is in bold font)

CDR-H1: GFNIEDYYMH (SEQ ID NO: 3)

CDR-H2: WIDPVNGDTEYAPKFQG (SEQ ID NO: 4)

CDR-H3: YDGYLFAF (SEQ ID NO: 5)

4A10- V<sub>L</sub> sequence
ATGAGGTGCCTAGCTGAGTTCCTGGGGCTGCTTGTGCTCTGGATCCCTGGAGCCATTGGGGATATTGTGCTGACTCA

GGCTGCACCCTCTGTACCTGTCACTCCTGGAGAGTCAGTGTCCATCTCCTGCAGGTCTAGTAAGAGTCTCCTGCATA

GTGATGGCAACACTTATCTGTATTGGCTCCTGCAGAGGCCAGGCCAGTCTCCTCAGCTCCTGATATATCGGATGTCC

AACCTTGCCTCAGGGGTCCCAGACAGGTTCAGCGGCAGTGGGTCAGGAACTGTTTTCACACTGAGAATCAGCAGACT

GGAGGCTGAGGATGTGGGTATTTATTACTGTATGCAACATCTAGAATATCCTTTCACGTTTGGAGGGGGGACCAAGC

TGGAAATAAAA (SEQ ID NO: 6; wherein the CDRs are underscored and wherein the signal sequence is in bold font)

MRCLAEFLGLLVLWIPGAIGDIVLTQAAPSVPVTPGESVSISCRSSKSLLHSDGNTYLYWLLQRPGQSPQLLIYRMS

NLASGVPDRFSGSGSGTVFTLRISRLEAEDVGIYYCMQHLEYPFTFGGGTKLEIK (SEQ ID NO: 7; wherein the CDRs are underscored and wherein the signal sequence is in bold font)
CDR-L1: RSSKSLLHSDGNTYLY (SEQ ID NO: 8)

CDR-L2: YRMSNLAS (SEQ ID NO: 9)

CDR-L3: MQHLEYPFT (SEQ ID NO: 10)

In an embodiment of the invention, the anti-LAG3 antibody or antigen-binding fragment comprises the 19E8 heavy chain immunoglobulins and/or light chain immunoglobulins; V<sub>H</sub> and/or V<sub>L</sub> chains or the light chain CDRs and/or heavy chain CDRs (e.g., 19E8 CDR-L1, CDR-L2, CDR-L3, CDR-H1, CDR-H2 and CDR-H3):

19E8-V<sub>H</sub> sequence
ATGGGATGGAGCTGGATCTTTCTTTTCCTCCTGTCAGGAACTGCAGGTGTC

CGTTGCCAGATCCGACTGCAGCAGTCTGGACCTGAGCTGGTGAAGCCTGGG

GCTTCAGTGAAGATATCCTGCAAGGCTTCTGGGTCCTCCTTCACTGACTAC

-continued
AAGGCCACATTGACTGTAGACACATCCTCCAGCACAGCCTACATGCATCTC

AGCAGCCTGACATCTGAGGACACTGCTGTCTATTTCTGTGCAAGAGAGGCT

GATTACGACGATGCTTTGGACTACTGGGGTCAAGGAACCTCGGTCACCGTC

TCCTCA
(SEQ ID NO: 11; wherein the CDRs are underscored and wherein the signal sequence is in bold font)

MGWSWIFLFLLSGTAGVRCQIRLQQSGPELVKPGASVKISCKASGSSFTDY

YINWVKQKPGQGLEWIGWIYPGSGNSIYNENFKAKATLTVDTSSSTAYMHL

SSLTSEDTAVYFCAREADYDDALDYWGQGTSVTVSS
(SEQ ID NO: 12; wherein the CDRs are underscored
and wherein the signal sequence is in bold font)

CDR-H1: GSSFTDYYIN (SEQ ID NO: 13)

CDR-H2: WIYPGSGNSIYNENFKA (SEQ ID NO: 14)

CDR-H3: EADYDDALDY (SEQ ID NO: 15)

19E8-V$_L$ sequence
ATGGTATCCACACCTCAGTTCCTTGTATTTTTGCTTTTCTGGATTCCAGCC

TCCAGAGGTCACATCTTGCTGACTCAGTCTCCAGCCATTCTGTCTGTGAGT

CCAGGAGAAAGAGTCAGTTTCTCCTGC<u>AGGGCCAGTCAGAGCATTGGCACA</u>

<u>AGCATACACT</u>GGTATCAGCAAAGAACAAATGGTTCTCCAAGGCTTCTCATA

AAGTATGCTTCTGAGTCTATCTCTGGGATCCCTTCCAGGTTTAGTGGCAGT

GGATCAGGGACAGATTTTACTCTTAGCATCAACAGTGTGGAGTCAGAAGAT

ATTGCAGATTATTACTGT<u>CAACAAAGTAATAGCTGGCCAACGTACACGTTC</u>

GGAGGGGGGACCAAGCTGGAAATAAAA
(SEQ ID NO: 16; wherein the CDRs are underscored
and wherein the signal sequence is in bold font)

MVSTPQFLVFLLFWIPASRGHILLTQSPAILSVSPGERVSFSC<u>RASQSIGT</u>

<u>SIHWYQQRT</u>NGSPRLLIK<u>YASESIS</u>GIPSRFSGSGSGTDFTLSI<u>NS</u>VESED

IADYYC<u>QQSNS</u> <u>WPTYT</u>FGGGTKLEIK
(SEQ ID NO: 17; wherein the CDRs are underscored
and wherein the signal sequence is in bold font)

CDR-L1: RASQSIGTSIH (SEQ ID NO: 18)

CDR-L2: YASESIS (SEQ ID NO: 19)

CDR-L3: QQSNSWPTYT (SEQ ID NO: 20)

In an embodiment of the invention, the anti-LAG3 antibody or antigen-binding fragment comprises the 11C9 heavy chain immunoglobulins and/or light chain immunoglobulins; V$_H$ and/or V$_L$ chains or the light chain CDRs and/or heavy chain CDRs (e.g., 11C9 CDR-L1, CDR-L2, CDR-L3, CDR-H1, CDR-H2 and CDR-H3):

11C9-V$_H$ sequence
ATGAGATGGAGCTGTATCATCCTCTTCTTGGTAGCAACAGCTACAGGTGTC

AACTCCCAGGTCCAACTGCAGCAGCCTGGGGCTGAGCTTGTGATGCCTGGG

GCTTCAGCGAAGATGTCCTGCAAGGCTTCT<u>GGCTACACACTCACTGACTAC</u>

<u>TGGATGCAC</u>TGGGTGAAGCAGAGGCCTGGACAAGGCCTTGAGTGGATCGGA

<u>GCGATTGATATTTCTGATAGTTATTCTAGCTACAATCAAAAGTTCAAGGGC</u>

AAGGCCACATTGACTGTAGACGAATCCTCCAGCACAGCCTACATGCAGCTC

ACCAGCCTGACATCTGAGGACTCTGCGGTCTATTACTGTGCAAGAT<u>CCCCT</u>

<u>TTCTACAATAGTAGAGGGGGGAACTACTTTGACTACTGG</u>GGCCAAGGCACC

ACTCTCACAGTCTCCTCA
(SEQ ID NO: 21; wherein the CDRs are underscored
and wherein the signal sequence is in bold font)

MRWSCIILFLVATATGVNSQVQLQQPGAELV<u>MPGASAKM</u>SCKASG<u>YTLTDY</u>

<u>WMH</u>WVKQRPGQGLEWIG<u>AIDISDSYSSYNQKFKG</u>KATLTVDESSSTAYM<u>QL</u>

TSLTSEDSAVYYCARS<u>PFYNS</u>RGGNYFDYWGQGTTLTVSS
(SEQ ID NO: 22; wherein the CDRs are underscored
and wherein the signal sequence is in bold font)

CDR-H1: GYTLTDYWMH (SEQ ID NO: 23)

CDR-H2: AIDISDSYSSYNQKFKG (SEQ ID NO: 24)

CDR-H3: SPFYNSRGGNYFDY (SEQ ID NO: 25)

11C9-V$_L$ sequence
ATGATGTCCTCTGCTCAGTTCCTTGGTCTCCTGTTGCTCTGTTTTCAAGGT

ACCAGATGTGATATCCAGATGACACAGACTACATCCTCCCTGTCTGCCTCT

CTGGGAGACAGAGTCACCATCAGTTGC<u>AGGGCAAGTCAGGACATTAGCAAT</u>

<u>TATTTAAAC</u>TGGTATCAGCAGAAACCAGATGGAACTGTTAAACTCCTGATC

TAC<u>TACACATCAAGATTACACT</u>CAGGAGTCCCATCAAGGTTCAGTGGCAGT

GGGTCTGGAACAGATTATTCTCTCACCATTAGCAACCTGGAGCAAGAAGAT

ATTGCCACTTACTTTTGC<u>CAACAGGGTGATACGCTTCCTCCGTGGACG</u>TTC

GGTGGAGGCACCAAGCTGGAAATCAAA
(SEQ ID NO: 26; wherein the CDRs are underscored
and wherein the signal sequence is in bold font)

MMSSAQFLGLLLLCFQGTRCDIQMTQTTSSLSASLGDRVTISC<u>RASQDISN</u>

<u>YLN</u>WYQQKPDGTVKLLIY<u>YTSRLHS</u>GVPSRFSGSGSGTDYSLTISNLEQED

IATYFC<u>QQGDTLPPWT</u>FGGGTKLEIK
(SEQ ID NO: 27; wherein the CDRs are underscored
and wherein the signal sequence is in bold font)

CDR-L1: PASQDISNYLN (SEQ ID NO: 28)

CDR-L2: YTSRLHS (SEQ ID NO: 29)

CDR-L3: QQGDTLPPWT (SEQ ID NO: 30)

In an embodiment of the invention, the anti-LAG3 antibody or antigen-binding fragment comprises the 22D2 heavy chain immunoglobulins and/or light chain immunoglobulins; V$_H$ and/or V$_L$ chains or the light chain CDRs and/or heavy chain CDRs (e.g., 22D2 CDR-L1, CDR-L2, CDR-L3, CDR-H1, CDR-H2 and CDR-H3):

22D2- V$_H$ sequence
ATGGGATGGACCTGGATCTTTCTCTTCTTCCTGTCAGGAACTGCAGGTGTCCTCTCTGAGGTCCTGCTGCTACAGTC TGGACCTGAACTGGTGAAGCCTGGGACTTCAGTGAAAATCCCCTGCAAGGCTTCT<u>GGATACACATTCACTGACTACA</u>

<u>ACGTGGACTGGGT</u>GAAGCAGCGCCATGGAAAGGGCCTTGAGTGGATTGGA<u>GATATTAATCCAAACAATGGTGGTACT</u>

<u>ATCTACAGTCAGAAATTCAAGGGC</u>AAGGCCACATTGACTGTTGACAAGTCCTCCAGCACAGCCTTCATGGAGCTCCG

CAGCCTGACATCTGAGGACACTGCAGTCTATTTCTGTGCAAGG<u>AACTATAGGTGGTTTGGTGCTATGGACCACTGGG</u>

GTCAAGGAACCTCAGTCACCGTCTCCTCAGCCAAAACAACAGCCCCATCGGTCTATCCACTG (SEQ ID NO: 31; wherein the CDRs are underscored and wherein the signal sequence is in bold font)

MGWTWIFLFFLSGTAGVLSEVLLLQSGPELVKPGTSVKIPCKASGYTFT<u>DYNVD</u>WVKQRHGKGLEWIG<u>DINPN</u>

<u>NGG</u>TIYSQKFKGKATLTVDKSSSTAFMELRSLTSEDTAVYFCAR<u>NYRWFGAMDH</u>WGQGTSVTVSS (SEQ ID NO: 32; wherein the CDRs are underscored and wherein the signal sequence is in bold font)

CDR-H1: DYNVD (SEQ ID NO: 33)

CDR-H2: DINPNNGGTIYSQKFKG (SEQ ID NO: 34)

CDR-H3: NYRWFGAMDH (SEQ ID NO: 35)

22D2- $V_L$ sequence

ATGGAGACAGACACAATCCTGCTATGGGTGCTGCTGCTCTGGGTTCCAGGTTCCACTGGTGACATTGTGTTGACCCA

ATCTCCAGCTTCTTTGGCTGTGTCTCCAGGGCAGAGGGCCACCATTTCCTGC<u>AAGGCCAGTCAAAGTCTTGATTATG</u>

<u>AAGGTGATAGTGATATGAAT</u>TGGTACCAACAGAAACCAGGACAGCCACCCAGACTCCTCATCTCT<u>GGTGCATCCAAT</u>

<u>CTAGAGTCT</u>GGGATCCCAGCCAGGTTCAGTGGCAGTGGGTCTGGGACAGACTTCACTGTTAACATCCATCCTGTGGA

GGAGGAGGATGCTGCAACCTATTACTGT<u>CAGCAAAGTACTGAGGATCCTCGGACG</u>TTCGGTGGAGGCACCAAGCTGG

AAATCAAACGGGCTGATGCTGCACCAACTGTATCCATCTTCCCACCATCCAGTGAGCAGTTAACATCTGGAGGTGCC

TCAGTCGTGTGCTTCTTGAACAACTTCTACCCCAAAGACATCAATGTCAAGTGGAAGATTGATGGCAGTGAACGACA

AAATGGCG (SEQ ID NO: 36; wherein the CDRs are underscored and wherein the signal sequence is in bold font)

METDTILLWVLLLWVPGSTGDIVLTQSPASLAVSPGQRATISC<u>KASQSLDYEGDSDMN</u>WYQQKPGQPPRLLIS<u>GASN</u>

<u>LES</u>GIPARFSGSGSGTDFTVNIHPVEEEDAATYYC<u>QQSTEDPRT</u>FGGGTKLEIK (SEQ ID NO: 37; wherein the CDRs are underscored and wherein the signal sequence is in bold font)

CDR-L1: KASQSLD<u>Y</u>EGDSDMN (SEQ ID NO: 38)

CDR-L2: GASNLES (SEQ ID NO: 39)

CDR-L3: QQSTEDPRT (SEQ ID NO: 40).

In an embodiment of the invention, the anti-LAG3 antibody or antigen-binding fragment comprises the Ab1, Ab2, Ab3, Ab4, Ab5, Ab6, Ab7, Ab8 or Ab9 heavy chain immunoglobulins and/or light chain immunoglobulins; $V_H$ and/or $V_L$ chains or the light chain CDRs and/or heavy chain CDRs (e.g., Ab1, Ab2, Ab3, Ab4, Ab5, Ab6, Ab7, Ab8 or Ab9 CDR-L1, CDR-L2, CDR-L3, CDR-H1, CDR-H2 and CDR-H3):

Ab1: humanized light chain 45AGX Humanized×[LAG3_H] mAb (LB145.22D2.E1.D1 (VL3)) Kappa (PX) (or the variable domain thereof) and humanized heavy chain 53AHH Humanized×[LAG3_H] mAb (LB145.22D2.E1.D1 VH6) IgG1/Kappa (PX) (or the variable domain thereof); for example comprising:

```
a light chain immunoglobulin comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC (SEQ ID NO: 41);
and a heavy chain immunoglobulin comprising the amino acid sequence:
QMQLVQSGPEVKKPGTSVKVSCKASGYTFTDYNVDWVRQARGQRLEWIGDINPNNGGTIYAQKFQERVTITVDKSTS

TAYMELSSLRSEDTAVYYCARNYRWFGAMDHWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEVHNAKTKPREEQYNSTYRVVSVL
```

```
TVLHQDWLNGKEYKCKVSNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSLSPGK (SEQ ID NO: 42);
or a light chain immunoglobulin variable domain comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIK (amino acids 1-111 of SEQ ID NO: 41 (CDRs underscored));
and a heavy chain immunoglobulin variable domain comprising the amino acid sequence:
QMQLVQSGPEVKKPGTSVKVSCKASGYTFTDYNVDWVRQARGQRLEWIGDINPNNGGTIYAQKFQERVTITVDKSTS

TAYMELSSLRSEDTAVYYCARNYRWFGAMDHWGQGTTVTVS S (amino acids 1-119 of SEQ ID NO: 42 (CDRs underscored));
or comprising the CDRs:
CDR-L1: KASQSLDYEGDSDMN (SEQ ID NO: 38);

CDR-L2: GASNLES (SEQ ID NO: 39);

CDR-L3: QQSTEDPRT (SEQ ID NO: 40);

CDR-H1: DYNVD (SEQ ID NO: 33);

CDR-H2: DINPNNGGTIYAQKFQE (SEQ ID NO: 59);
and

CDR-H3: NYRWFGAMDH (SEQ ID NO: 35)
```

Ab2: humanized light chain 45AGX Humanized×[LAG3_H] mAb (LB145.22D2.E1.D1 (VL3)) Kappa (PX) (or the variable domain thereof) and humanized heavy chain 56AHH Humanized×[LAG3_H] mAb (LB145.22D2.E1.D1 VH6 N55S) IgG1/Kappa (PX) (or the variable domain thereof); for example: comprising:

```
a light chain immunoglobulin comprising the amino acid sequence:

DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC (SEQ ID NO: 43);
and a heavy chain immunoglobulin comprising the amino acid sequence:
QMQLVQSGPEVKKPGTSVKVSCKASGYTFTDYNVDWVRQARGQRLEWIGDINPNSGGTIYAQKFQERVTITVDKSTS

TAYMELSSLRSEDTAVYYCARNYRWFGAMDHWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSLSPGK (SEQ ID NO: 44);
or a light chain immunoglobulin variable domain comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIK (amino acids 1-111 of SEQ ID NO: 43 (CDRs underscored));
and a heavy chain immunoglobulin variable domain comprising the amino acid sequence:
```

-continued

```
QMQLVQSGPEVKKPGTSVKVSCKASGYTFTDYNVDWVRQARGQRLEWIGDINPNSGGTIYAQKFQERVTITVDKSTS

TAYMELSSLRSEDTAVYYCARNYRWFGAMDHWGQGTTVTVS S
```

(amino acids 1-119 of SEQ ID NO: 44 (CDRs underscored));
or comprising the CDRs:
CDR-L1: KASQSLDYEGDSDMN (SEQ ID NO: 38);

CDR-L2: GASNLES (SEQ ID NO: 39);

CDR-L3: QQSTEDPRT (SEQ ID NO: 40);

CDR-H1: DYNVD (SEQ ID NO: 33);

CDR-H2: DINPNSGGTIYAQKFQE (SEQ ID NO: 60);
and

CDR-H3: NYRWFGAMDH (SEQ ID NO: 35)

Ab3: humanized light chain 45AGX Humanized×[LAG3_H] mAb (LB145.22D2.E1.D1 (VL3)) Kappa (PX) (or the variable domain thereof) and humanized heavy chain 54AHH Humanized×[LAG3_H] mAb (LB145.22D2.E1.D1 VH6 N55D) IgG1/Kappa (PX) (or the variable domain thereof); for example comprising:

```
a light chain immunoglobulin comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC (SEQ ID NO: 45)

a heavy chain immunoglobulin comprising the amino acid sequence:
QMQLVQSGPEVKKPGTSVKVSCKASGYTFTDYNVDWVRQARGQRLEWIGDINPNDGGTIYAQKFQERVTITVDKSTS

TAYMELSSLRSEDTAVYYCARNYRWFGAMDHWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSLSPGK (SEQ ID NO: 46);
or a light chain immunoglobulin variable domain comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIK (amino acids 1-111 of SEQ ID NO: 45 (CDRs underscored));
and a heavy chain immunoglobulin variable domain comprising the amino acid sequence:
QMQLVQSGPEVKKPGTSVKVSCKASGYTFTDYNVDWVRQARGQRLEWIGDINPNDGGTIYAQKFQERVTITVDKSTS

TAYMELSSLRSEDTAVYYCARNYRWFGAMDHWGQGTTVTVSS (amino acids 1-119 of SEQ ID NO: 46 (CDRs underscored));
or
``` comprising the CDRs:
CDR-L1: KASQSLDYEGDSDMN (SEQ ID NO: 38);

CDR-L2: GASNLES (SEQ ID NO: 39);

CDR-L3: QQSTEDPRT (SEQ ID NO: 40);

-continued

CDR-H1: DYNVD (SEQ ID NO: 33);

CDR-H2: DINPNDGGTIYAQKFQE (SEQ ID NO: 61);
and

CDR-H3: NYRWFGAMDH (SEQ ID NO: 35)

Ab4: humanized light chain 45AGX Humanized×[LAG3_H] mAb (LB145.22D2.E1.D1 (VL3)) Kappa (PX) (or the variable domain thereof) and humanized heavy chain 52AHH Humanized×[LAG3_H] mAb (LB145.22D2.E1.D1 VH6 N55Q) IgG1/Kappa (PX) (or the variable domain thereof); for example comprising:

a lilght chain immunoglobulin comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC (SEQ ID NO: 47);
and a heavy chain immunoglobulin comprising the amino acid sequence:
QMQLVQSGPEVKKPGTSVKVSCKASGYTFTDYNVDWVRQARGQRLEWIGDINPNQGGTIYAQKFQERVTITVDKSTS

TAYMELSSLRSEDTAVYYCARNYRWFGAMDHWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSLSPGK (SEQ ID NO: 48);
or a light chain immunoglobulin variable domain comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIK (amino acids 1-111 of SEQ ID NO: 47 (CDRs underscored));
and a heavy chain immunoglobulin variable domain comprising the amino acid sequence:
QMQLVQSGPEVKKPGTSVKVSCKASGYTFTDYNVDWVRQARGQRLEWIGDINPNQGGTIYAQKFQERVTITVDKSTS

TAYMELSSLRSEDTAVYYCARNYRWFGAMDHWGQGTTVTVSS (amino acids 1-119 of SEQ ID NO: 48 (CDRs underscored));
or comprising the CDRs:
CDR-L1: KASQSLDYEGDSDMN (SEQ ID NO: 38);

CDR-L2: GASNLES (SEQ ID NO: 39);

CDR-L3: QQSTEDPRT (SEQ ID NO: 40);

CDR-H1: DYNVD (SEQ ID NO: 33);

CDR-H2: DINPNQGGTIYAQKFQE (SEQ ID NO: 62);
and

CDR-H3: NYRWFGAMDH (SEQ ID NO: 35)

Ab5: humanized light chain 45AGX Humanized×[LAG3_H] mAb (LB145.22D2.E1.D1 (VL3)) Kappa (PX) (or the variable domain thereof) and humanized heavy chain 57AHH Humanized×[LAG3_H] mAb (LB145.22D2.E1.D1 VH6) IgG4 S228P (PX) (or the variable domain thereof); for example comprising:

```
a light chain immunoglobulin comprising the amino acid sequence:
DIVMTQTPLSLSVTPGQPASISCKASQSLDYEGD DMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC (SEQ ID NO: 49);
and

QMQLVQSGPEVKKPGTSVKVSCKASGYTFTDYNVDWVRQARGQRLEWIGDINPNNGGTIYAQKFQERVTITVDKSTS

TAYMELSSLRSEDTAVYYCARNYRWFGAMDHWGQGTTVTVSSASTKGPSVFPLAPCSRSTSESTAALGCLVKDYFPE

PVTVSWNSGALTSGVHTFPAVLQSSGLYSLSSVVTVPSSSLGTKTYTCNVDHKPSNTKVDKRVESKYGPPCPPCPAP

EFLGGPSVFLFPPKPKDTLMISRTPEVTCVVVDVSQEDPEVQFNWYVDGVEVHNAKTKPREEQFN STYRVVSVLTVL

HQDWLNGKEYKCKVSNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLGK (SEQ ID NO: 50);
or a light chain immunoglobulin variable domain comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIK (amino acids 1-111 of SEQ ID NO: 49 (CDRs underscored));
and a heavy chain immunoglobulin variable domain comprising the amino acid sequence:
QMQLVQSGPEVKKPGTSVKVSCKASGYTFTDYNVDWVRQARGQRLEWIGDINPNNGGTIYAQKFQERVTITVDKSTS

TAYMELSSLRSEDTAVYYCARNYRWFGAMDHWGQGTTVTVSS (amino acids 1-119 of SEQ ID NO: 50 (CDRs underscored));
or
comprising the CDRs:
CDR-L1: KASQSLDYEGDSDMN (SEQ ID NO: 38);

CDR-L2: GASNLES (SEQ ID NO: 39);

CDR-L3: QQSTEDPRT (SEQ ID NO: 40);

CDR-H1: DYNVD (SEQ ID NO: 33);

CDR-H2: DINPNNGGTIYAQKFQE (SEQ ID NO: 59);
and

CDR-H3: NYRWFGAMDH (SEQ ID NO: 35)
```

Ab6: humanized light chain 45AGX Humanized×[LAG3_H] mAb (LB145.22D2.E1.D1 (VL3)) Kappa (PX) (or the variable domain thereof) and humanized heavy chain 73AHD Humanized×[LAG3_H] mAb (LB145.22D2.E1.D1 VH6 N55D/VL3) IgG4 S228P/Kappa (PX) (or the variable domain thereof); for example comprising:

```
a light chain immunoglobulin comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC (SEQ ID NO: 51);
and
```

-continued a heavy chain immunoglobulin comprising the amino acid sequence:
QMQLVQSGPEVKKPGTSVKVSCKASGYTFTDYNVDWVRQARGQRLEWIGDINPNDGGTIYAQKFQERVTITVDKSTS

TAYMELSSLRSEDTAVYYCARNYRWFGAMDHWGQGTTVTVSSASTKGPSVFPLAPCSRSTSESTAALGCLVKDYFPE

PVTVSWNSGALTSGVHTFPAVLQSSGLYSLSSVVTVPSSSLGTKTYTCNVDHKPSNTKVDKRVESKYGPPCPPCPAP

EFLGGPSVFLFPPKPKDTLMISRTPEVTCVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLGK (SEQ ID NO: 52);
or a light chain immunoglobulin variable domain comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIK (amino acids 1-111 of SEQ ID NO: 51 (CDRs underscored));
and a heavy chain immunoglobulin variable domain comprising the amino acid sequence:
QMQLVQSGPEVKKPGTSVKVSCKASGYTFTDYNVDWVRQARGQRLEWIGDINPNDGGTIYAQKFQERVTITVDKSTS

TAYMELSSLRSEDTAVYYCARNYRWFGAMDHWGQGTTVTVSS (amino acids 1-119 of SEQ ID NO: 52 (CDRs underscored));
or comprising the CDRs:
CDR-L1: KASQSLDYEGDSDMN (SEQ ID NO: 38);

CDR-L2: GASNLES (SEQ ID NO: 39);

CDR-L3: QQSTEDPRT (SEQ ID NO: 40);

CDR-H1: DYNVD (SEQ ID NO: 33);

CDR-H2: DINPNDGGTIYAQKFQE (SEQ ID NO: 61);
and

CDR-H3: NYRWFGAMDH (SEQ ID NO: 35)

Ab7: humanized light chain 45AGX Humanizedx [LAG3_H] mAb (LB145.22D2.E1.D1 (VL3)) Kappa (PX) (or the variable domain thereof) and humanized heavy chain 21AHG Humanizedx[LAG3_H] mAb (LB145.22D2.E1.D1 VH6 N55S/VL3) IgG4 S228P/ Kappa (PX) (or the variable domain thereof); for example comprising:

a light chain immunoglobulin comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC (SEQ ID NO: 53);
and a heavy chain immunoglobulin comprising the amino acid sequence:
QMQLVQSGPEVKKPGTSVKVSCKASGYTFTDYNVDWVRQARGQRLEWIGDINPNSGGTIYAQKFQERVTITVDKSTS

TAYMELSSLRSEDTAVYYCARNYRWFGAMDHWGQGTTVTVSSASTKGPSVFPLAPCSRSTSESTAALGCLVKDYFPE

PVTVSWNSGALTSGVHTFPAVLQSSGLYSLSSVVTVPSSSLGTKTYTCNVDHKPSNTKVDKRVESKYGPPCPPCPAP

EFLGGPSVFLFPPKPKDTLMISRTPEVTCVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLGK

```
(SEQ ID NO: 54);
or a light chain immunoglobulin variable domain comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIK (amino acids 1-111 of SEQ ID NO: 53 (CDRs underscored));
and a heavy chain immunoglobulin variable domain comprising the amino acid sequence:
QMQLVQSGPEVKKPGTSVKVSCKASGYTFTDYNVDWVRQARGQRLEWIGDINPNSGGTIYAQKFQERVTITVDKSTS

TAYMELSSLRSEDTAVYYCARNYRWFGAMDHWGQGTTVTVSS (amino acids 1-119 of SEQ ID NO: 54 (CDRs underscored));
or comprising the CDRs:
CDR-L1: KASQSLDYEGDSDMN (SEQ ID NO: 38);

CDR-L2: GASNLES (SEQ ID NO: 39);

CDR-L3: QQSTEDPRT (SEQ ID NO: 40);

CDR-H1: DYNVD (SEQ ID NO: 33);

CDR-H2: DINPNSGGTIYAQKFQE (SEQ ID NO: 60);
and

CDR-H3: NYRWFGAMDH (SEQ ID NO: 35)
```

Ab8: humanized light chain 45AGX Humanized× [LAG3_H] mAb (LB145.22D2.E1.D1 (VL3)) Kappa (PX) (or the variable domain thereof) and humanized heavy chain 80AHG Humanized×[LAG3_H] mAb (LB145.22D2.E1.D1 VH6 N55Q/VL3) IgG4 S228P/ Kappa (PX) (or the variable domain thereof); for example comprising:

```
a light chain immunoglobulin comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC (SEQ ID NO: 55);
and a heavy chain immunoglobulin comprising the amino acid sequence:
QMQLVQSGPEVKKPGTSVKVSCKASGYTFTDYNVDWVRQARGQRLEWIGDINPNQGGTIYAQKFQERVTITVDKSTS

TAYMELSSLRSEDTAVYYCARNYRWFGAMDHWGQGTTVTVSSASTKGPSVFPLAPCSRSTSESTAALGCLVKDYFPE

PVTVSWNSGALTSGVHTFPAVLQSSGLYSLSSVVTVPSSSLGTKTYTCNVDHKPSNTKVDKRVESKYGPPCPPCPAP

EFLGGPSVFLFPPKPKDTLMISRTPEVTCVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLGK (SEQ ID NO: 56);
or a light chain immunoglobulin variable domain comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIK (amino acids 1-111 of SEQ ID NO: 55 (CDRs underscored));
and a heavy chain immunoglobulin variable domain comprising the amino acid sequence:
QMQLVQSGPEVKKPGTSVKVSCKASGYTFTDYNVDWVRQARGQRLEWIGDINPNQGGTIYAQKFQERVTITVDKSTS
```

TAYMELSSLRSEDTAVYYCARNYRWFGAMDHWGQGTTVTVS S (amino acids 1-119 of SEQ ID NO: 56 (CDRs underscored));
or comprising the CDRs:
CDR-L1: KASQSLDYEGDSDMN (SEQ ID NO: 38);

CDR-L2: GASNLES (SEQ ID NO: 39);

CDR-L3: QQSTEDPRT (SEQ ID NO: 40);

CDR-H1: DYNVD (SEQ ID NO: 33);

CDR-H2: DINPNQGGTIYAQKFQE (SEQ ID NO: 62);
and

CDR-H3: NYRWFGAMDH (SEQ ID NO: 35)

or

Ab9: humanized light chain 45AGX Humanizedx [LAG3_H] mAb (LB145.22D2.E1.D1 (VL3)) Kappa (PX) (or the variable domain thereof) and humanized heavy chain 72AHD Humanizedx [LAG3_H] mAb (LB145.22D2.E1.D1 VH6 N55G/VL3) IgG4 S228P/Kappa (PX)) (or the variable domain thereof); for example comprising:

a light chain immunoglobulin comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC (SEQ ID NO: 57);
and a heavy chain immunoglobulin comprising the amino acid sequence:
QMQLVQSGPEVKKPGTSVKVSCKASGYTFTDYNVDWVRQARGQRLEWIGDINPNGGGTIYAQKFQERVTITVDKSTS

TAYMELSSLRSEDTAVYYCARNYRWFGAMDHWGQGTTVTVSSASTKGPSVFPLAPCSRSTSESTAALGCLVKDYFPE

PVTVSWNSGALTSGVHTFPAVLQSSGLYSLSSVVTVPSSSLGTKTYTCNVDHKPSNTKVDKRVESKYGPPCPPCPAP

EFLGGPSVFLFPPKPKDTLMISRTPEVTCVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLGK (SEQ ID NO: 58);
or a light chain immunoglobulin variable domain comprising the amino acid sequence:
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIK (amino acids 1-111 of SEQ ID NO: 57 (CDRs underscored));
and a heavy chain immunodlobulin variable domain comprising the amino acid sequence:
QMQLVQSGPEVKKPGTSVKVSCKASGYTFTDYNVDWVRQARGQRLEWIGDINPNGGGTIYAQKFQERVTITVDKSTS

TAYMELSSLRSEDTAVYYCARNYRWFGAMDHWGQGTTVTVSS (amino acids 1-119 of SEQ ID NO: 58 (CDRs underscored));
or comprising the CDRs:
CDR-L1: KASQSLDYEGDSDMN (SEQ ID NO: 38);

CDR-L2: GASNLES (SEQ ID NO: 39);

CDR-L3: QQSTEDPRT (SEQ ID NO: 40);

CDR-H1: DYNVD (SEQ ID NO: 33);

-continued

CDR-H2: DINPNGGGTIYAQKFQE (SEQ ID NO: 63);
and

CDR-H3: NYRWFGAMDH (SEQ ID NO: 35)

In an embodiment of the invention, the CDR-H2 of any anti-LAG3 antibody or antigen-binding fragment thereof of the present invention comprises the amino acid sequence:

DINPNX$_1$GGTIYX$_2$QKFX$_3$X$_4$ (SEQ ID NO: 64)

wherein,
D, N, S or Q
X$_2$=A or S
X$_3$=Q or K
X$_4$=E or G

The present invention includes antibodies and antigen-binding fragments thereof (e.g., 4A10, 19E8, 11C9 and/or 22D2; e.g., Ab1, Ab2, Ab3, Ab4, Ab5, Ab6, Ab7, Ab8 and/or Ab9) comprising N-linked glycans that are typically added to immunoglobulins produced in Chinese hamster ovary cells (CHO N-linked glycans) or to engineered yeast cells (engineered yeast N-linked glycans), such as, for example, *Pichia pastoris*. For example, in an embodiment of the invention, the antibody or antigen-binding fragment comprises one or more of the "engineered yeast N-linked glycans" or "CHO N-linked glycans" that are set forth in FIG. 11 (e.g., G0 and/or G0-F and/or G1 and/or G1-F and/or G2-F and/or Man5). In an embodiment of the invention, the antibody or antigen-binding fragment comprises the engineered yeast N-linked glycans, i.e., G0 and/or G1 and/or G2, optionally, further including Man5. In an embodiment of the invention, the antibody or antigen-binding fragment comprise the CHO N-linked glycans, i.e., G0-F, G1-F and G2-F, optionally, further including G0 and/or G1 and/or G2 and/or Man5. In an embodiment of the invention, about 80% to about 95% (e.g., about 80-90%, about 85%, about 90% or about 95%) of all N-linked glycans on the antibody or antigen-binding fragment immunoglobulin chains are engineered yeast N-linked glycans or CHO N-linked glycans. See Nett et al. Yeast. 28(3): 237-252 (2011); Hamilton et al. Science. 313(5792): 1441-1443 (2006); Hamilton et al. Curr Opin Biotechnol. 18(5): 387-392 (2007). For example, in an embodiment of the invention, an engineered yeast cell is GFI5.0 or YGLY8316 or strains set forth in U.S. Pat. No. 7,795,002 or Zha et al. Methods Mol Biol. 988:31-43 (2013). See also international patent application publication no. WO2013/066765.

Tyrosine sulfation variants of anti-LAG3 antibodies (e.g., Ab1, Ab2, Ab3, Ab4, Ab5, Ab6, Ab7, Ab8 and/or Ab9) comprise molecular weights of about 148670 Da, 148832 Da and/or 148994 Da. Variants lacking the tyrosine sulfation comprise molecular weights of about 148590 Da, 148752 Da and/or 148914 Da.

"Isolated" antibodies or antigen-binding fragments thereof are at least partially free of other biological molecules from the cells or cell culture from which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

An antigen-binding fragment of an antibody is a portion of an antibody that retains the ability to bind specifically to the antigen bound by the full-length antibody. Examples of antigen-binding fragments include, but are not limited to, Fab, Fab', F(ab')2, and Fv fragments; diabodies; single-chain antibody molecules, e.g., sc-Fv; nanobodies and multispecific antibodies formed from antibody fragments.

In general, the basic antibody structural unit comprises a tetramer. Each tetramer includes two identical pairs of polypeptide chains, each pair having one "light" and one "heavy" chain. See generally, Fundamental Immunology Ch. 7 (Paul, W., ed., 2nd ed. Raven Press, N.Y. (1989).

Monoclonal antibodies are substantially homogeneous antibodies, i.e., the antibody molecules comprising the population are identical in amino acid sequence except for possible naturally occurring mutations that may be present in minor amounts. See Kohler et al. (1975) Nature 256: 495; U.S. Pat. No. 4,816,567; Clackson et al. (1991) Nature 352: 624-628; Marks et al. (1991) J. Mol. Biol. 222: 581-597; and Presta (2005) J. Allergy Clin. Immunol. 116:731.

A chimeric antibody is an antibody having the variable domain from a first antibody and the constant domain from a second antibody, where the first and second antibodies are from different species. (U.S. Pat. No. 4,816,567; and Morrison et al., (1984) Proc. Natl. Acad. Sci. USA 81: 6851-6855). Typically, the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental (e.g., mouse) antibody.

A humanized antibody contains sequences from both human and non-human (e.g., mouse or rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

Immunoglobulins may be assigned to different classes depending on the amino acid sequences of the constant domain of their heavy chains. There are at least five major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The invention comprises antibodies and antigen-binding fragments (e.g., anti-LAG3) of any of these classes or subclasses of antibodies.

In one embodiment, the antibody or antigen-binding fragment (e.g., anti-LAG3) comprises a heavy chain constant region, e.g. a human constant region, such as γ1, γ2, γ3, or γ4 human heavy chain constant region or a variant thereof. In another embodiment, the antibody or antigen-binding fragment (e.g., anti-LAG3) comprises a light chain constant region, e.g. a human light chain constant region, such as lambda or kappa human light chain region or variant thereof. By way of example, and not limitation, the human heavy chain constant region can be γ4 and the human light chain constant region can be kappa. In an alternative embodiment, the Fc region of the antibody is γ4 with a Ser228Pro mutation (Schuurman, J et. al., Mol. Immunol. 38: 1-8, 2001).

EXAMPLES

These examples illustrate the present invention and are not intended to be limiting thereto.

Example 1

Identification Of Antibody Tyrosine Sulfation Variants And Purification Methods In this example, the presence of tyrosine sulfation antibody variants of Ab6 were identified and a purification method for removing the variants was developed.

Materials and Methods

Alkaline phosphatase was available from New England Biolabs (Ipswich, Mass.). Anti-tyrosine sulfation antibody was available from Millipore (Billerica, Mass.). Synthetic peptide was purchased from AnaSpec (Fremont, Calif.).
Anion Exchange (AEX) Chromatography AEX chromatography was performed using POROS™ GoPure D™ Pre-packed Column, 0.5×5 cm, 1 mL in a flow through mode by using a GE Akta Avant™ system. The protein-A chromatography purified mAb was pH adjusted to pH 6.5 with 1M Tris and was loaded on the column. Prior to protein loading, the column was equilibrated with 25 mM sodium phosphate pH 6.5, post loading the column was washed with 25 mM sodium phosphate pH 6.5 and striped with 1M NaCl. The absorbance at 280 nm was monitored for the duration of the run. Fractions, pool and strip, and AEX load were collected and analyzed.
Ion Exchange HPLC Ion exchange HPLC was performed on a MabPac™ SCX-10 column (4×250 mm, 3.14 ml) at ambient temperature by using an Agilent 1600 series system. Mobile phase B was 30 mM sodium phosphate pH 8.0 and mobile A was 25 mM MES, pH 5.8. The column was first equilibrated at 14% mobile phase B at a flow rate of 1.0 mL/min for 10 min. The mAb protein was then eluted from the column using a gradient of mobile phase B (14% to 80% in 18 min). The column was then cleaned with 100% mobile B for 3 min and re-equilibrated at 14% mobile phase B for the next sample analysis. The absorbance at 280 nm of the eluate was monitored throughout the LC run.
Intact and Reduced LC/MS 20 μg of sample was diluted to 0.5 mg/mL with 50 mM Tris buffer pH 8.0. The RP-HPLC separation was performed using Waters™ Acquity UPLC® H-Class. The column used was Acquity UPLC BEH300 C4, 1.7 μm, 1.0×100 mm (Waters™, Milford, Mass.; —O—(Si)(CH$_3$)$_2$—C$_4$H$_9$ ligand). Mobile phases were 0.1% formic acid (FA) in water as mobile A and 0.1% FA in acetonitrile (ACN) as mobile B. The LC flow rate was 0.08 mL/min and the column temperature was maintained at 80° C. The antibody was eluted using a gradient of 4-15 min of 30%-90% B. MS spectra were acquired on a Waters™ Xevo® G2 Q-TOF system which was scanned in a range of m/z 800-4000.

20 μg of sample was diluted by a reducing buffer (50 mM Tris pH 8.0, containing 6 M Guanidine HCl) to a final volume of 100 μL. Two microliters of 1M dithiothreitol (DTT) (Sigma-Aldrich, St. Louis, Mo.) solution was added to each of the samples followed by incubation at 56° C. for 20 minutes. The RP-UPLC separation was performed on a Waters™ Acquity UPLC® H-Class. The column used was Acquity UPLC, BEH300 C4, 2.1×100 mm, 1.7 um (Waters™). MS spectra were acquired on a Waters™ Xevo® G2 Q-TOF system which was scanned in a range of m/z 600-3000. MS data was analyzed by MaxEnt1 of MassLynx 4.1.
Peptide Mapping LC/MS 100 μg of a sample was buffer exchanged to 100 uL denaturing buffer containing 50 mM Tris pH 8.0, 6 M Guanidine HCl and 5 mM EDTA. The reducing reactions were conducted at 56° C. for 30 minutes with 20 mM DTT in the solution. The samples were alkylated with 50 mM iodoacetamide at room temperature for 30 minutes in dark. The alkylation reaction was terminated by adding 1 μL of a 500 mM DTT solution. The reduced and alkylated samples were diluted with a digestion buffer (50 mM Tris pH 8.0) to a final volume of 300 μL, before adding Lys-C enzyme (Wako, Richmond, Va.) with an enzyme:substrate ratio of 1:20 (w:w). The solution was incubated at 37° C. for 4 hour. The peptides were separated by RP-HPLC on a Waters™ Acquity UPLC® H-Class using a HALO® Peptide ES-C18, 2.1×150 nm, 2.7 μm column (MAC-MOD Analytical, Inc., Chadds Ford, Pa.). MS spectra were acquired on a Waters™ Xevo® G2 Q-TOF system scanned in a range of m/z 100-2000. MS data was analyzed by BiopharmaLynx 1.3 (Waters™)
Target MS/MS LC/MS/MS of target peptide was conducted on a LTQ-Orbitrap MS system (Thermo Fisher, Waltham, Mass.). Resolution of 17500 in FT mode was applied for MS/MS acquisition. The peptides were separated by Waters™ Acquity UPLC® H-Class using a HALO® Peptide ES-C18 column, 2.1×$_{150}$ mm, 2.7 μm. MS/MS was scanned in m/z ranges depending on the m/z values of the precursor ions. Normalized fragmentation energy was set at 35% for CID fragmentation and 35% for ETD fragmentation. MS2 data was manually interpreted.
Alkaline Phosphatase Treatment 10 ug of mAb protein in AEX strip fraction were diluted in 50 uL phosphatase reaction buffer. 1 uL (10 unit) alkaline phosphatase from calf intestinal (New England Biolabs, Ipswish, Mass.) was added for incubation at 37° C. for 1 hour. Chicken ovalbumin (Sigma) was treated side by side as a positive control. 10 uL solution was injected to LC/MS for mass analysis.
Western Blotting MagicMark™ XP Western Standard (Invitrogen) and specific concentrations of both monoclonal antibodies (mAb) and control cell extracts (HEK293 whole cell extract and EGF stimulated A431 Cell lysate (Millilpore)) were reduced with 3-Mercaptoethanol plus heating at 95° C. then resolved by Tris-glycine based SDS PAGE using a 4-20% gradient gel (Novex). Resolved proteins were subsequently electro-transferred onto nitrocellulose membrane and washed overnight in Tris-buffered saline plus 0.05% TWEEN® (Polyethylene glycol sorbitan monolaurate) 20 (TBST) (Sigma) with rocking at 4° C. Membranes were then blocked for 1 hour in Tris-buffered saline plus 1% BSA (TBS-BSA) (Sigma) at room temperature with continuous rocking. Primary antibodies (anti-sulfotyrosine/anti-tyrosine sulfation (Millipore) or anti-human IgG (H+L) (Jackson ImmunoResearch Laboratories Inc.)) were diluted into TBS-BSA and incubated with the membrane for 2 h at room temperature. After washing with TBST, HRP-conjugated secondary antibodies (goat-anti-mouse or goat-anti-rabbit (Thermo Scientific)) were diluted into 5% Non-fat milk protein plus 0.05% TWEEN® 20-phosphobuffered saline (Invitrogen) and incubated at room temperature for 1 hour. After a final washing with TBST, chemilluminesence substrates (Thermo Scientific) were used for development; signals were recovered by exposure to photographic film (GE Healthcare Life Sciences) and subsequent processing. Nitrocellulose membrane stripping in between primary antibodies was done as indicated previously (Kaufmann S H, E. C., Shaper J H., The erasable Western blot. Anal Biochem., 1987. 161(1): p. 89-95).

Results and Discussion

Separation of mAb Molecule

Anion exchange chromatography (AEX) is typically utilized as a polishing step during monoclonal antibody purification. This step typically is operated in a flow-through mode, where the mAb flows through the column and in-process impurities (HCP, DNA) bind to the column. During the AEX development, it was noted that there was a fraction of the mAb loaded on the column bound to the resin, which affects protein recovery. The bound fraction of the protein eluted in the strip fraction of the AEX chromatography. To characterize the mAb bound to AEX column, fractions of the AEX chromatography were analyzed: "load" refer to the sample before AEX purification; "pool" refers to flow-through portion of the sample and "strip" refers to the bound fraction of the sample. Load, pool and strip fraction from AEX chromatography were initially analyzed by IEX-HPLC chromatography. FIG. 1 shows the IEX-HPLC profile of mAb in AEX load, pool and strip fraction. As shown in FIG. 1, the strip fraction had a significantly high amount of acidic variants as compared to the load and pool: ~65% acid variants in strip fraction (light trace) compared to 23% in pool fraction (dashed trace) and 33% in feed fraction (bold trace). Additional difference was noted in the acidic pre-main peak. This peak was present in the AEX feed at higher levels, where in the AEX pool, this peak was minimal. The strip fraction was enriched with the acidic pre-main peak. AEX chromatography was also performed at pH 7.0 or 7.5 with the same buffer and salt conditions as described above. At pH 7.0, similar reduction of the acidic pre-main peak was also observed in the AEX pool.

Analysis of Intact and Reduced Protein by Mass Spectrometry

Figure 2:
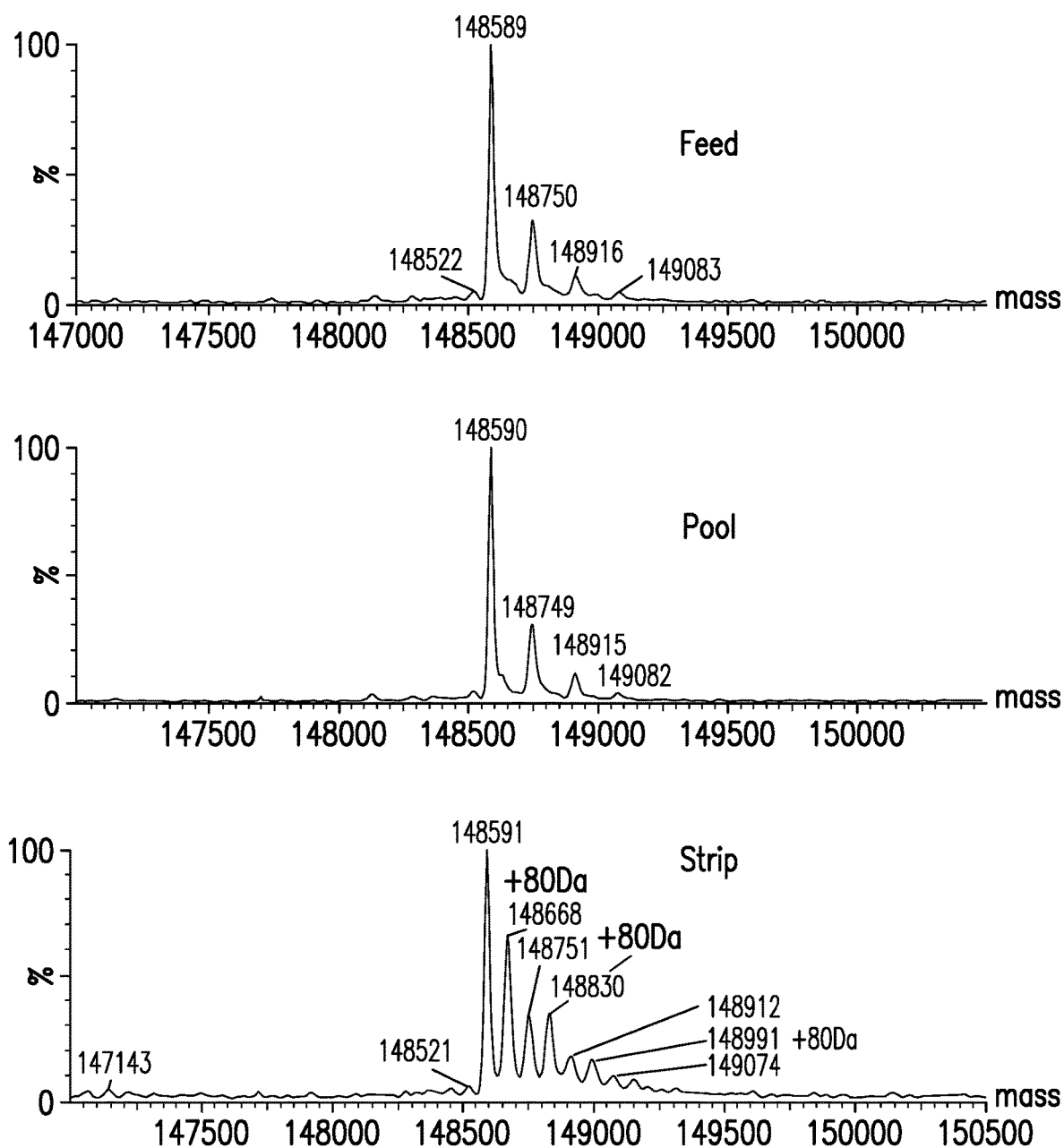
FIG. 2. Intact mass spectrum of AEX feed, pool and strip samples.
Figure 3:
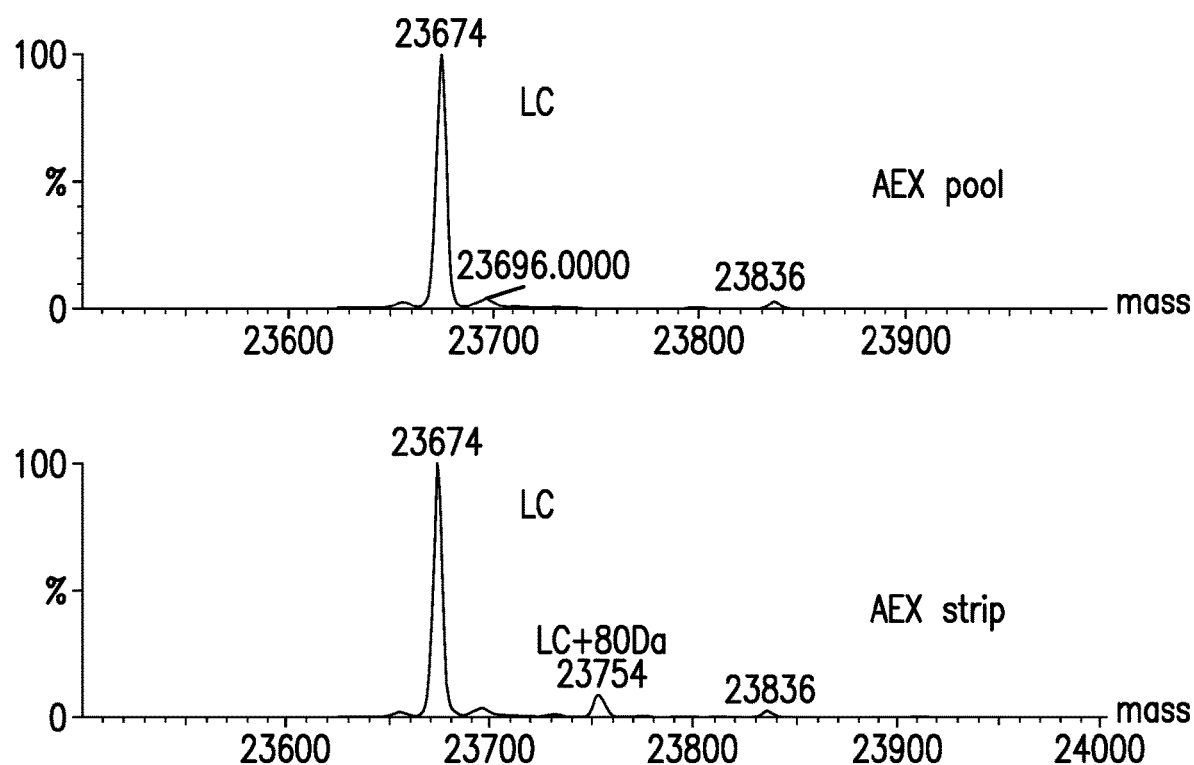
FIG. 3. Reduced light chain mass spectrum of AEX pool and strip samples.

To characterize the impurities, all three fractions (AEX load, pool and strip) were analyzed by intact and reduced LC/MS using Q-TOF MS. FIG. 2 shows the deconvoluted mass spectra of the intact molecule. Three main glycoforms were observed in all three fractions: G0F/G0F, G0F/G1F and G1 F/G1 F with mass of 148591 Da, 148751 Da and 148912 Da, respectively. The calculated intact mass of this molecule with G0F/G0F is 148590 Da. The mass errors for intact mass measurement are all within 25 ppm. Additional species were only detected in AEX strip fraction. These species correspond to 80 Da mass increase (148668, 148830, 148991 Da) of the three major glycoforms (G0F/G0F, G1F/G0F, G1F/G1F). To locate the modification, the light chain and heavy chain mass were measured after the disulfide bonds cleavage by reducing agent DTT. No difference was detected on heavy chain mass of strip fraction and pool fraction, suggesting the modification is not located on heavy chain (data not shown). As shown in FIG. 3, light chain apo form mass (23674 Da) and glycated light chain mass (23836 Da) were detected in both fractions (strip and pool fraction). A peak with 80 Da increase of light chain was only observed at 23754 Da in the AEX strip fraction. The mass error of reduced mass measurement is within 20 ppm. These data suggest that the 80 Da modifications are located on light chain of Ab6.

Analysis of mAb Antibody by Peptide Mapping

Figure 4A:
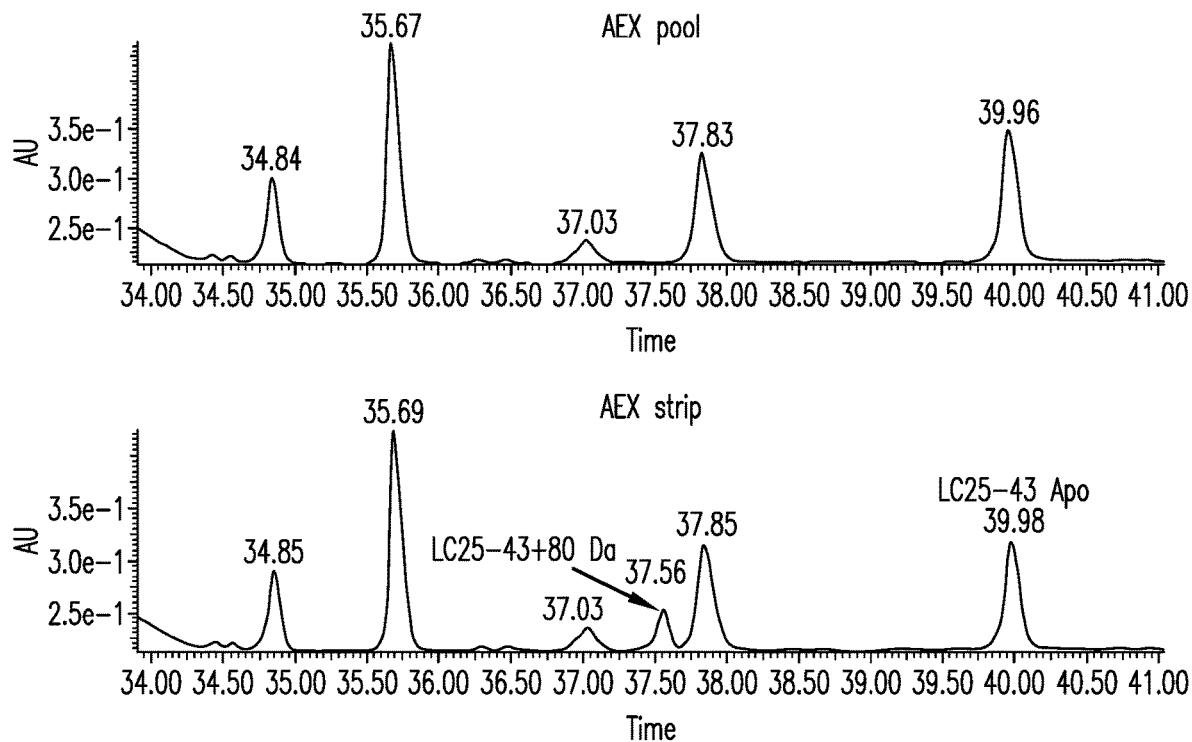
FIG. 4A-B. UV trace of reduced LysC peptide mapping of AEX pool and strip fractions.
Figure 4B:
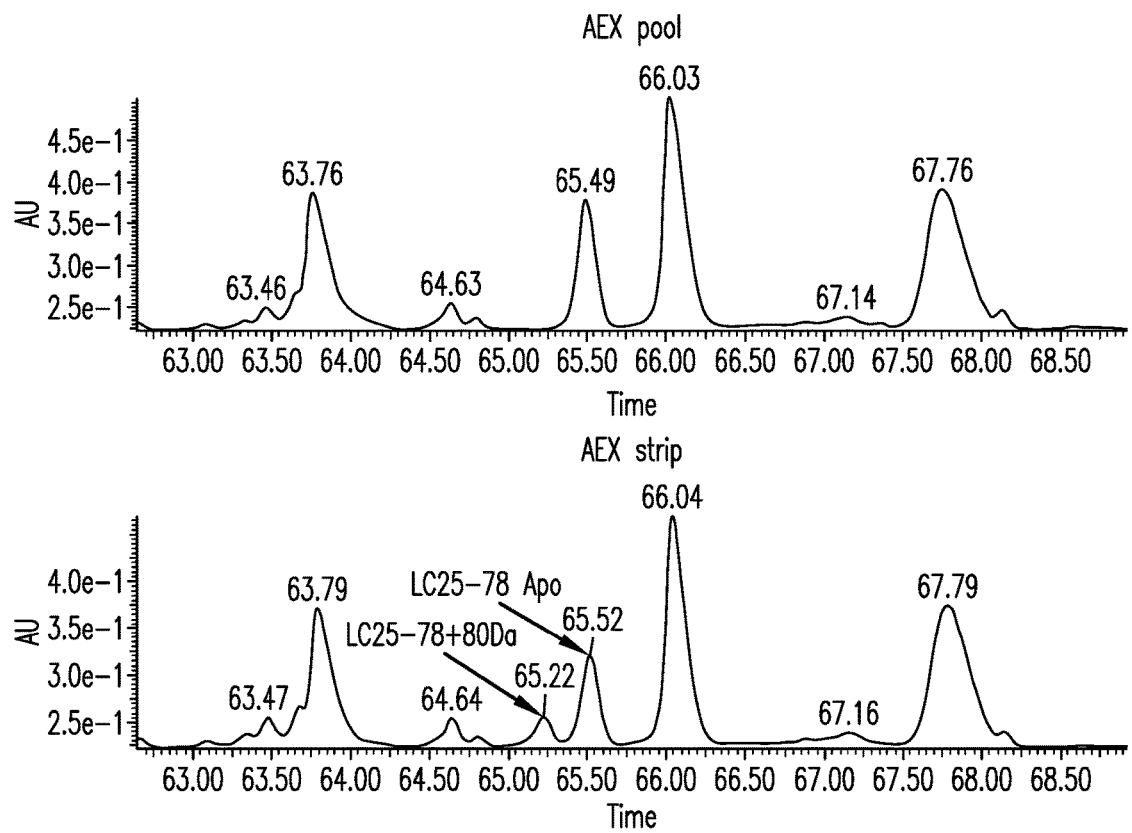

To further locate the modification site, AEX strip and pool fractions were reduced, alkylated and then digested by LysC enzyme. The peptide mixtures were mass mapped by Q-TOF MS. When comparing the UV trace of these two fractions, two differences were noticed. As shown in FIG. 4 (a) and (b), two new peaks were detected at retention time 37.6 min and 65.2 min in AEX strip fraction. The observed m/z in the new peaks are 1165.4796 (2+) at 37.6 min and 1476.7372 (4+) Da at 65.2 min. The observed masses correspond to light chain peptide AA25-43+80 Da and AA25-78+80 Da with mass error of 6.4 ppm and 9.8 ppm, respectively. Light chain peptide AA25-78 contains one mis-cleavage site. The modified and unmodified form of light chain peptide AA25-43 and AA25-78 were labeled in FIG. 4. The level of this modified peptide was estimated to be 20.9% and 21.6% for AA25-43 and AA25-78 compared to their apo forms based on the peak area in extracted ion chromatogram (SIC).

MS/MS Fragmentation of Modified Peptide

Figure 5A:
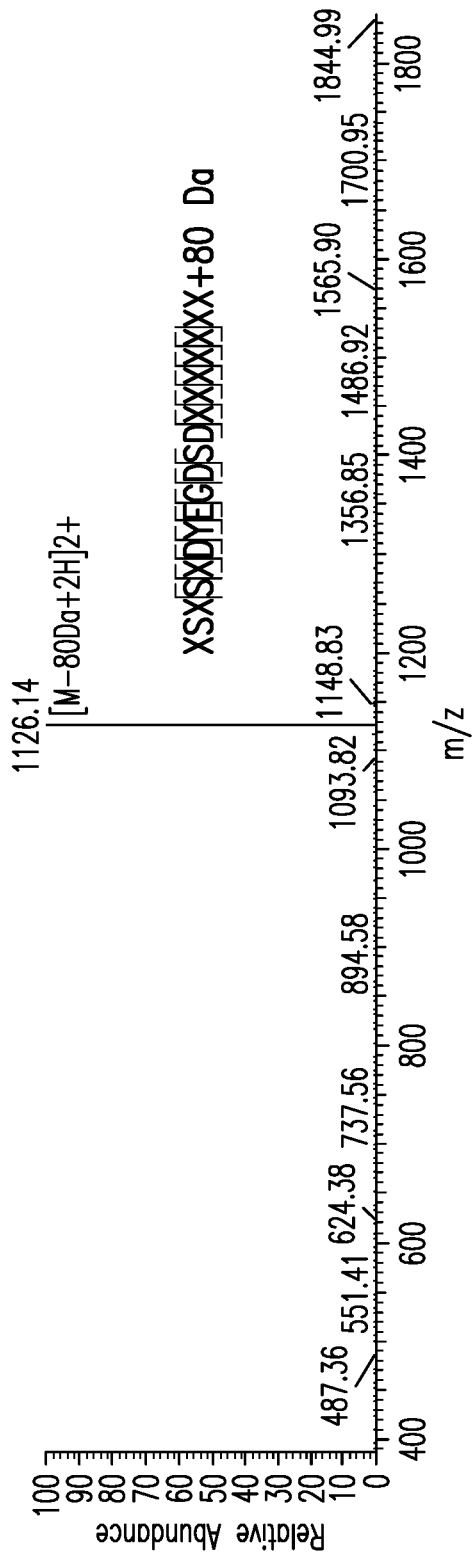
FIG. 5A-C. (A)CID fragmentation spectrum of light chain AA25-43 (XSXSXDYEGDSDXXXXXXX (SEQ ID NO: 65)+80 Da in 400-1800 m/z (B) Zoomed in m/z 300-1100 (C) Zoomed in m/z 1200-2000.
Figure 5B:
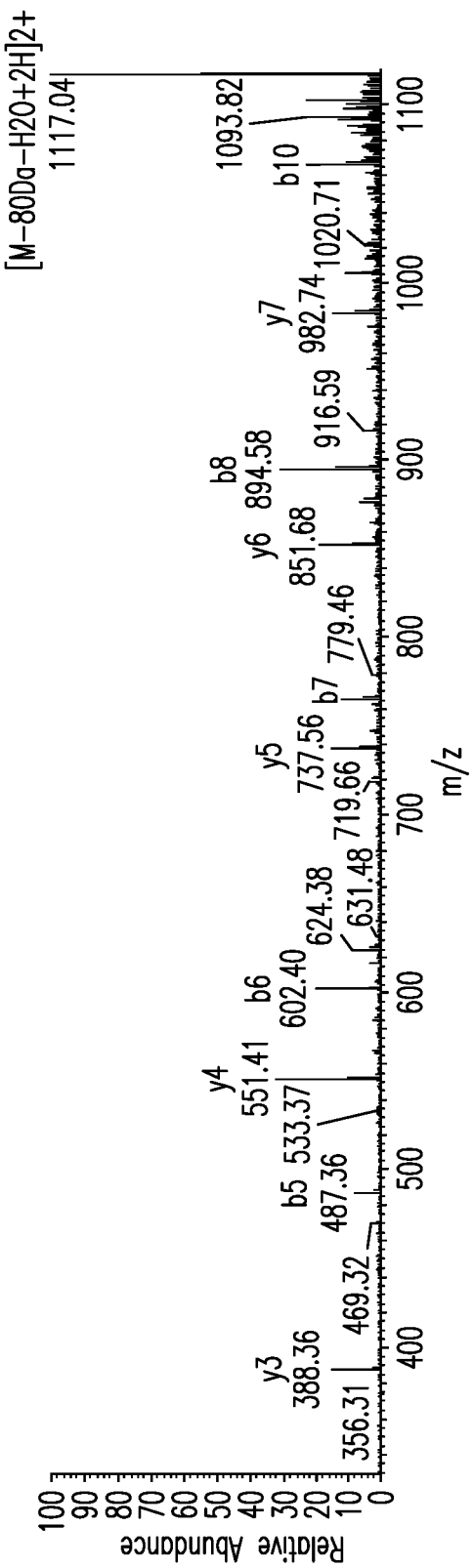
Figure 5C:
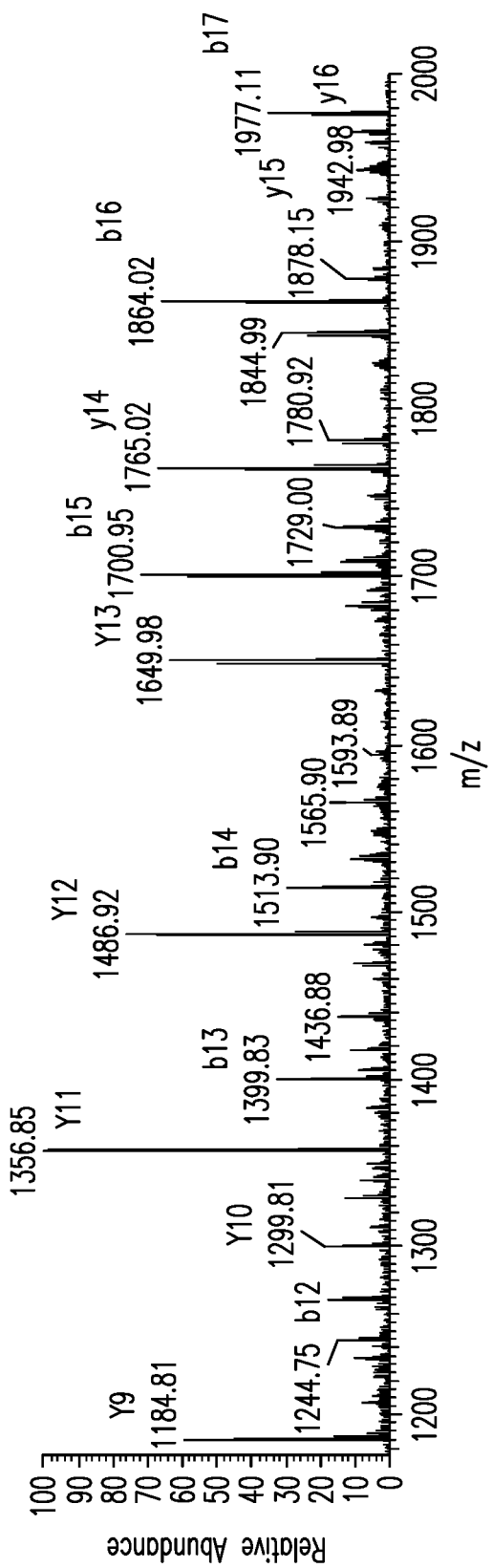

There are two possibilities of modification with 80 Da increase in mass: phosphorylation (+79.9663 Da) and sulfation (+79.9568 Da). The theoretical mass difference of these two modifications is only 0.0095 Da, which makes it difficult to be differentiated by mass only. Initially, the target peptide AA25-78 was fragmented by collision induced dissociation (CID) and the produced fragments were analyzed by LTQ-Orbitrap MS. As shown in FIG. 5, complete loss of modification group (80 Da) from precursor ion was observed. Only fragments from peptide backbone were detected, which confirms the peptide sequence of LC25-43. While no site specific information was obtained from CID fragmentation. It has been reported that sulfated tyrosine (sY) is very labile and could be easily lost under standard CID conditions (Nemeth-Cawley JF1, K. S., Rouse J C., Analysis of sulfated peptides using positive electrospray ionization tandem mass spectrometry. J Mass Spectrom., 2001. 36(12): p. 1301-11). It was not possible to obtain site-specific information on the location of the sulfate moieties using the positive ion CID MS/MS as none of the original precursor ions were present at the time of peptide backbone fragmentation. In contrast, phosphorylated peptides tend to persist under CID and peptide backbone fragmentation allows for the site-specific identification of the modification (Nemeth-Cawley JF1, K. S., Rouse J C., Analysis of sulfated peptides using positive electrospray ionization tandem mass spectrometry. J Mass Spectrom., 2001. 36(12): p. 1301-11). In FIG. 5, a neutral loss of 80 Da from precursor ion was observed. It's known that the characteristic neutral loss ion for phosphorylation is —$H_3PO_4$ (-98 Da) and characteristic fragment ion is $PO_3$ (-79 Da). While for sulfation, the characteristic neutral loss ions and fragment ions are both —$SO_3$ ion with 80 Da (Monigatti F, H. B., Steen H., Protein sulfation analysis—A primer. Biochim Biophys Acta., 2006. 1764(12): p. 1904-13). The CID MS2 data suggests the 80 Da modification is sulfation.

Figure 6:
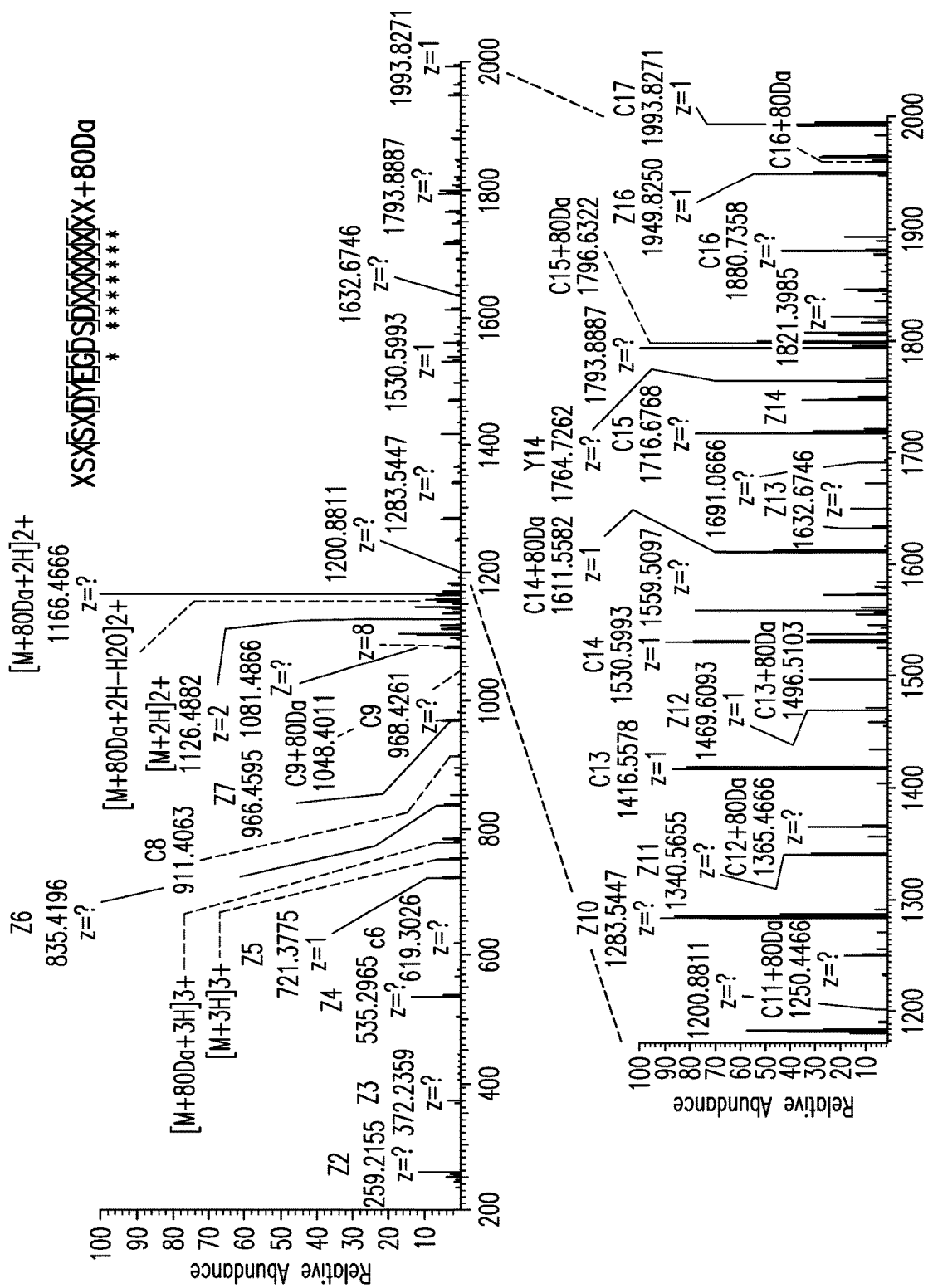
FIG. 6. ETD fragmentation of light chain peptide AA25-43(XSXSXDYEGDSDXXXXXXX (SEQ ID NO: 65)+80 Da. The 80 Da attached fragment ions were labeled.

Another widely used fragmentation mechanism is electron transfer dissociation (ETD). It transfers electron to a multiply protonated peptide/protein, which could lead to the cleavage of the N—Ca backbone bonds and generate c- and z-type fragment ions without loss of the information of the PTM localization (Mikesh L M, U. B., Chi A, Coon J J, Syka J E, Shabanowitz J, Hunt D F., The utility of ETD mass spectrometry in proteomic analysis. Biochim Biophys Acta., 2006. 1764(12): p. 1811-22). ETD can provide complementary information with CID: ETD process allows retaining the $SO_3$ group and thus the amino acid localization, while CID preferably fragments labile modifications. In our case, the target peptide was analyzed by LTQ-Orbitrap with ETD fragmentation and high resolution mass detection. As shown in FIG. 6, partial loss of 80 Da modifications was observed on precursor ion. Fragment ions with $SO_3$ group (80 Da) attached are labeled. Based on the detection of $SO_3$ attached fragment ions (c9, c11, c12-16), the modification site is identified to be tyrosine 31 on light chain, which is in the CDR1 region of the mAb molecule.

Alkaline Phosphatase Treatment

Figure 7A:
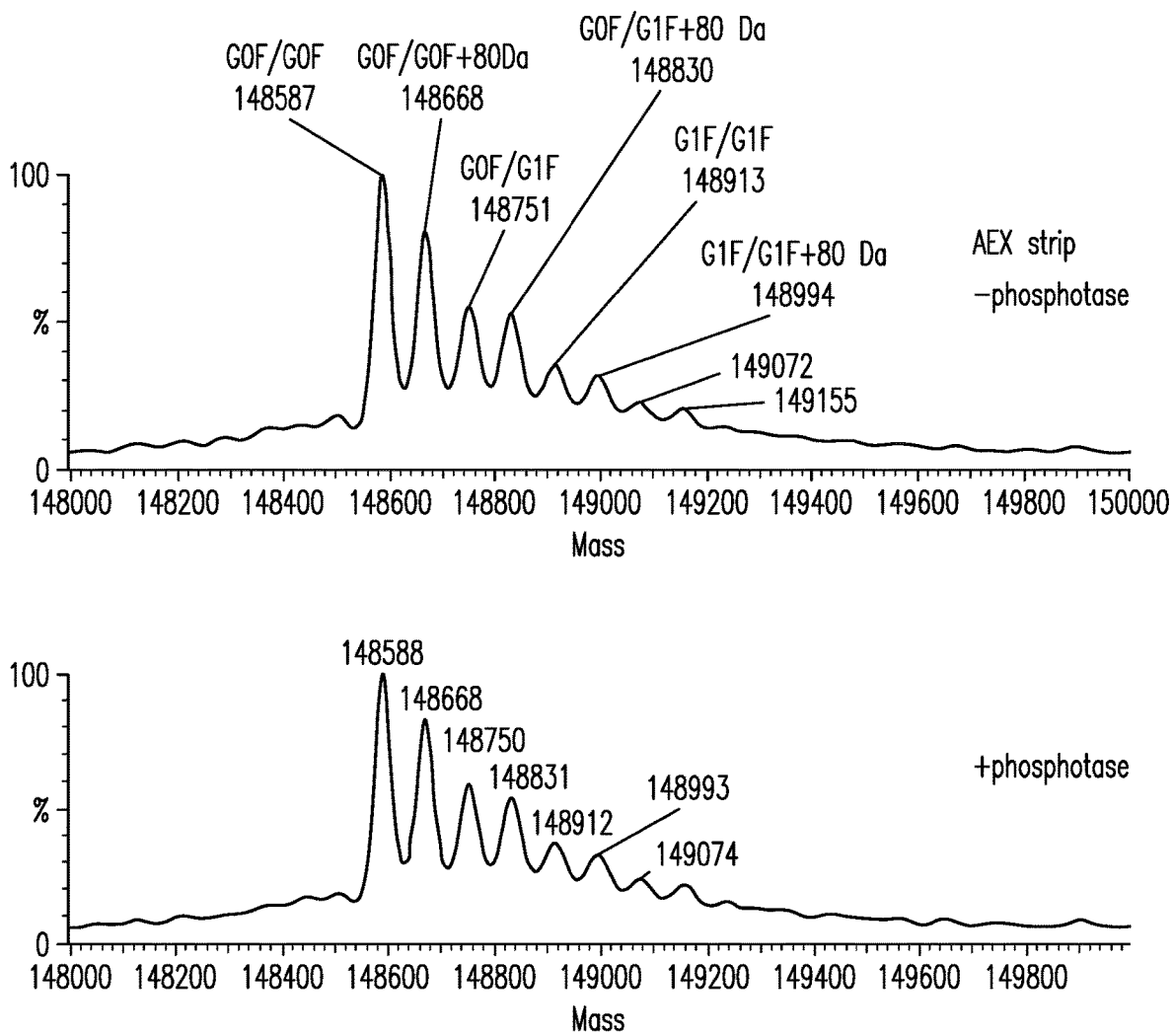
FIG. 7A-B. (A) Deconvoluted intact mass spectra of AEX strip fraction with and without alkaline phosphatase treatment. (B) Deconvoluted intact mass spectra of chicken ovalbumin with and without alkaline phosphatase treatment.
Figure 7B:
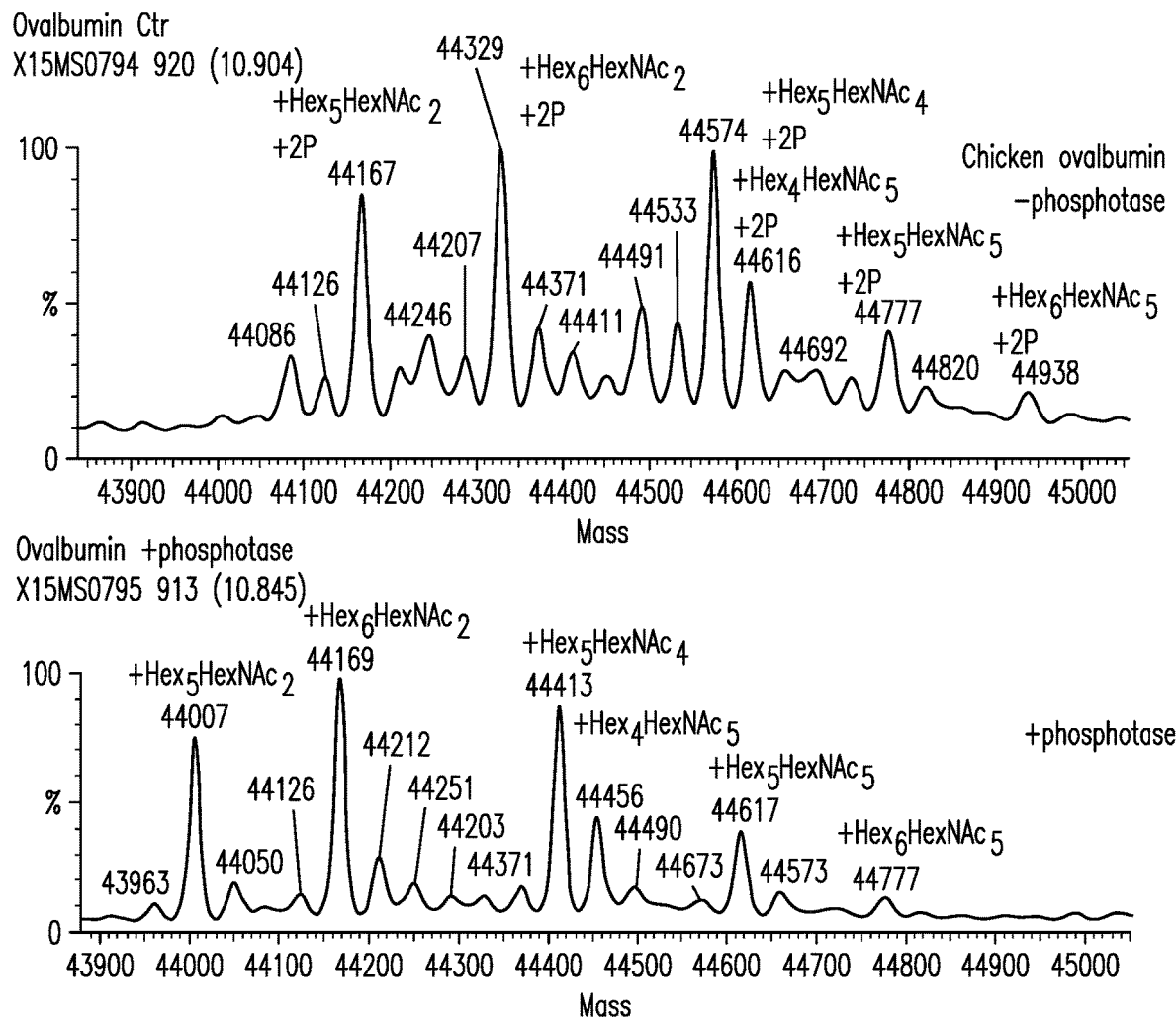

Since phosphorylation and sulfation of tyrosine are isobaric, alkaline phosphatase was used here to distinguish these two modifications (Yu Y, H. A., Moore K L, Leary J A., Determination of the sites of tyrosine 0-sulfation in peptides and proteins. Nat Methods, 2007. 4(7): p. 583-8). Alkaline phosphatase has been widely used for removing phosphorylation group from proteins. Chicken albumin was used as a positive control as this protein has been widely known for its phosphorylation and glycosylation form. Chicken albumin and mAb in AEX strip fraction were treated with phosphatase and incubate at 37° C. side by side. FIG. 7 shows the measured intact mass of mAb and chicken ovalbumin before and after phosphatase treatment. As shown in FIG. 7(a), no mass change was observed for mAb. While for chicken albumin (FIG. 7 (b)), an obvious mass shift of 160 Da was observed for all the major glycoforms. Since chicken albumin contains two phosphorylation sites, the loss of 160 Da confirms the activity of alkaline phosphatase. As no mass change was detected before and after phosphatase treatment, it suggests that this mAb in AEX strip is not phosphorylated.

Western Blot

Figures 8A, 8B:
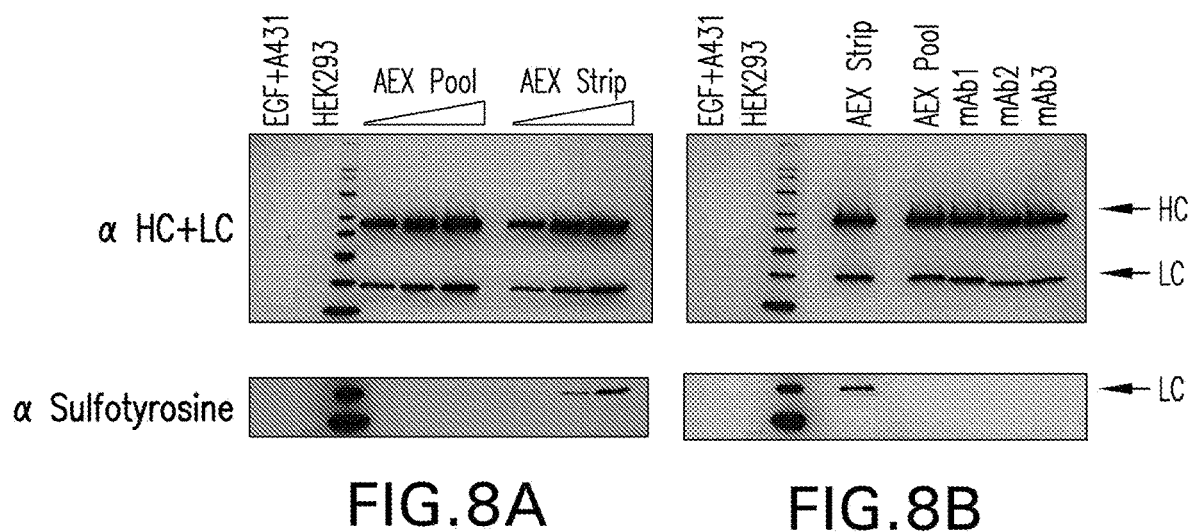
FIG. 8A-B. (A) Normalized concentrations of mAb AEX pool and strip were subjected to reduced SDS-PAGE, probed for the human heavy (HC) and light chains (LC) by western hybridization (upper panel), then stripped and re-probed for antisulfotyrosine (lower panel). See the indications for HC and LC at the far right. (B) Normalized concentrations of different CHO-derived mAbs in addition to AEX strip and pool are subjected to reduced SDS PAGE, probed for the human HC and LC by western hybridization, then stripped and re-probed for anti sulfotyrosine. For both (A) and (B) MagicMark™ XP was used as a protein molecular weight standard, and equal amounts of HEK293 and EGF-treated A431 cell extracts are analyzed as controls.

Thus far, LC/MS analysis has been used to investigate the nature 80 Da adduct to tyrosine 31 on the light chain CDR. MS2 analysis and mass analysis of the mAb AEX strip fraction after phosphatase-treatment have suggested that the 80 Da adduct is sulfation on tyrosine 31. However, the ability of these mass analysis-based techniques to directly distinguish between tyrosine-sulfation and phosphorylation is problematic due to the similar molecular mass of these two groups. To begin addressing this problem, Western blotting with an anti-sulfotyrosine-specific monoclonal antibody was applied to confirm the presence of tyrosine sulfation in the mAb AEX strip fraction (Xu J, D. X., Tang M, Li L, Xiao L, Yang L, Zhong J, Bode A M, Dong Z, Tao Y, Cao Y., Tyrosylprotein sulfotransferase-1 and tyrosine sulfation of chemokine receptor 4 are induced by Epstein-Barr virus encoded latent membrane protein 1 and associated with the metastatic potential of human nasopharyngeal carcinoma. PLoS One., 2013. 8(3): p. e56114). In FIG. 8a (upper panel), the normalized concentrations of mAb AEX pool and strip fractions were subjected to reduced SDS PAGE, probed for the human heavy and light chains by western hybridization. The increased concentrations of heavy- and light chains from pool and strip were then "stripped" of the first detecting antibodies and re-probed with an anti-sulfotyrosine-specific monoclonal antibody (lower panel). As shown in FIG. 8a (lower panel), positive signals were only detected on light chain of strip fractions, suggesting that it contains tyrosine sulfation. As a control for cross reactivity with phosphorylation, lane one was loaded with a commercial source of EGF-treated A431 cell extract that is enriched with phosphorylated proteins. The lack of positive signal in lane one of the lower panel shows the anti-sulfotyrosine monoclonal antibody does not have strong cross reactivity with phosphorylation (FIG. 8a, lower panel). Further, HEK 293 extract, which was suggested by the manufacturer as a positive control for the anti-sulfotyrosine monoclonal antibody, was loaded in lane 2. The positive signal below the bottom-20 KDa is consistent with manufacturer's analysis (FIG. 8a, lower panel). In FIG. 8b, normalized concentrations of different CHO-derived mAbs (mAb1, 2 and 3) in addition to AEX strip and pool are subjected to reduced SDS PAGE, probed for the human heavy and light chains by western hybridization (upper panel), then stripped and re-probed for antisulfotyrosine (lower panel). In agreement with FIG. 8a, only the AEX mAb strip shows a positive signal at the light chain position when probed with the anti-sulfotyrosin antibody. No positive signal was observed on tyrosine sulfation for the other three CHO-derived Merck mAbs when similar amounts of protein were analyzed. This is consistent with our observation that no increased level of AEX acidic peak or tyrosine sulfation hotspot was detected on these three mAbs (data not shown).

Figure 9A:
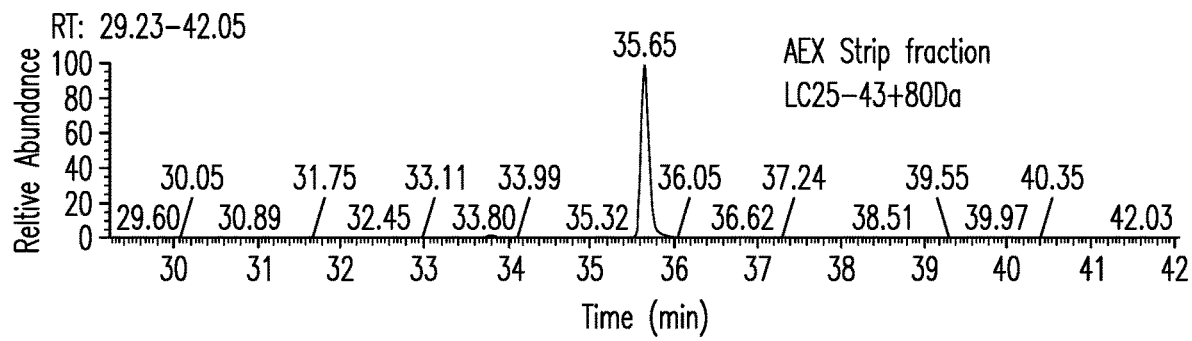
FIG. 9A-C. SIC of (A) LC25-43+80 Da from AEX Strip Fraction, (B) Synthetic Peptide XSXSXDYEGDSDXXXXXXX (SEQ ID NO: 65)+Phosphorylation and (C) Synthetic Peptide XSXSXDYEGDSDXXXXXXX (SEQ ID NO: 65)+Sulfation.
Figure 9B:
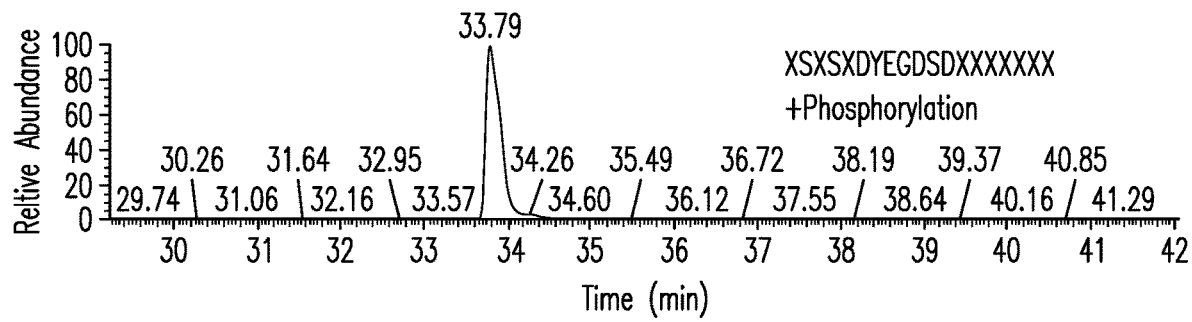
Figure 9C:
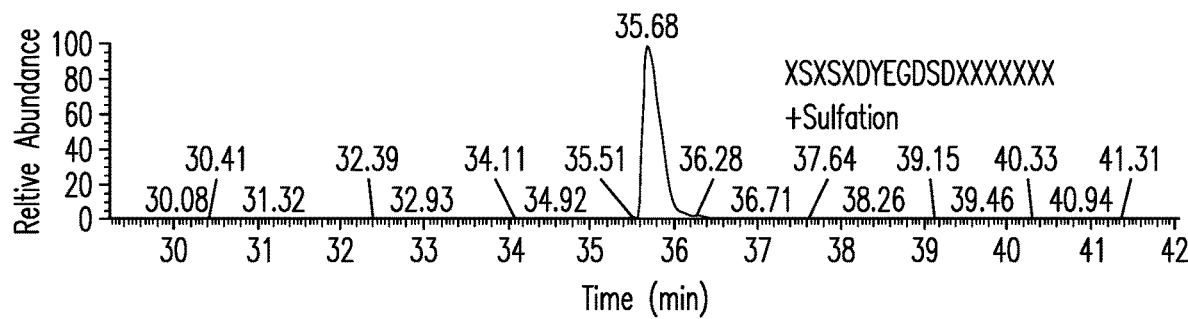

Comparison of Retention Time with Synthetic Peptide with Sulfation or Phospohorylation To further distinguish phosphorylation and sulfation, synthetic peptide with identical sequence of LC AA25-43 (XSXSXDYEGDSDXXXXXXX) (SEQ ID NO: 65) modified with either phosphorylation or sulfation on the Y31 were analyzed by LC/MS. FIG. 9 shows the SIC of synthetic peptide XSXSXDYEGDSDXXXXXXX (SEQ ID NO: 65)+ phosphorylation, XSXSXDYEGDSDXXXXXXX (SEQ ID NO: 65)+sulfation and AA25-43+80 Da in AEX strip. Synthetic peptide with sulfation elutes at the same retention time with AEX strip, while the synthetic peptide with phosphorylation elutes earlier than AEX strip. This further confirms our observation that Y31 on light chain is sulfated.

Structure of Tyrosine Sulfation Site

Figure 10:
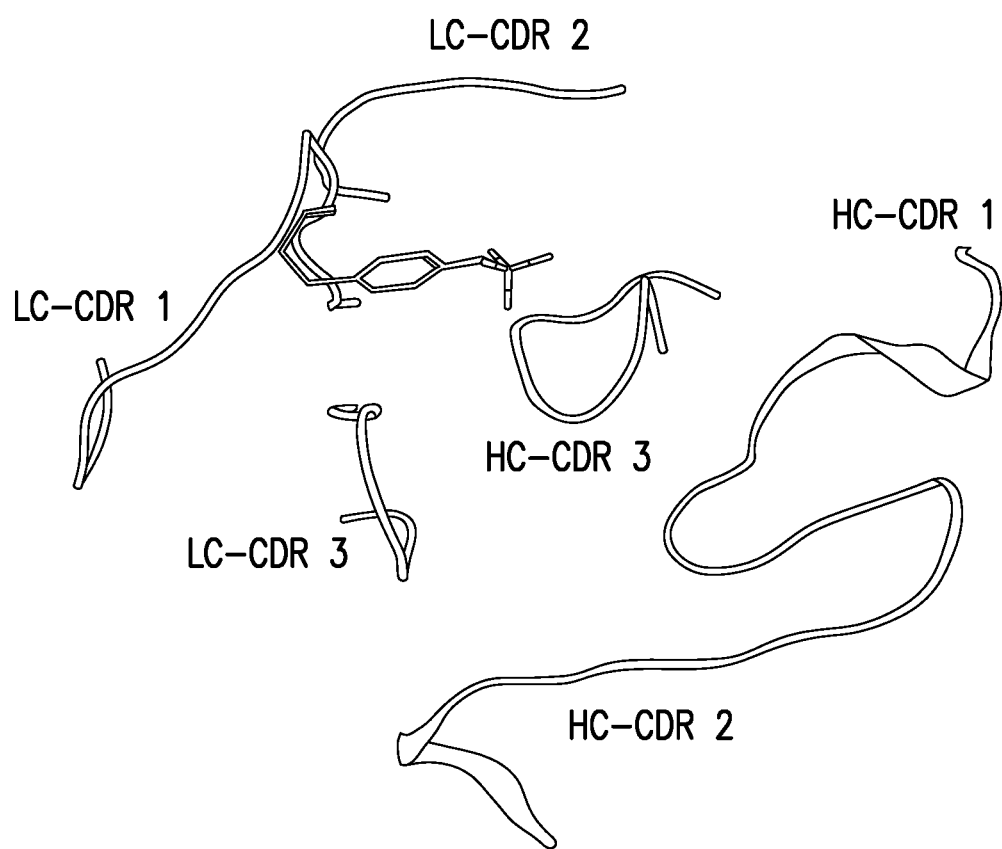
FIG. 10. mAb tyrosine (Y31) site showing the CDR loops in ribbon diagram for both the heavy and light chain.

The protein tyrosine sulfation reaction is catalyzed by the Golgi enzyme called the tyrosylprotein sulfotransferase. Previous studies indicated that TPSTs recognize accessible tyrosine residues that are usually surrounded by several acidic residues within–5 to +5 positions (Hortin G, F. R., Gordon J I, Strauss A W., Characterization of sites of tyrosine sulfation in proteins and criteria for predicting their occurrence. Biochem Biophys Res Commun., 1986. 141(1): p. 326-33; Rosenquist G L, N. H. J., Analysis of sequence requirements for protein tyrosine sulfation. Protein Sci., 1993. 2(2): p. 215-22; Teramoto T1, F. Y., Kawaguchi Y, Kurogi K, Soejima M, Adachi R, Nakanishi Y, Mishiro-Sato E, Liu M C, Sakakibara Y, Suiko M, Kimura M, Kakuta Y, Crystal structure of human tyrosylprotein sulfotransferase-2 reveals the mechanism of protein tyrosine sulfation reaction. Nat Commun., 2013. 4: p. 1572). The acceptor tyrosine needs to have acidic residues nearby to enable the recognition of positively charged residues in TPST2 substrate binding site. The acceptor tyrosine also needs to be in an intrinsically flexible region to fit into the deep cleft of TPST2. However, no general consensus sequence for tyrosine sulfation sites has been defined. The most common features describing the sequence surroundings of sulfated tyrosine includes presence of one acidic amino acid within two residues of the tyrosine; presence of at least three acidic amino acid within 5 residues and presence of turn-inducing amino acids nearby, etc (Monigatti F, H. B., Steen H., Protein sulfation analysis—A primer. Biochim Biophys Acta., 2006. 1764(12): p. 1904-13). FIG. 10 shows the structure of the mAb tyrosine site in the context of CDR loops in ribbon diagram, which was generated by MOE software (Chemical Computing Group, Montreal, Canada). The sequence near to light chain Y31 on this mAb is: XSXSXDYEGDSDXXXXXXX (SEQ ID NO: 65). In this sequence, the adjacent residues of Y31 are both acidic: Aspartic acid (D) and Glutamic Acid (E). A total of four acidic residues are within five residues of Y31: three D and one E. Four turn inducing residues are close to Y31: three serine(S) and one glycine(G). The unique structure of Y31 with neighboring acidic amino acids and elements of local secondary structure play an essential role to make this modification happen.

We describe here the evidence that points to the presence of an unexpected O-linked tyrosine sulfation in a CHO produced antibody. The location of this labile modification was found in CDR1 region of light chain, as identified by mass spectrometry with ETD fragmentation. This tyrosine sulfation was further confirmed by phosphatase treatment, Western blot experiment using anti-tyrosine sulfation antibody and retention time correlation with synthetic sulfated peptide. Structural analysis of CDR tyrosine confirms the impact of acidic residues on sulfation. The neighboring acidic amino acid residues and elements of local secondary structure might play an essential role to make Y31 a hotspot for sulfation.

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes. This application claims priority to U.S. provisional application No. 62/414,209 incorporated herein by reference in its entirety. All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents. To the extent that the references provide a definition for a claimed term that conflicts with the definitions provided in the instant specification, the definitions provided in the instant specification shall be used to interpret the claimed invention.

We claim:

1. A purified composition comprising non-CDR-L1 tyrosine sulfated antibodies that specifically bind to human lymphocyte activation gene 3 (anti-hLAG3) comprising: a heavy chain amino acid sequence of SEQ ID NO: 52 and a light chain amino acid sequence of SEQ ID NO: 51, and less than about 0.5% CDR-L1 tyrosine sulfated anti-hLAG3antibodies as compared to non-CDR-L1 tyrosine sulfated anti-hLAG3 antibodies as determined by mass spectrometry, wherein the CDR-L1 tyrosine sulfated anti-hLAG3 antibodies comprise a heavy chain amino acid sequence of SEQ ID NO: 52 and a light chain amino acid sequence of SEQ ID NO: 51 with the tyrosine at CDR-L1 sulfated,
wherein the non-CDR-L1 tyrosine sulfated anti-hLAG3 antibodies and CDR-L1 tyrosine sulfated anti-hLAG3 antibodies are expressed from Chinese Hamster Ovary Cells, and wherein the purified composition is obtained by a method comprising the steps of: applying an aqueous mixture comprising CDR-L1 tyrosine sulfated and non-CDR-L1 tyrosine sulfated anti-hLAG3antibodies at a pH of about 6.5 to 7.0 to an anion exchange resin, and collecting a non-resin bound aqueous fraction of the aqueous mixture.

2. The purified composition of claim 1, wherein the non-CDR-L1 tyrosine sulfated and CDR-L1 tyrosine sulfated anti-hLAG3 antibodies comprise N-linked glycans of one or more of G0, G0-F, G1, G1-F, G2-F and Man5 from expression in Chinese Hamster Ovary (CHO) cells.

3. The purified composition of claim 2, wherein the non-CDR-L1 tyrosine sulfated anti-hLAG3 antibodies are glycosylated antibody species having a molecular weight of about 148590 Da, 148749 Da, 148752 Da, 148914 Da or 148915 Da, or a combination thereof.

4. The purified composition of claim 1, wherein the non-CDR-L1 tyrosine sulfated and CDR-L1 tyrosine sulfated anti-hLAG3 antibodies have the N-terminal heavy chain glutamine converted to pyroglutamate or pyroglutamic acid and/or C-terminal heavy chain lysine removed.

5. The purified composition of claim 1, wherein the method further comprises the following steps: washing the anion exchange resin with an aqueous composition under isocratic conditions, collecting a flow-through fraction from the wash, and pooling the flow-through fraction from the wash with the non-resin bound aqueous fraction.

6. The purified composition of claim 1, wherein the purified composition is obtained by equilibrating the anion exchange resin comprising a dimethylaminopropyl anion exchange ligand in a chromatography column with 25 mM sodium phosphate at a pH of 6.5, adjusting the pH of the aqueous mixture to 6.5, applying the aqueous mixture to the column, collecting a flow-through fraction from the column, washing the resin in the column with 25 mM sodium phosphate at a pH of 6.5, collecting the flow-through fraction from the wash, and pooling the flow-through fractions from the aqueous mixture and the wash.

7. The purified composition of claim 1, wherein the purified composition is obtained by equilibrating the anion exchange resin comprising a quarternized polyethyleneimine anion exchange ligand in a chromatography column with 25 mM sodium phosphate and 5 mM NaCl at a pH of 7.0, adjusting the pH of the aqueous mixture to 7.0, applying the aqueous mixture to the column, collecting a flow-through fraction from the column, washing the resin in the column with 25 mM sodium phosphate and 5 mM NaCl at a pH of 7.0, and collecting the flow-through fraction from the wash, and pooling the flow-through fractions from the aqueous mixture and the wash.

8. The purified composition of claim 7, wherein the A280 absorbance of the flow-through fraction from the aqueous mixture and wash is collected from when the A280 first reaches at least about 2.5 absorbance units/cm and continues until the A280 falls below about 1.0 absorbance units/cm.

9. The purified composition of claim 6, further comprising purifying the non-CDR-L1 tyrosine sulfated and CDR-L1 tyrosine sulfated anti-hLAG3 antibodies from the pooled flow-through fractions by cation exchange chromatography, anion exchange chromatography in bind-elute mode, hydrophobic interaction chromatography, protein-A chromatography, protein-L chromatography, protein-G chromatography, hydroxyapatite chromatography, size exclusion chromatography, fractional precipitation, filtration, centrifugation or viral inactivation.

10. The purified composition of claim 6, wherein the non-CDR-L1 tyrosine sulfated and CDR-L1 tyrosine sulfated anti-hLAG3 antibodies comprise N-linked glycans of one or more of G0, G0-F, G1, G1-F, G2-F and Man5 from expression in Chinese Hamster Ovary (CHO) cells.

11. A purified composition comprising non-CDR-L1 tyrosine sulfated antibodies that specifically bind to human lymphocyte activation gene 3 (anti-hLAG3) comprising: a heavy chain amino acid sequence of SEQ ID NO: 52 and a light chain amino acid sequence of SEQ ID NO: 51 and less than about 0.5% CDR-L1 tyrosine sulfated anti-hLAG3antibodies as compared to non-CDR-L1 tyrosine sulfated anti-hLAG3 antibodies as determined by mass spectrometry, wherein the CDR-L1 tyrosine sulfated anti-hLAG3 antibodies comprise a heavy chain amino acid sequence of SEQ ID NO: 52 and a light chain amino acid sequence of SEQ ID NO: 51 with the tyrosine at CDR-L1 sulfated, wherein the non-CDR-L1 tyrosine sulfated anti-hLAG3 antibodies and the CDR-L1 tyrosine sulfated anti-hLAG3 antibodies are expressed from Chinese Hamster Ovary Cells, and wherein the purified composition is obtained by a method comprising the steps of: applying an aqueous mixture comprising CDR-L1 tyrosine sulfated and non-CDR-L1 tyrosine sulfated anti-hLAG3 antibodies at a pH of 6.5 to 7.5 to an anion exchange resin, and collecting a non-resin bound aqueous fraction of the aqueous mixture.

12. The purified composition of claim 11, wherein the method further comprises the following steps: washing the anion exchange resin with an aqueous composition under isocratic conditions, collecting a flow-through fraction from the wash, and pooling the flow-through fraction from the wash with the non-resin bound aqueous fraction.

13. The purified composition of claim 11, wherein the purified composition is obtained by equilibrating the anion exchange resin with about 10-50 mM sodium phosphate at a pH of 6.5 to 7.5, adjusting the pH of the aqueous mixture to 6.5 to 7.5, applying the aqueous mixture to the column, collecting a flow-through fraction from the column, washing the resin in the column with about 10-50 mM sodium phosphate at a pH of 6.5 to 7.5, and collecting a flow-through fraction from the wash, and pooling the flow-through fractions from the aqueous mixture and the wash.

14. The purified composition of claim 11, wherein the non-CDR-L1 tyrosine sulfated and CDR-L1 tyrosine sulfated anti-hLAG3 antibodies comprise a heavy chain amino acid sequence of SEQ ID NO: 52 and a light chain amino acid sequence of SEQ ID NO: 51 with the N-terminal heavy chain glutamine converted to pyroglutamate or pyroglutamic acid and/or the C-terminal heavy chain lysine removed.

15. The purified composition of claim 14, wherein the non-CDR-L1 tyrosine sulfated anti-hLAG3 antibodies are glycosylated antibody species having molecular weights of about 148590 Da, 148749 Da, 148752 Da, 148914 Da, or 148915 Da, or a combination thereof.

16. The purified composition of claim 11, wherein the non-CDR-L1 tyrosine sulfated and CDR-L1 tyrosine sulfated anti-hLAG3 antibodies comprise N-linked glycans of one or more of G0, G0-F, G1, G1-F, G2-F and Man5 from expression in Chinese Hamster Ovary (CHO) cells.

17. The purified composition of claim 14, wherein the non-CDR-L1 tyrosine sulfated and CDR-L1 tyrosine sulfated anti-hLAG3 antibodies comprise N-linked glycans of one or more of G0, G0-F, G1, G1-F, G2-F and Man5 from expression Chinese Hamster Ovary (CHO) cells.

18. The purified composition of claim 10, wherein the non-CDR-L1 tyrosine sulfated anti-hLAG3 antibodies are glycosylated antibody species having a molecular weight of about 148590 Da, 148749 Da, 148752 Da, 148914 Da, 148915 Da, or a combination thereof.

19. The purified composition of claim 18, wherein the non-CDR-L1 tyrosine sulfated anti-hLAG3 antibodies have: (i) a molecular weight of 148590 Da, (ii) G0F glycans, (iii) the N-terminal heavy chain glutamine converted to pyroglutamic acid, and (iv) the C-terminal heavy chain lysine removed.

20. The purified composition of claim 18, wherein the non-CDR-L1 tyrosine sulfated anti-hLAG3 antibodies have: (i) a molecular weight of 148749 Da or 148752 Da, (ii) G0F and G1F glycans, (iii) the N-terminal heavy chain glutamine converted to pyroglutamic acid, and (iv) the C-terminal heavy chain lysine removed.

21. The purified composition of claim 18, wherein the non-CDR-L1 tyrosine sulfated anti-hLAG3 antibodies have: (i) a molecular weight of 148914 Da or 148915 Da, (ii) G1F glycans, (iii) the N-terminal heavy chain glutamine converted to pyroglutamic acid, and (iv) the C-terminal heavy chain lysine removed.

22. The purified composition of claim 15, wherein the non-CDR-L1 tyrosine sulfated anti-hLAG3 antibodies have: (i) a molecular weight of 148590 Da, (ii) G0F glycans, (iii) the N-terminal heavy chain glutamine converted to pyroglutamic acid, and (iv) the C-terminal heavy chain lysine removed.

23. The purified composition of claim 15, wherein the non-CDR-L1 tyrosine sulfated anti-hLAG3 antibodies have: (i) a molecular weight of 148749 Da or 148752 Da, (ii) G0F and G1F glycans, (iii) the N-terminal heavy chain glutamine converted to pyroglutamic acid, and (iv) the C-terminal heavy chain lysine removed.

24. The purified composition of claim 15, wherein the non-CDR-L1 tyrosine sulfated anti-hLAG3 antibodies have: (i) a molecular weight of 148914 Da or 148915 Da, (ii) G1F glycans, (iii) the N-terminal heavy chain glutamine converted to pyroglutamic acid, and (iv) the C-terminal heavy chain lysine removed.

\* \* \* \* \*

SEQUENCE LISTING

```
<160> NUMBER OF SEQ ID NOS: 65

<210> SEQ ID NO 1
<211> LENGTH: 408
<212> TYPE: DNA
<213> ORGANISM: Artificial Sequence
<220> FEATURE:
<223> OTHER INFORMATION: Humanized mouse

<400> SEQUENCE: 1
atgaaatgca gctgggtcat cttcttcctg atggcagtgg ttataggaat caattcagag      60
gttcagctgc tccagtctgg ggcagaactt gtgaggcag gggcctcagt caagttgtcc      120
tgcacagcct ctggcttcaa cattgaagac tactatatgc actggatgaa acagaggcct     180
gaacagggcc tggagtggat tggatggatt gatcctgtga atggtgatac tgaatatgcc     240
ccgaagttcc agggcaaggc cactatgact gcagacacat cctccaacac agcctaccta     300
cacctcaaca gcctgacatc tgaggacact gccgtctatt actgtaattt ctatgatggt     360
tacctctttg ctttctgggg ccaagggacc ctggtcactg tctctgca              408

<210> SEQ ID NO 2
<211> LENGTH: 136
<212> TYPE: PRT
<213> ORGANISM: Artificial Sequence
<220> FEATURE:
<223> OTHER INFORMATION: Humanized mouse

<400> SEQUENCE: 2
```

```
Met Lys Cys Ser Trp Val Ile Phe Phe Leu Met Ala Val Val Ile Gly
1               5                   10                  15

Ile Asn Ser Glu Val Gln Leu Leu Gln Ser Gly Ala Glu Leu Val Arg
            20                  25                  30

Ser Gly Ala Ser Val Lys Leu Ser Cys Thr Ala Ser Gly Phe Asn Ile
        35                  40                  45

Glu Asp Tyr Tyr Met His Trp Met Lys Gln Arg Pro Glu Gln Gly Leu
    50                  55                  60

Glu Trp Ile Gly Trp Ile Asp Pro Val Asn Gly Asp Thr Glu Tyr Ala
65              70                  75                  80

Pro Lys Phe Gln Gly Lys Ala Thr Met Thr Ala Asp Thr Ser Ser Asn
                85                  90                  95

Thr Ala Tyr Leu His Leu Asn Ser Leu Thr Ser Glu Asp Thr Ala Val
            100                 105                 110

Tyr Tyr Cys Asn Phe Tyr Asp Gly Tyr Leu Phe Ala Phe Trp Gly Gln
        115                 120                 125

Gly Thr Leu Val Thr Val Ser Ala
    130                 135

<210> SEQ ID NO 3
<211> LENGTH: 10
<212> TYPE: PRT
<213> ORGANISM: Mus

<400> SEQUENCE: 3

Gly Phe Asn Ile Glu Asp Tyr Tyr Met His
1               5                   10

<210> SEQ ID NO 4
<211> LENGTH: 17
<212> TYPE: PRT
<213> ORGANISM: Mus

<400> SEQUENCE: 4

Trp Ile Asp Pro Val Asn Gly Asp Thr Glu Tyr Ala Pro Lys Phe Gln
1               5                   10                  15

Gly

<210> SEQ ID NO 5
<211> LENGTH: 8
<212> TYPE: PRT
<213> ORGANISM: Mus

<400> SEQUENCE: 5

Tyr Asp Gly Tyr Leu Phe Ala Phe
1               5

<210> SEQ ID NO 6
<211> LENGTH: 396
<212> TYPE: DNA
<213> ORGANISM: Artificial Sequence
<220> FEATURE:
<223> OTHER INFORMATION: Humanized mouse

<400> SEQUENCE: 6
atgaggtgcc tagctgagtt cctggggctg cttgtgctct ggatccctgg agccattggg     60
gatattgtgc tgactcaggc tgcaccctct gtacctgtca ctcctggaga gtcagtgtcc    120
atctcctgca ggtctagtaa gagtctcctg catagtgatg gcaacactta tctgtattgg    180
```

```
ctcctgcaga ggccaggcca gtctcctcag ctcctgatat atcggatgtc aaccttgcc     240 tcagggtcc cagacaggtt cagcggcagt gggtcaggaa ctgttttcac actgagaatc    300
agcagactgg aggctgagga tgtgggtatt tattactgta tgcaacatct agaatatcct    360
ttcacgtttg gagggggac caagctggaa ataaaa                               396
```

```
<210> SEQ ID NO 7
<211> LENGTH: 132
<212> TYPE: PRT
<213> ORGANISM: Artificial Sequence
<220> FEATURE:
<223> OTHER INFORMATION: Humanized mouse

<400> SEQUENCE: 7

Met Arg Cys Leu Ala Glu Phe Leu Gly Leu Leu Val Leu Trp Ile Pro
1               5                   10                  15

Gly Ala Ile Gly Asp Ile Val Leu Thr Gln Ala Ala Pro Ser Val Pro
                20                  25                  30

Val Thr Pro Gly Glu Ser Val Ser Ile Ser Cys Arg Ser Ser Lys Ser
            35                  40                  45

Leu Leu His Ser Asp Gly Asn Thr Tyr Leu Tyr Trp Leu Leu Gln Arg
        50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Val Phe
                85                  90                  95

Thr Leu Arg Ile Ser Arg Leu Glu Ala Glu Asp Val Gly Ile Tyr Tyr
            100                 105                 110

Cys Met Gln His Leu Glu Tyr Pro Phe Thr Phe Gly Gly Gly Thr Lys
        115                 120                 125

Leu Glu Ile Lys
    130
```

```
<210> SEQ ID NO 8
<211> LENGTH: 16
<212> TYPE: PRT
<213> ORGANISM: Mus

<400> SEQUENCE: 8

Arg Ser Ser Lys Ser Leu Leu His Ser Asp Gly Asn Thr Tyr Leu Tyr
1               5                   10                  15
```

```
<210> SEQ ID NO 9
<211> LENGTH: 8
<212> TYPE: PRT
<213> ORGANISM: Mus

<400> SEQUENCE: 9

Tyr Arg Met Ser Asn Leu Ala Ser
1               5
```

```
<210> SEQ ID NO 10
<211> LENGTH: 9
<212> TYPE: PRT
<213> ORGANISM: Mus

<400> SEQUENCE: 10

Met Gln His Leu Glu Tyr Pro Phe Thr
1               5
```

```
<210> SEQ ID NO 11
<211> LENGTH: 414
<212> TYPE: DNA
<213> ORGANISM: Artificial Sequence
<220> FEATURE:
<223> OTHER INFORMATION: Humanized mouse

<400> SEQUENCE: 11
atgggatgga gctggatctt tcttttcctc ctgtcaggaa ctgcaggtgt ccgttgccag      60
atccgactgc agcagtctgg acctgagctg gtgaagcctg gggcttcagt gaagatatcc     120
tgcaaggctt ctgggtcctc cttcactgac tactatataa actgggtgaa gcagaagcct     180
ggacagggac ttgagtggat tggatggatt tatcctggaa gcggtaattc tatctacaat     240
gagaacttca aggccaaggc cacattgact gtagacacat cctccagcac agcctacatg     300
catctcagca gcctgacatc tgaggacact gctgtctatt tctgtgcaag agaggctgat     360
tacgacgatg ctttggacta ctggggtcaa ggaacctcgg tcaccgtctc ctca           414

<210> SEQ ID NO 12
<211> LENGTH: 138
<212> TYPE: PRT
<213> ORGANISM: Artificial Sequence
<220> FEATURE:
<223> OTHER INFORMATION: Humanized mouse

<400> SEQUENCE: 12

Met Gly Trp Ser Trp Ile Phe Leu Phe Leu Leu Ser Gly Thr Ala Gly
1               5                   10                  15

Val Arg Cys Gln Ile Arg Leu Gln Gln Ser Gly Pro Glu Leu Val Lys
            20                  25                  30

Pro Gly Ala Ser Val Lys Ile Ser Cys Lys Ala Ser Gly Ser Ser Phe
        35                  40                  45

Thr Asp Tyr Tyr Ile Asn Trp Val Lys Gln Lys Pro Gly Gln Gly Leu
    50                  55                  60

Glu Trp Ile Gly Trp Ile Tyr Pro Gly Ser Gly Asn Ser Ile Tyr Asn
65                  70                  75                  80

Glu Asn Phe Lys Ala Lys Ala Thr Leu Thr Val Asp Thr Ser Ser Ser
                85                  90                  95

Thr Ala Tyr Met His Leu Ser Ser Leu Thr Ser Glu Asp Thr Ala Val
            100                 105                 110

Tyr Phe Cys Ala Arg Glu Ala Asp Tyr Asp Asp Ala Leu Asp Tyr Trp
        115                 120                 125

Gly Gln Gly Thr Ser Val Thr Val Ser Ser
    130                 135

<210> SEQ ID NO 13
<211> LENGTH: 10
<212> TYPE: PRT
<213> ORGANISM: Mus

<400> SEQUENCE: 13

Gly Ser Ser Phe Thr Asp Tyr Tyr Ile Asn
1               5                   10

<210> SEQ ID NO 14
<211> LENGTH: 17
<212> TYPE: PRT
<213> ORGANISM: Mus

<400> SEQUENCE: 14
```

```
Trp Ile Tyr Pro Gly Ser Gly Asn Ser Ile Tyr Asn Glu Asn Phe Lys
1               5                   10                  15

Ala

<210> SEQ ID NO 15
<211> LENGTH: 10
<212> TYPE: PRT
<213> ORGANISM: Mus

<400> SEQUENCE: 15

Glu Ala Asp Tyr Asp Asp Ala Leu Asp Tyr
1               5                   10

<210> SEQ ID NO 16
<211> LENGTH: 384
<212> TYPE: DNA
<213> ORGANISM: Artificial Sequence
<220> FEATURE:
<223> OTHER INFORMATION: Humanized mouse

<400> SEQUENCE: 16
atggtatcca cacctcagtt ccttgtattt ttgcttttct ggattccagc ctccagaggt      60
cacatcttgc tgactcagtc tccagccatt ctgtctgtga gtccaggaga aagagtcagt     120
ttctcctgca gggccagtca gagcattggc acaagcatac actggtatca gcaaagaaca    180
aatggttctc caaggcttct cataaagtat gcttctgagt ctatctctgg gatcccttcc    240
aggtttagtg gcagtggatc agggacagat tttactctta gcatcaacag tgtggagtca    300
gaagatattg cagattatta ctgtcaacaa agtaatagct ggccaacgta cacgttcgga    360
gggggaccaa gctggaaat aaaa                                             384

<210> SEQ ID NO 17
<211> LENGTH: 128
<212> TYPE: PRT
<213> ORGANISM: Artificial Sequence
<220> FEATURE:
<223> OTHER INFORMATION: Humanized mouse

<400> SEQUENCE: 17

Met Val Ser Thr Pro Gln Phe Leu Val Phe Leu Leu Phe Trp Ile Pro
1               5                   10                  15

Ala Ser Arg Gly His Ile Leu Leu Thr Gln Ser Pro Ala Ile Leu Ser
                20                  25                  30

Val Ser Pro Gly Glu Arg Val Ser Phe Ser Cys Arg Ala Ser Gln Ser
            35                  40                  45

Ile Gly Thr Ser Ile His Trp Tyr Gln Gln Arg Thr Asn Gly Ser Pro
        50                  55                  60

Arg Leu Leu Ile Lys Tyr Ala Ser Glu Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Ser Glu Asp Ile Ala Asp Tyr Tyr Cys Gln Gln Ser Asn
            100                 105                 110

Ser Trp Pro Thr Tyr Thr Phe Gly Gly Gly Thr Lys Leu Glu Ile Lys
        115                 120                 125

<210> SEQ ID NO 18
<211> LENGTH: 11
<212> TYPE: PRT
<213> ORGANISM: Mus
```

<400> SEQUENCE: 18

Arg Ala Ser Gln Ser Ile Gly Thr Ser Ile His
1               5                   10

<210> SEQ ID NO 19
<211> LENGTH: 7
<212> TYPE: PRT
<213> ORGANISM: Mus

<400> SEQUENCE: 19

Tyr Ala Ser Glu Ser Ile Ser
1               5

<210> SEQ ID NO 20
<211> LENGTH: 10
<212> TYPE: PRT
<213> ORGANISM: Mus

<400> SEQUENCE: 20

Gln Gln Ser Asn Ser Trp Pro Thr Tyr Thr
1               5                   10

<210> SEQ ID NO 21
<211> LENGTH: 426
<212> TYPE: DNA
<213> ORGANISM: Artificial Sequence
<220> FEATURE:
<223> OTHER INFORMATION: Humanized mouse

<400> SEQUENCE: 21

```
atgagatgga gctgtatcat cctcttcttg gtagcaacag ctacaggtgt caactcccag      60
gtccaactgc agcagcctgg ggctgagctt gtgatgcctg ggcttcagc gaagatgtcc     120
tgcaaggctt ctggctacac actcactgac tactggatgc actgggtgaa gcagaggcct    180
ggacaaggcc ttgagtggat cggagcgatt gatatttctg atagttattc tagctacaat    240
caaaagttca agggcaaggc cacattgact gtagacgaat cctccagcac agcctacatg    300
cagctcacca gcctgacatc tgaggactct gcggtctatt actgtgcaag atcccctttc    360
tacaatagta gagggggaa ctactttgac tactggggcc aaggcaccac tctcacagtc    420
tcctca                                                                426
```

<210> SEQ ID NO 22
<211> LENGTH: 142
<212> TYPE: PRT
<213> ORGANISM: Artificial Sequence
<220> FEATURE:
<223> OTHER INFORMATION: Humanized mouse

<400> SEQUENCE: 22

Met Arg Trp Ser Cys Ile Ile Leu Phe Leu Val Ala Thr Ala Thr Gly
1               5                   10                  15

Val Asn Ser Gln Val Gln Leu Gln Gln Pro Gly Ala Glu Leu Val Met
                20                  25                  30

Pro Gly Ala Ser Ala Lys Met Ser Cys Lys Ala Ser Gly Tyr Thr Leu
            35                  40                  45

Thr Asp Tyr Trp Met His Trp Val Lys Gln Arg Pro Gly Gln Gly Leu
        50                  55                  60

Glu Trp Ile Gly Ala Ile Asp Ile Ser Asp Ser Tyr Ser Ser Tyr Asn
65                  70                  75                  80

Gln Lys Phe Lys Gly Lys Ala Thr Leu Thr Val Asp Glu Ser Ser Ser
                85                  90                  95

Thr Ala Tyr Met Gln Leu Thr Ser Leu Thr Ser Glu Asp Ser Ala Val
            100                 105                 110

Tyr Tyr Cys Ala Arg Ser Pro Phe Tyr Asn Ser Arg Gly Gly Asn Tyr
        115                 120                 125

Phe Asp Tyr Trp Gly Gln Gly Thr Thr Leu Thr Val Ser Ser
        130                 135                 140

<210> SEQ ID NO 23
<211> LENGTH: 10
<212> TYPE: PRT
<213> ORGANISM: Mus

<400> SEQUENCE: 23

Gly Tyr Thr Leu Thr Asp Tyr Trp Met His
1               5                   10

<210> SEQ ID NO 24
<211> LENGTH: 17
<212> TYPE: PRT
<213> ORGANISM: Mus

<400> SEQUENCE: 24

Ala Ile Asp Ile Ser Asp Ser Tyr Ser Tyr Asn Gln Lys Phe Lys
1               5                   10                  15

Gly

<210> SEQ ID NO 25
<211> LENGTH: 14
<212> TYPE: PRT
<213> ORGANISM: Mus

<400> SEQUENCE: 25

Ser Pro Phe Tyr Asn Ser Arg Gly Gly Asn Tyr Phe Asp Tyr
1               5                   10

<210> SEQ ID NO 26
<211> LENGTH: 384
<212> TYPE: DNA
<213> ORGANISM: Artificial Sequence
<220> FEATURE:
<223> OTHER INFORMATION: Humanized mouse

<400> SEQUENCE: 26
atgatgtcct ctgctcagtt ccttggtctc ctgttgctct gttttcaagg taccagatgt      60
gatatccaga tgacacagac tacatcctcc ctgtctgcct ctctgggaga cagagtcacc     120
atcagttgca gggcaagtca ggacattagc aattatttaa actggtatca gcagaaacca     180
gatggaactg ttaaactcct gatctactac acatcaagat tacactcagg agtcccatca     240
aggttcagtg gcagtgggtc tggaacagat tattctctca ccattagcaa cctggagcaa     300
gaagatattg ccacttactt ttgccaacag ggtgatacgc ttcctccgtg gacgttcggt     360
ggaggcacca agctggaaat caaa                                            384

<210> SEQ ID NO 27
<211> LENGTH: 128
<212> TYPE: PRT
<213> ORGANISM: Artificial Sequence
<220> FEATURE:
<223> OTHER INFORMATION: Humanized mouse

<400> SEQUENCE: 27

Met Met Ser Ser Ala Gln Phe Leu Gly Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asp
            100                 105                 110

Thr Leu Pro Pro Trp Thr Phe Gly Gly Gly Thr Lys Leu Glu Ile Lys
        115                 120                 125

<210> SEQ ID NO 28
<211> LENGTH: 11
<212> TYPE: PRT
<213> ORGANISM: Mus

<400> SEQUENCE: 28

Arg Ala Ser Gln Asp Ile Ser Asn Tyr Leu Asn
1               5                   10

<210> SEQ ID NO 29
<211> LENGTH: 7
<212> TYPE: PRT
<213> ORGANISM: Mus

<400> SEQUENCE: 29

Tyr Thr Ser Arg Leu His Ser
1               5

<210> SEQ ID NO 30
<211> LENGTH: 10
<212> TYPE: PRT
<213> ORGANISM: Mus

<400> SEQUENCE: 30

Gln Gln Gly Asp Thr Leu Pro Pro Trp Thr
1               5                   10

<210> SEQ ID NO 31
<211> LENGTH: 447
<212> TYPE: DNA
<213> ORGANISM: Artificial Sequence
<220> FEATURE:
<223> OTHER INFORMATION: Humanized mouse

<400> SEQUENCE: 31
atgggatgga cctggatctt tctcttcttc ctgtcaggaa ctgcaggtgt cctctctgag      60
gtcctgctgc tacagtctgg acctgaactg gtgaagcctg ggacttcagt gaaaatcccc     120
tgcaaggctt ctggatacac attcactgac tacaacgtgg actgggtgaa gcagcgccat     180
ggaaagggcc ttgagtggat tgagatatt aatccaaaca atggtggtac tatctacagt      240
cagaaattca aggcaaggc cacattgact gttgacaagt cctccagcac agccttcatg      300

```
gagctccgca gcctgacatc tgaggacact gcagtctatt tctgtgcaag gaactatagg    360
tggtttggtg ctatggacca ctgggggtca ggaacctcag tcaccgtctc ctcagccaaa    420
acaacagccc catcggtcta tccactg                                        447
```

<210> SEQ ID NO 32
<211> LENGTH: 138
<212> TYPE: PRT
<213> ORGANISM: Artificial Sequence
<220> FEATURE:
<223> OTHER INFORMATION: Humanized mouse

<400> SEQUENCE: 32

```
Met Gly Trp Thr Trp Ile Phe Leu Phe Phe Leu Ser Gly Thr Ala Gly
1               5                   10                  15

Val Leu Ser Glu Val Leu Leu Leu Gln Ser Gly Pro Glu Leu Val Lys
            20                  25                  30

Pro Gly Thr Ser Val Lys Ile Pro Cys Lys Ala Ser Gly Tyr Thr Phe
        35                  40                  45

Thr Asp Tyr Asn Val Asp Trp Val Lys Gln Arg His Gly Lys Gly Leu
    50                  55                  60

Glu Trp Ile Gly Asp Ile Asn Pro Asn Asn Gly Gly Thr Ile Tyr Ser
65                  70                  75                  80

Gln Lys Phe Lys Gly Lys Ala Thr Leu Thr Val Asp Lys Ser Ser Ser
                85                  90                  95

Thr Ala Phe Met Glu Leu Arg Ser Leu Thr Ser Glu Asp Thr Ala Val
            100                 105                 110

Tyr Phe Cys Ala Arg Asn Tyr Arg Trp Phe Gly Ala Met Asp His Trp
        115                 120                 125

Gly Gln Gly Thr Ser Val Thr Val Ser Ser
    130                 135
```

<210> SEQ ID NO 33
<211> LENGTH: 5
<212> TYPE: PRT
<213> ORGANISM: Mus

<400> SEQUENCE: 33

```
Asp Tyr Asn Val Asp
1               5
```

<210> SEQ ID NO 34
<211> LENGTH: 17
<212> TYPE: PRT
<213> ORGANISM: Mus

<400> SEQUENCE: 34

```
Asp Ile Asn Pro Asn Asn Gly Gly Thr Ile Tyr Ser Gln Lys Phe Lys
1               5                   10                  15

Gly
```

<210> SEQ ID NO 35
<211> LENGTH: 10
<212> TYPE: PRT
<213> ORGANISM: Mus

<400> SEQUENCE: 35

```
Asn Tyr Arg Trp Phe Gly Ala Met Asp His
1               5                   10
```

```
<210> SEQ ID NO 36
<211> LENGTH: 547
<212> TYPE: DNA
<213> ORGANISM: Artificial Sequence
<220> FEATURE:
<223> OTHER INFORMATION: Humanized mouse

<400> SEQUENCE: 36
atggagacag acacaatcct gctatgggtg ctgctgctct gggttccagg ttccactggt    60
gacattgtgt tgacccaatc tccagcttct ttggctgtgt ctccaggca gagggccacc   120 atttcctgca aggccagtca agtcttgat tatgaaggtg atagtgatat gaattggtac    180
caacagaaac caggacagcc acccagactc ctcatctctg gtgcatccaa tctagagtct   240
gggatcccag ccaggttcag tggcagtggg tctgggacag acttcactgt aacatccat    300 cctgtggagg aggaggatgc tgcaacctat tactgtcagc aaagtactga ggatcctcgg   360
acgttcggtg aggcaccaa gctggaaatc aaacgggctg atgctgcacc aactgtatcc    420
atcttcccac catccagtga gcagttaaca tctggaggtg cctcagtcgt gtgcttcttg    480
aacaacttct accccaaaga catcaatgtc aagtggaaga ttgatggcag tgaacgacaa    540
aatggcg                                                             547

<210> SEQ ID NO 37
<211> LENGTH: 131
<212> TYPE: PRT
<213> ORGANISM: Artificial Sequence
<220> FEATURE:
<223> OTHER INFORMATION: Humanized mouse

<400> SEQUENCE: 37

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Pro Gly Gln Arg Ala Thr Ile Ser Cys Lys Ala Ser Gln Ser
        35                  40                  45

Leu Asp Tyr Glu Gly Asp Ser Asp Met Asn Trp Tyr Gln Gln Lys Pro
    50                  55                  60

Gly Gln Pro Pro Arg Leu Leu Ile Ser Gly Ala Ser Asn Leu Glu Ser
65                  70                  75                  80

Gly Ile Pro Ala Arg Phe Ser Gly Ser Gly Ser Gly Thr Asp Phe Thr
                85                  90                  95

Val Asn Ile His Pro Val Glu Glu Asp Ala Ala Thr Tyr Tyr Cys
                100                 105                 110

Gln Gln Ser Thr Glu Asp Pro Arg Thr Phe Gly Gly Gly Thr Lys Leu
        115                 120                 125

Glu Ile Lys
    130

<210> SEQ ID NO 38
<211> LENGTH: 15
<212> TYPE: PRT
<213> ORGANISM: Mus

<400> SEQUENCE: 38

Lys Ala Ser Gln Ser Leu Asp Tyr Glu Gly Asp Ser Asp Met Asn
1               5                   10                  15

<210> SEQ ID NO 39
```

```
<211> LENGTH: 7
<212> TYPE: PRT
<213> ORGANISM: Mus

<400> SEQUENCE: 39

Gly Ala Ser Asn Leu Glu Ser
1               5

<210> SEQ ID NO 40
<211> LENGTH: 9
<212> TYPE: PRT
<213> ORGANISM: Mus

<400> SEQUENCE: 40

Gln Gln Ser Thr Glu Asp Pro Arg Thr
1               5

<210> SEQ ID NO 41
<211> LENGTH: 218
<212> TYPE: PRT
<213> ORGANISM: Artificial Sequence
<220> FEATURE:
<223> OTHER INFORMATION: Humanized mouse

<400> SEQUENCE: 41

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Leu Asp Tyr Glu
            20                  25                  30

Gly Asp Ser Asp Met Asn Trp Tyr Leu Gln Lys Pro Gly Gln Pro Pro
        35                  40                  45

Gln Leu Leu Ile Tyr Gly Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Thr
                85                  90                  95

Glu Asp Pro Arg Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 42
<211> LENGTH: 449
<212> TYPE: PRT
<213> ORGANISM: Artificial Sequence
<220> FEATURE:
<223> OTHER INFORMATION: Humanized mouse
```

<400> SEQUENCE: 42

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
        35                  40                  45

Gly Asp Ile Asn Pro Asn Gly Gly Thr Ile Tyr Ala Gln Lys Phe
50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys

```
                    405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 43
<211> LENGTH: 218
<212> TYPE: PRT
<213> ORGANISM: Artificial Sequence
<220> FEATURE:
<223> OTHER INFORMATION: Humanized mouse

<400> SEQUENCE: 43

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Leu Asp Tyr Glu
            20                  25                  30

Gly Asp Ser Asp Met Asn Trp Tyr Leu Gln Lys Pro Gly Gln Pro Pro
        35                  40                  45

Gln Leu Leu Ile Tyr Gly Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Thr
                85                  90                  95

Glu Asp Pro Arg Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 44
<211> LENGTH: 449
<212> TYPE: PRT
<213> ORGANISM: Artificial Sequence
<220> FEATURE:
<223> OTHER INFORMATION: Humanized mouse

<400> SEQUENCE: 44

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
```

```
             35                  40                  45
Gly Asp Ile Asn Pro Asn Ser Gly Gly Thr Ile Tyr Ala Gln Lys Phe
 50                  55                  60

Gln Glu Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Tyr Arg Trp Phe Gly Ala Met Asp His Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

```
<210> SEQ ID NO 45
<211> LENGTH: 218
<212> TYPE: PRT
<213> ORGANISM: Artificial Sequence
<220> FEATURE:
<223> OTHER INFORMATION: Humanized mouse

<400> SEQUENCE: 45

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Leu Asp Tyr Glu
            20                  25                  30

Gly Asp Ser Asp Met Asn Trp Tyr Leu Gln Lys Pro Gly Gln Pro Pro
        35                  40                  45

Gln Leu Leu Ile Tyr Gly Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Thr
                85                  90                  95

Glu Asp Pro Arg Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 46
<211> LENGTH: 449
<212> TYPE: PRT
<213> ORGANISM: Artificial Sequence
<220> FEATURE:
<223> OTHER INFORMATION: Humanized mouse

<400> SEQUENCE: 46

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
        35                  40                  45

Gly Asp Ile Asn Pro Asn Asp Gly Gly Thr Ile Tyr Ala Gln Lys Phe
    50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Asn Tyr Arg Trp Phe Gly Ala Met Asp His Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 47
<211> LENGTH: 218
<212> TYPE: PRT
<213> ORGANISM: Artificial Sequence
<220> FEATURE:
<223> OTHER INFORMATION: Humanized mouse

<400> SEQUENCE: 47

```
Asp Ile Val Met Thr Gln Thr Pro Leu Ser Leu Ser Val Thr Pro Gly
 1               5                  10                  15

Gln Pro Ala Ser Ile Ser Cys Lys Ala Ser Gln Ser Leu Asp Tyr Glu
            20                  25                  30

Gly Asp Ser Asp Met Asn Trp Tyr Leu Gln Lys Pro Gly Gln Pro Pro
        35                  40                  45

Gln Leu Leu Ile Tyr Gly Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Thr
                85                  90                  95

Glu Asp Pro Arg Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 48
<211> LENGTH: 449
<212> TYPE: PRT
<213> ORGANISM: Artificial Sequence
<220> FEATURE:
<223> OTHER INFORMATION: Humanized mouse

<400> SEQUENCE: 48

Gln Met Gln Leu Val Gln Ser Gly Pro Glu Val Lys Lys Pro Gly Thr
 1               5                  10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
        35                  40                  45

Gly Asp Ile Asn Pro Asn Gln Gly Gly Thr Ile Tyr Ala Gln Lys Phe
    50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 49
<211> LENGTH: 218
<212> TYPE: PRT
<213> ORGANISM: Artificial Sequence
<220> FEATURE:
<223> OTHER INFORMATION: Humanized mouse

<400> SEQUENCE: 49

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Leu Asp Tyr Glu
                20                  25                  30

Gly Asp Ser Asp Met Asn Trp Tyr Leu Gln Lys Pro Gly Gln Pro Pro
            35                  40                  45

Gln Leu Leu Ile Tyr Gly Ala Ser Asn Leu Glu Ser Gly Val Pro Asp
```

```
                    50                  55                  60
Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln Gln Ser Thr
                     85                  90                  95

Glu Asp Pro Arg Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215
```

<210> SEQ ID NO 50
<211> LENGTH: 446
<212> TYPE: PRT
<213> ORGANISM: Artificial Sequence
<220> FEATURE:
<223> OTHER INFORMATION: Humanized mouse

<400> SEQUENCE: 50

```
Gln Met Gln Leu Val Gln Ser Gly Pro Glu Val Lys Lys Pro Gly Thr
  1               5                  10                  15

Ser Val Lys Val Ser Cys Lys Ala Ser Gly Tyr Thr Phe Thr Asp Tyr
                 20                  25                  30

Asn Val Asp Trp Val Arg Gln Ala Arg Gly Gln Arg Leu Glu Trp Ile
             35                  40                  45

Gly Asp Ile Asn Pro Asn Asn Gly Gly Thr Ile Tyr Ala Gln Lys Phe
 50                  55                  60

Gln Glu Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Tyr Arg Trp Phe Gly Ala Met Asp His Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
```

195                 200                 205
Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 51
<211> LENGTH: 218
<212> TYPE: PRT
<213> ORGANISM: Artificial Sequence
<220> FEATURE:
<223> OTHER INFORMATION: Humanized mouse

<400> SEQUENCE: 51

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Leu Asp Tyr Glu
                20                  25                  30

Gly Asp Ser Asp Met Asn Trp Tyr Leu Gln Lys Pro Gly Gln Pro Pro
            35                  40                  45

Gln Leu Leu Ile Tyr Gly Ala Ser Asn Leu Glu Ser Gly Val Pro Asp
        50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Thr
                85                  90                  95

Glu Asp Pro Arg Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln

```
                    115                 120                 125
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 52
<211> LENGTH: 446
<212> TYPE: PRT
<213> ORGANISM: Artificial Sequence
<220> FEATURE:
<223> OTHER INFORMATION: Humanized mouse

<400> SEQUENCE: 52

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Asn Val Asp Trp Val Arg Gln Ala Arg Gly Gln Arg Leu Glu Trp Ile
            35                  40                  45

Gly Asp Ile Asn Pro Asn Asp Gly Gly Thr Ile Tyr Ala Gln Lys Phe
        50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
```

```
                      260                 265                 270
    Gln Phe Asn Trp Tyr Val Asp Gly Val Glu Val His Asn Ala Lys Thr
                275                 280                 285
    Lys Pro Arg Glu Glu Gln Phe Asn Ser Thr Tyr Arg Val Val Ser Val
            290                 295                 300
    Leu Thr Val Leu His Gln Asp Trp Leu Asn Gly Lys Glu Tyr Lys Cys
    305                 310                 315                 320
    Lys Val Ser Asn Lys Gly Leu Pro Ser Ser Ile Glu Lys Thr Ile Ser
                    325                 330                 335
    Lys Ala Lys Gly Gln Pro Arg Glu Pro Gln Val Tyr Thr Leu Pro Pro
                340                 345                 350
    Ser Gln Glu Glu Met Thr Lys Asn Gln Val Ser Leu Thr Cys Leu Val
                355                 360                 365
    Lys Gly Phe Tyr Pro Ser Asp Ile Ala Val Glu Trp Glu Ser Asn Gly
            370                 375                 380
    Gln Pro Glu Asn Asn Tyr Lys Thr Thr Pro Pro Val Leu Asp Ser Asp
    385                 390                 395                 400
    Gly Ser Phe Phe Leu Tyr Ser Arg Leu Thr Val Asp Lys Ser Arg Trp
                    405                 410                 415
    Gln Glu Gly Asn Val Phe Ser Cys Ser Val Met His Glu Ala Leu His
                420                 425                 430
    Asn His Tyr Thr Gln Lys Ser Leu Ser Leu Ser Leu Gly Lys
                435                 440                 445

<210> SEQ ID NO 53
<211> LENGTH: 218
<212> TYPE: PRT
<213> ORGANISM: Artificial Sequence
<220> FEATURE:
<223> OTHER INFORMATION: Humanized mouse

<400> SEQUENCE: 53

Asp Ile Val Met Thr Gln Thr Pro Leu Ser Leu Ser Val Thr Pro Gly
    1               5                   10                  15
    Gln Pro Ala Ser Ile Ser Cys Lys Ala Ser Gln Ser Leu Asp Tyr Glu
                20                  25                  30
    Gly Asp Ser Asp Met Asn Trp Tyr Leu Gln Lys Pro Gly Gln Pro Pro
            35                  40                  45
    Gln Leu Leu Ile Tyr Gly Ala Ser Asn Leu Glu Ser Gly Val Pro Asp
        50                  55                  60
    Arg Phe Ser Gly Ser Gly Ser Gly Thr Asp Phe Thr Leu Lys Ile Ser
    65                  70                  75                  80
    Arg Val Glu Ala Glu Asp Val Gly Val Tyr Tyr Cys Gln Gln Ser Thr
                    85                  90                  95
    Glu Asp Pro Arg Thr Phe Gly Gly Gly Thr Lys Val Glu Ile Lys Arg
                100                 105                 110
    Thr Val Ala Ala Pro Ser Val Phe Ile Phe Pro Pro Ser Asp Glu Gln
                115                 120                 125
    Leu Lys Ser Gly Thr Ala Ser Val Val Cys Leu Leu Asn Asn Phe Tyr
            130                 135                 140
    Pro Arg Glu Ala Lys Val Gln Trp Lys Val Asp Asn Ala Leu Gln Ser
    145                 150                 155                 160
    Gly Asn Ser Gln Glu Ser Val Thr Glu Gln Asp Ser Lys Asp Ser Thr
                    165                 170                 175
    Tyr Ser Leu Ser Ser Thr Leu Thr Leu Ser Lys Ala Asp Tyr Glu Lys
```

-continued

```
                180                 185                 190
His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 54
<211> LENGTH: 446
<212> TYPE: PRT
<213> ORGANISM: Artificial Sequence
<220> FEATURE:
<223> OTHER INFORMATION: Humanized mouse

<400> SEQUENCE: 54

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
        35                  40                  45

Gly Asp Ile Asn Pro Asn Ser Gly Gly Thr Ile Tyr Ala Gln Lys Phe
    50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
```

```
                    325                 330                 335
Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 55
<211> LENGTH: 218
<212> TYPE: PRT
<213> ORGANISM: Artificial Sequence
<220> FEATURE:
<223> OTHER INFORMATION: Humanized mouse

<400> SEQUENCE: 55

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Leu Asp Tyr Glu
            20                  25                  30

Gly Asp Ser Asp Met Asn Trp Tyr Leu Gln Lys Pro Gly Gln Pro Pro
        35                  40                  45

Gln Leu Leu Ile Tyr Gly Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Thr
                85                  90                  95

Glu Asp Pro Arg Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 56
<211> LENGTH: 446
<212> TYPE: PRT
```

<213> ORGANISM: Artificial Sequence
<220> FEATURE:
<223> OTHER INFORMATION: Humanized mouse

<400> SEQUENCE: 56

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
        35                  40                  45

Gly Asp Ile Asn Pro Asn Gln Gly Gly Thr Ile Tyr Ala Gln Lys Phe
    50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp

```
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
                420                 425                 430
Asn His Tyr Thr Gln Lys Ser Leu Ser Leu Ser Leu Gly Lys
                435                 440                 445

<210> SEQ ID NO 57
<211> LENGTH: 218
<212> TYPE: PRT
<213> ORGANISM: Artificial Sequence
<220> FEATURE:
<223> OTHER INFORMATION: Humanized mouse

<400> SEQUENCE: 57

Asp Ile Val Met Thr Gln Thr Pro Leu Ser Leu Ser Val Thr Pro Gly
1               5                   10                  15
Gln Pro Ala Ser Ile Ser Cys Lys Ala Ser Gln Ser Leu Asp Tyr Glu
                20                  25                  30
Gly Asp Ser Asp Met Asn Trp Tyr Leu Gln Lys Pro Gly Gln Pro Pro
            35                  40                  45
Gln Leu Leu Ile Tyr Gly Ala Ser Asn Leu Glu Ser Gly Val Pro Asp
    50                  55                  60
Arg Phe Ser Gly Ser Gly Ser Gly Thr Asp Phe Thr Leu Lys Ile Ser
65                  70                  75                  80
Arg Val Glu Ala Glu Asp Val Gly Val Tyr Tyr Cys Gln Gln Ser Thr
                85                  90                  95
Glu Asp Pro Arg Thr Phe Gly Gly Gly Thr Lys Val Glu Ile Lys Arg
                100                 105                 110
Thr Val Ala Ala Pro Ser Val Phe Ile Phe Pro Pro Ser Asp Glu Gln
            115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
                180                 185                 190
His Lys Val Tyr Ala Cys Glu Val Thr His Gln Gly Leu Ser Ser Pro
            195                 200                 205
Val Thr Lys Ser Phe Asn Arg Gly Glu Cys
    210                 215

<210> SEQ ID NO 58
<211> LENGTH: 446
<212> TYPE: PRT
<213> ORGANISM: Artificial Sequence
<220> FEATURE:
<223> OTHER INFORMATION: Humanized mouse

<400> SEQUENCE: 58

Gln Met Gln Leu Val Gln Ser Gly Pro Glu Val Lys Lys Pro Gly Thr
1               5                   10                  15
Ser Val Lys Val Ser Cys Lys Ala Ser Gly Tyr Thr Phe Thr Asp Tyr
                20                  25                  30
```

-continued

```
Asn Val Asp Trp Val Arg Gln Ala Arg Gly Gln Arg Leu Glu Trp Ile
        35                  40                  45
Gly Asp Ile Asn Pro Asn Gly Gly Thr Ile Tyr Ala Gln Lys Phe
 50                  55                  60
Gln Glu Arg Val Thr Ile Thr Val Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Asn Tyr Arg Trp Phe Gly Ala Met Asp His Trp Gly Gln Gly
                100                 105                 110
Thr Thr Val Thr Val Ser Ser Ala Ser Thr Lys Gly Pro Ser Val Phe
            115                 120                 125
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
        195                 200                 205
Ser Asn Thr Lys Val Asp Lys Arg Val Glu Ser Lys Tyr Gly Pro Pro
    210                 215                 220
Cys Pro Pro Cys Pro Ala Pro Glu Phe Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys
        435                 440                 445
```

```
<210> SEQ ID NO 59
<211> LENGTH: 17
<212> TYPE: PRT
<213> ORGANISM: Mus

<400> SEQUENCE: 59

Asp Ile Asn Pro Asn Asn Gly Gly Thr Ile Tyr Ala Gln Lys Phe Gln
1               5                   10                  15

Glu

<210> SEQ ID NO 60
<211> LENGTH: 17
<212> TYPE: PRT
<213> ORGANISM: Mus

<400> SEQUENCE: 60

Asp Ile Asn Pro Asn Ser Gly Gly Thr Ile Tyr Ala Gln Lys Phe Gln
1               5                   10                  15

Glu

<210> SEQ ID NO 61
<211> LENGTH: 17
<212> TYPE: PRT
<213> ORGANISM: Mus

<400> SEQUENCE: 61

Asp Ile Asn Pro Asn Asp Gly Gly Thr Ile Tyr Ala Gln Lys Phe Gln
1               5                   10                  15

Glu

<210> SEQ ID NO 62
<211> LENGTH: 17
<212> TYPE: PRT
<213> ORGANISM: Mus

<400> SEQUENCE: 62

Asp Ile Asn Pro Asn Gln Gly Gly Thr Ile Tyr Ala Gln Lys Phe Gln
1               5                   10                  15

Glu

<210> SEQ ID NO 63
<211> LENGTH: 17
<212> TYPE: PRT
<213> ORGANISM: Mus

<400> SEQUENCE: 63

Asp Ile Asn Pro Asn Gly Gly Gly Thr Ile Tyr Ala Gln Lys Phe Gln
1               5                   10                  15

Glu

<210> SEQ ID NO 64
<211> LENGTH: 17
<212> TYPE: PRT
<213> ORGANISM: Mus
<220> FEATURE:
<221> NAME/KEY: MISC_FEATURE
<222> LOCATION: (6)..(6)
<223> OTHER INFORMATION: X is D,N,S or Q
<220> FEATURE:
<221> NAME/KEY: MISC_FEATURE
<222> LOCATION: (12)..(12)
<223> OTHER INFORMATION: X is A or S
<220> FEATURE:
<221> NAME/KEY: MISC_FEATURE
```

```
<222> LOCATION: (16)..(16)
<223> OTHER INFORMATION: X is Q or K
<220> FEATURE:
<221> NAME/KEY: MISC_FEATURE
<222> LOCATION: (17)..(17)
<223> OTHER INFORMATION: X is E or G

<400> SEQUENCE: 64

Asp Ile Asn Pro Asn Xaa Gly Gly Thr Ile Tyr Xaa Gln Lys Phe Xaa
1               5                   10                  15

Xaa

<210> SEQ ID NO 65
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (13)..(19)
<223> OTHER INFORMATION: Xaa can be any naturally occurring amino acid

<400> SEQUENCE: 65

Xaa Ser Xaa Ser Xaa Asp Tyr Glu Gly Asp Ser Asp Xaa Xaa Xaa Xaa
1               5                   10                  15

Xaa Xaa Xaa
```